United States Patent
Skerlj et al.

(10) Patent No.: US 9,493,510 B2
(45) Date of Patent: Nov. 15, 2016

(54) PEPTIDOMIMETIC COMPOUNDS

(71) Applicant: Noliva Therapeutics LLC, West Newton, MA (US)

(72) Inventors: Renato T. Skerlj, West Newton, MA (US); Andrew C. Good, Wallingford, CT (US)

(73) Assignee: NOLIVA THERAPEUTICS LLC, West Newton, MA (US)

( * ) Notice: Subject to any disclaimer, the term of this patent is extended or adjusted under 35 U.S.C. 154(b) by 0 days.

(21) Appl. No.: 14/759,867

(22) PCT Filed: Jan. 10, 2014

(86) PCT No.: PCT/US2014/011112
§ 371 (c)(1),
(2) Date: Jul. 8, 2015

(87) PCT Pub. No.: WO2014/110420
PCT Pub. Date: Jul. 17, 2014

(65) Prior Publication Data
US 2015/0353606 A1 Dec. 10, 2015

Related U.S. Application Data

(60) Provisional application No. 61/751,163, filed on Jan. 10, 2013.

(51) Int. Cl.
| | | |
|---|---|---|
| *A61K 38/00* | (2006.01) | |
| *A61P 35/00* | (2006.01) | |
| *C07K 7/08* | (2006.01) | |
| *C07K 5/103* | (2006.01) | |
| *C07K 7/06* | (2006.01) | |
| *G06F 19/16* | (2011.01) | |
| *G06F 19/18* | (2011.01) | |

(52) U.S. Cl.
CPC ............... *C07K 7/08* (2013.01); *C07K 5/1008* (2013.01); *C07K 7/06* (2013.01); *G06F 19/16* (2013.01); *G06F 19/18* (2013.01)

(58) Field of Classification Search
CPC ............................. A61K 38/00; A61K 38/005
See application file for complete search history.

(56) References Cited

U.S. PATENT DOCUMENTS

| | | | |
|---|---|---|---|
| 7,723,469 B2 * | 5/2010 | Walensky | C07K 14/001 530/317 |
| 2008/0194535 A1 | 8/2008 | Marcin et al. | |
| 2008/0219962 A1 | 9/2008 | Bae et al. | |
| 2009/0326192 A1 | 12/2009 | Nash et al. | |
| 2011/0269244 A1 | 11/2011 | Petter et al. | |
| 2012/0034593 A1 | 2/2012 | Wong et al. | |

OTHER PUBLICATIONS

Al-Harbi S, et al., "An antiapoptotic BCL-2 family expression index predicts the response of chronic lymphocytic leukemia to ABT-737" Blood. Sep. 29, 2011;118(13):3579-90. Epub Jul. 19, 2011.

Bajwa N, et al., "Inhibitors of the anti-apoptotic Bcl-2 proteins: a patent review", Expert Opin Ther Pat. Jan. 2012;22(1):37-55. Epub Dec. 23, 2011.
Barf T, Kaptein A, "Irreversible protein kinase inhibitors: balancing the benefits and risks", J Med Chem. Jul. 26, 2012; 55(14):6243-62.
Berman HM, et al., "The Protein Data Bank", Nucleic Acids Res. Jan. 1, 2000;28(1):235-42.
Clark RJ, et al., "The engineering of an orally active conotoxin for the treatment of neuropathic pain", Angew Chem Int Ed Engl. Sep. 3, 2010;49(37):6545-8.
Daly NL, et al., "Bioactive cystine knot proteins", Curr Opin Chem Biol. Jun. 2011;15(3):362-8. Epub Feb. 27, 2011.
Haq R, et al. "BCL2A1 is a lineage-specific antiapoptotic melanoma oncogene that confers resistance to BRAF inhibition", Proc Natl Acad Sci U S A. Mar. 12, 2013;110(11). Epub Feb. 27, 2013.
Kim MK, et al., "The C-terminal region of Bfl-1 sensitizes non-small cell lung cancer to gemcitabine-induced apoptosis by suppressing NF-κB activity and down-regulating Bfl-1", Mol Cancer Aug. 16, 2011;10:98.
Piva R, et al., "Functional validation of the anaplastic lymphoma kinase signature identifies CEBPB and BCL2A1 as critical target genes", J Clin Invest. Dec. 2006;116(12):3171-82. Epub Nov. 16, 2006.
Singh J, et al., "The resurgence of covalent drugs", Nat Rev Drug Discov. Apr. 2011;10(4):307-17.
Surade S, et al., "Structural biology and drug discovery of difficult targets: the limits of ligandability", Chem Biol. Jan. 27, 2012;19(1):42-50.
Terlau H, et al., "Conus venoms: a rich source of novel ion channel-targeted peptides", Physiol Rev. Jan. 2004;84(1):41-68.
Tse C, et al., "ABT-263: a potent and orally bioavailable Bcl-2 family inhibitor", Cancer Res. May 1, 2008;68(9):3421-8. Verdine GL, Hilinski GJ, "Stapled peptides for intracellular drug targets", Methods Enzymol. 2012; Protein Engineering for Therapeutics, Academic Press, 503:3-33.
Vogler M, "Concurrent up-regulation of BCL-XL and BCL2A1 induces approximately 1000-fold resistance to ABT-737 in chronic lymphocytic leukemia", Blood. Apr. 30, 2009;113(18):4403-13.
Vogler M, "BCL2A1: the underdog in the BCL2 family", Cell Death Differ. 2012, Jan.;19(1):67-74, Epub Nov. 11, 2011.
Walensky LD, et al., "Activation of apoptosis in vivo by a hydrocarbon-stapled BH3 helix", Science. Sep. 3, 2004;305(5689):1466-70.
International Search Report and Written Opinion issued for International patent application No. PCT/US2014/011112, bearing a mailing date of Jun. 23, 2014, 15 pages.
International Preliminary Report on Patentability issued for International patent application No. PCT/US2014/011112, issued on Jul. 14, 2015, 7 pages.

* cited by examiner

*Primary Examiner* — Hasan Ahmed
*Assistant Examiner* — Kaipeen Yang
(74) *Attorney, Agent, or Firm* — Duane Morris LLP

(57) ABSTRACT

The present invention relates to inhibitors of protein-protein interactions (PPI). Specifically, the present invention relates to a structural informatics approach to designing peptidomimetic macrocycles containing an amino acid "warhead" for ligand-directed covalent modification of cysteine and lysine-containing proteins for the treatment of diseases such as cancer. Further included is the targeting of components of the BCL2 signaling pathway, specifically BCL2-A1 and MCL-1.

11 Claims, 7 Drawing Sheets

2a

2i

2b

2j

2c

2k

2d

2l

2e

2m

2f

2n

2g

2o

2h

2p

PEPTIDOMIMETIC COMPOUNDS

CROSS-REFERENCE TO RELATED APPLICATIONS

This application is a U.S. national stage application under 35 U.S.C. §371 of International Application No. PCT/US2014/011112, filed Jan. 10, 2014, which claims the benefit of U.S. Provisional Patent Application No. 61/751,163, filed Jan. 10, 2013, which is incorporated by reference herein in its entirety.

BACKGROUND OF THE INVENTION

The exploitation of cellular disease targets is particularly challenging for the most ubiquitous target class, protein-protein interactions, where large and shallow interaction surfaces often render inhibition by small molecules a major challenge (Surade & Blundell (2012), Chem. Biol. 19: 42-50). While peptides have proven an effective alternative for some protein-protein extracellular receptors, their role has been limited as they typically cannot enter cells and are inherently unstable in vivo. However, nature uses disulfide bond constrained peptide structures in the form of peptide toxins and knottins to improve proteolytic and thermal stability (Terlau et al. (2004), Physiol. Rev. 84: 41-68; Daly et al. (2011), Curr. Opin. Chem. Biol. 15: 362-368; Clark et al. (2010), Angewandte Chemie, 49: 6545-6548). These highly constrained peptides leverage the fact that proteases can only recognize and break down unfolded peptides. This concept was extended with the development of peptides "stapled" into an alpha-helical shape using optimized cross-linking chemistry, mimicking the structure found at the interface of many protein-protein interactions (Walensky et al. (2004), Science 305: 1466-1470). The resulting molecules possess improved biological properties such as cell penetration (Verdine et al. (2012), Methods in Enzymology, Protein Engineering for Therapeutics, Academic Press: 3-30). However, limitations have hindered their use as therapeutics. These include moderate cell potencies in the high nM to low uM range resulting in high doses required for efficacy, which combined with the hydrophobic nature of their interaction surfaces, produces sub-optimal physicochemical properties such as solubility.

Irreversible inhibitors that covalently bind to their target protein have been described in the art (Singh et al. (2011), Nature Rev. Drug Discovery 10: 307-317; Barf and Kaptein, (2012), J. Med. Chem. 55: 6243-6262). Covalent irreversible inhibitors of drug targets have a number of important advantages over their reversible counterparts as therapeutics. Prolonged suppression of the drug targets may be necessary for maximum pharmacodynamic effect and an irreversible inhibitor can provide this advantage by permanently eliminating existing drug target activity, which will return only when new target protein is synthesized. When an irreversible inhibitor is administered the therapeutic plasma concentration of the irreversible inhibitor would need to be attained only long enough to briefly expose the target protein to the inhibitor, which would irreversibly suppress activity of the target and plasma levels could then rapidly decline while the target protein would remain inactivated. This irreversible binding has the potential advantage of lowering the minimal blood plasma concentration at which therapeutic activity occurs, minimizing multiple dosing requirements and eliminating the requirement for long plasma half-lives without compromising efficacy. All of these considerations could reduce toxicity due to any nonspecific off-target interactions that may occur at high or prolonged blood plasma levels. Irreversible inhibitors also likely have advantages in overcoming drug resistance requirements in two ways. First irreversible inhibitors eliminate the requirement for long blood plasma half-lives without compromising efficacy. Second, while resistance mutations can compromise non-covalent binding and reduce non-covalent affinity, it is still possible to inactivate the target through irreversible inhibition. Peptidomimetic macrocyclic irreversible inhibitors have several important advantages relative to stapled peptides. First, not having the necessity for long plasma half-lives is particularly advantageous since in the design of stapled peptides optimizing for proteolytic stability to prolong half-lives is crucial to ensure sufficient plasma coverage of the target protein to elicit a sustained therapeutic response. Second, irreversible inhibitors enhance the potency (measured as the $IC_{50}$ over a fixed time period), which may result in a lower dose of inhibitor required to silence the target protein hence mitigating formulation issues and not exacerbating physicochemical properties such as solubility.

Many reversible inhibitors of proteins are presently known, as are the binding sites in the proteins to which the reversible inhibitors bind. The binding sites of these reversible inhibitors are sometimes populated with amino acids that are capable of covalent modification with suitably reactive ligands. In other instances, amino acids are located near the binding sites of reversible inhibitors that are capable of covalent modification with suitably reactive ligands. Amino acids capable of covalent modification are typically those, which have a heteroatom such as O, S, or N in the side chain such as threonine, cysteine, histidine, serine, tyrosine and lysine. Sulfur is amenable to covalent modification due to the nucleophilicity of sulfur and as such there are numerous examples of ligands that modify cysteine in proteins of interest. Amino acids such as lysine are usually sufficiently unreactive that ligands do not react in vivo with lysine. However, it is known that a hydrogen bond donor amino acid proximal to lysine can enhance the nucleophilicity of the lysine nitrogen by lowering the pKa making it more amenable to react with electrophilic warheads (US Patent Application No: US 2011/0269244 A1). Amino acids with hydrogen donor capability are arginine, threonine, serine, histidine, tyrosine and lysine. In some cases the hydrogen bond donation, either by a side chain or even a main chain amide can, in many cases, enhance the electrophilicity of a warhead. When such a hydrogen bond donor is also positively charged, Coulombic attraction can accelerate the reaction, for example, by stabilizing the formation of an enolate as in the example of an acrylamide. The present invention addresses these limitations in the art by the design of peptidomimetic macrocycles incorporating an amino acid warhead designed to be proximal to a lysine or cysteine amino acid of the target protein to form a covalent bond resulting in irreversible inhibition of the target protein.

BCL2-A1 (BFL-1) (Vogler et al. (2012), Cell Death Diff. 19: 67-74) and MCL-1 are proteins in the B-cell lymphoma 2 (BCL2) target family (Bajwa et al. (2012), Expert Opin. Ther. Patents 22: 37-55) whose anti-apoptotic members have been identified as important cellular oncogenes that not only promote tumorigenesis but also contribute to chemotherapeutic drug resistance. The potential of this target class is highlighted by ABT-263, a BCL2 family inhibitor helix mimetic in multiple combination clinical trials with existing oncology drugs (Tse et al. (2008), Cancer Research 68: 3421-3428). This class of compound shows significant potential but suffers from toxicity (thrombocytopenia) due to inhibition of off-target BCL2 pathways (BCL-XL) (Bajwa et al. (2012), Expert Opin. Ther. Patents 22: 37-55) and the emergence of resistance. There is evidence that overexpression of BCL2-A1 and upregulation of MCL-1 are the primary resistance mechanisms for Abbott's BCL2 clinical inhibitors (Vogler et al. (2009), Blood, 113: 4403-4413; Al-Harbi et al. (2011), Blood, 118: 3579-3590), with studies suggesting that it may be possible to screen for these using biomarkers (Al-Harbi et al. (2011), Blood, 118: 3579-3590). In addition BCL2-A1 protein is overexpressed in a variety of cancer cells, and increased BCL2-A1 expression in advanced tumor stages has been noted in a number of studies (Vogler et al. (2012), Cell Death Diff. 19: 67-74; Piva et al. (2006), J. Clin. Invest. 116: 3171-3182). It has also been shown that BCL2-A1 down regulation sensitizes non-small cell lung cancer (NSCLC) to gemcitabine (Kim et al. (2011), Molecular Cancer, 10: 1-16) while also exhibiting NPM-ALK induced upregulation in anaplastic large cell lymphomas (ALCLs) which can be extrapolated to ALK modulated NSCLC data in the clinic. BCL2A1 was recently identified as a lineage-specific antiapoptopic oncogene that confers resistance to BRAF inhibition (Haq et al. (2013), PNAS, 110: 4321-4326).

SUMMARY OF THE INVENTION

Figure 1A:
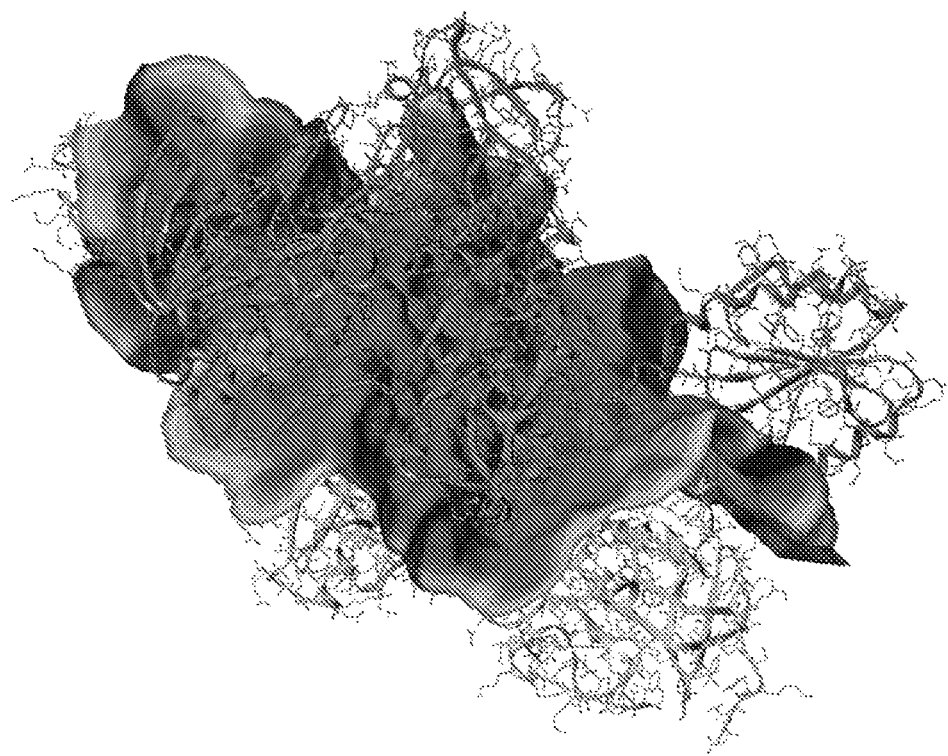
FIG. 1a depicts the protein-protein interface between monomers of thioredoxinreductase homodimer. Protein structure pdb code=3QFA.

In one aspect, the invention relates to an algorithm and method for designing irreversible inhibitors of protein-protein interactions (PPIs) of therapeutic interest. The irreversible inhibitors designed by the algorithm function by forming a covalent bond with a reactive amino acid side chain (reactive side chain) on one of the proteins at the interface of said PPI. Using the invention, it is possible to efficiently design an irreversible peptide inhibitor starting from a known peptide structure fragment excised from the opposing protein of said PPI (template protein) where it is proximal to said target side chain. This approach provides a method to inhibit key therapeutic targets not currently accessible with existing drug design techniques. The algorithm and method include designing modifications to the amino acid side chain of candidate irreversible peptide inhibitor fragments proximal to the target protein reactive side chain (warhead side chain). This is done to promote the formation of a covalent bond between the target polypeptide reactive side chain and the warhead side chain of the candidate peptide inhibitor fragment.

The in silico algorithm and method comprises:

(A) systematically identifying all PPIs within a crystal structure of a target of interest available from, for example, the structures of the protein data bank (PDB—Berman et al. (2000), Nucleic Acids Research, 28: 235-242) or similar structural data repositories;

(B) systematically identifying all surface exposed cysteine residue sulfur(s) and/or lysine residue nitrogen(s) within the interface of a protein identified in (A);

(C) systematically identifying all α-helices, loops with macrocyclization potential, beta sheets or highly buried proximal amino acids in the opposing protein of the interface identified in (A) (peptide inhibitor motif), containing a residue side chain atom less than 15 Å from the cysteine sulfur(s) and/or lysine nitrogen(s) detected in (B) (proximal warhead residue) (Each peptide inhibitor motif is then scored based on its degree of surface burial in the PPI. This is calculated based on the percentage of atoms within 5 Å of the opposing protein (peptide burial));

(D) producing a structural model of the peptide inhibitor motifs determined in (C) where the proximal warhead residue side chain detected in (C) is replaced by a side chain containing a rationally selected warhead able to react with as illustrated below in FIG. 2.

Rational selection as defined in (D) is the creation of a warhead containing structural model using computational chemistry that allows the cysteine or lysine residues identified in (B) to readily assume a conformation that brings the thiol of the cysteine residue side chain or the primary amine group of the lysine residue side chain within bond-forming proximity of the selected warhead. A covalent bond length of less than about 2 angstroms for the bond formed between the said cysteine or lysine and the reactive chemical functionality of the warhead is used to indicate that the candidate inhibitor will covalently bond to the opposing protein interface from which it was derived. This is followed by the rational selection of positions for optimal stapling of the resultant peptide based on the environments of the remaining peptide side chains, or/and the identification of additional modifications to modulate ADME properties. These include but are not limited to the removal of peptide bonds and/or side chain modifications to other residues in the peptide inhibitor motif parent.

Figure 1B:
FIG. 1b depicts a Asn444-Cys458 derived stapled α-helix from one Thioredoxin reductase monomer modeled irreversibly bound to Cys475 in opposing monomer through side chain modification to Glu447. The α-helix is stapled via side chain modifications at Val448 and Phe452.
Figure 1C:
FIG. 1c depicts the modification of BIM BH3 peptide (PDB structure 2VM6) at Trp147 and subsequent irreversible bond formation to BCL2-A1 protein at Cys55.

Approximately 10% of structures in the PDB were found to contain α-helices in protein-protein interactions proximal (as defined in (C) above) to either a lysine or cysteine residue on the opposing protein. The enzyme Thioredoxin Reductase provides an example of a protein-protein interaction contain an α-helix. This enzyme is active as the homodimer (Nguyen et al. (2006), Cancer Letters, 236: 164-174) and contains a large protein-protein interface highlighted in FIG. 1a. The algorithm's automated perception and analysis of said interface finds an α-helix in one monomer (ASN444-Cys458, proximal residues Ala455 and Glu447) proximal to two cysteines in the other monomer (Cys458 and Cys475. Sample stapled inhibitors of both these potential α-helix dimerization inhibitors have been designed as defined in (D). An example stapled α-helix design is shown in FIG. 1b. Another example of a protein-protein interaction that can be inhibited using an α-helix containing amino acid residue proximal to a cysteine residue is BCL2-A1. This is highlighted with the exemplified modification to the BIM-BH3 peptide shown in FIG. 1c.

Additional examples of targets with known biological relevance identified using the algorithm with promising motifs for PPI design are shown in Table 1.

TABLE 1

| Target Protein | Target Residue | Proximal Warhead Residue | PDB file from Which Data Derived |
|---|---|---|---|
| MCL-1 | Cys234 | Trp5 | 2PQK |
| EED | Cys322 | Phe42 | 2QVX |
| Beta-Catenin | Lys292 | Asp9 | 4DJS |
| MDM2 | Lys92 | Leu22 | 3V3B |
| CDK5 | Cys53 | Ile265 | 1H4L |

A more general list of diverse potential targets determined using the algorithm is shown in Table 2. This table contains all α-helices found from an assessment of the PDB PPIs with both a proximal cysteine and at least 75% α-helix peptide burial in the opposing protein. Close protein analogues have been excised by enforcing the requirement that a unique Cysteine residue number be determined for each PPI interaction detected.

TABLE 2

| PDB ID | Key Cysteine residue |
|---|---|
| 3dp7 | CYS10 |
| 1nhw | CYS100 |
| 1q51 | CYS102 |
| 3p5m | CYS104 |
| 2ppy | CYS107 |
| 1sg4 | CYS108 |
| 3ome | CYS109 |
| 2dd4 | CYS111 |
| 3ele | CYS114 |
| 2qyo | CYS115 |
| 3lls | CYS116 |
| 1pjh | CYS117 |
| 1ky5 | CYS1194 |
| 1lnq | CYS121 |
| 3fv9 | CYS122 |
| 1z7a | CYS124 |
| 1zb8 | CYS125 |
| 2rcy | CYS128 |
| 2ka6 | CYS13 |
| 2fy8 | CYS130 |
| 1rf8 | CYS132 |
| 2j5i | CYS133 |
| 2qac | CYS134 |
| 2pbk | CYS138 |
| 3h0g | CYS1406 |
| 2kxp | CYS141 |
| 2wqk | CYS142 |
| 1jq7 | CYS1461 |
| 2khz | CYS15 |
| 3c24 | CYS151 |
| 1aui | CYS153 |
| 3mps | CYS160 |
| 1id4 | CYS161 |
| 3fx3 | CYS163 |
| 2dyu | CYS164 |
| 2pon | CYS167 |
| 1ztp | CYS173 |
| 3g5n | CYS180 |
| 3f3s | CYS182 |
| 2hd0 | CYS184 |

TABLE 2-continued

| PDB ID | Key Cysteine residue |
|---|---|
| 3qk8 | CYS188 |
| 3frw | CYS19 |
| 1d4f | CYS194 |
| 3nj4 | CYS195 |
| 3sll | CYS198 |
| 1hfe | CYS200 |
| 2l9b | CYS202 |
| 3bpj | CYS207 |
| 2i76 | CYS210 |
| 2pv7 | CYS218 |
| 1x9j | CYS227 |
| 3n58 | CYS231 |
| 3d64 | CYS238 |
| 3ond | CYS244 |
| 3b8i | CYS248 |
| 3r4k | CYS249 |
| 2izz | CYS262 |
| 3ebn | CYS265 |
| 3c03 | CYS269 |
| 3kor | CYS27 |
| 2ziz | CYS290 |
| 3g79 | CYS293 |
| 3oq8 | CYS310 |
| 1f61 | CYS314 |
| 3i4e | CYS315 |
| 1igw | CYS318 |
| 3eqx | CYS34 |
| 1qo7 | CYS350 |
| 3b9t | CYS358 |
| 2ii1 | CYS36 |
| 2zya | CYS364 |
| 2w8z | CYS365 |
| 2iyp | CYS366 |
| 2hzs | CYS38 |
| 3ean | CYS382 |
| 1h6v | CYS383 |
| 2i94 | CYS39 |
| 1v29 | CYS42 |
| 2gh5 | CYS423 |
| 2bnx | CYS428 |
| 2jis | CYS44 |
| 2nyd | CYS45 |
| 2wb1 | CYS450 |
| 2b2d | CYS46 |
| 3kow | CYS475 |
| 2okj | CYS483 |
| 3lnl | CYS49 |
| 3ty5 | CYS499 |
| 1ef8 | CYS50 |
| 1nik | CYS505 |
| 3qod | CYS51 |
| 3nrv | CYS52 |
| 2juz | CYS54 |
| 2qma | CYS564 |
| 2dj5 | CYS59 |
| 3qg2 | CYS6 |
| 3myb | CYS63 |
| 3fz6 | CYS64 |
| 1kfu | CYS640 |
| 1hqm | CYS642 |
| 1cfp | CYS68 |
| 3nmw | CYS681 |
| 2iex | CYS71 |
| 1u6r | CYS73 |
| 2dsd | CYS76 |
| 1wkq | CYS80 |
| 1dwk | CYS83 |
| 1xcb | CYS84 |
| 1gtv | CYS85 |
| 1kyw | CYS86 |
| 3p9k | CYS89 |
| 2bw3 | CYS90 |
| 2dsc | CYS91 |
| 3keo | CYS92 |
| 2q08 | CYS93 |
| 1gte | CYS953 |

In one aspect, the present invention provides a peptidomimetic macrocycle comprising an amino acid sequence which is at least about 30-95%, e.g., 40, 50, 60, 70, 80%, 90% or 94% identical to an amino acid sequence identified as binding to the binding site of a target protein. In another aspect, the peptidomimetic macrocycle contains an amino acid warhead designed to be proximal to a Lys or Cys amino acid of the target protein to form a covalent bond resulting in irreversible inhibition of the target protein. In some embodiments, the peptidomimetic macrocycle comprises a helix, such as an α-helix. In other embodiments, the peptidomimetic macrocycle comprises a macrocyclized loop as defined in (c) above. A peptidomimetic macrocycle of the invention may comprise a crosslinker linking the α-positions of at least two amino acids. At least one of said two amino acids may be an α,α-disubstituted amino acid.

In some embodiments, the peptidomimetic macrocycle has the Formula I:

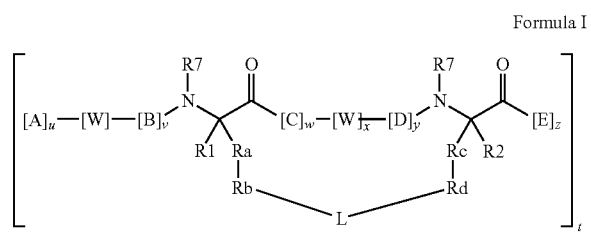

Formula I wherein each A, B, C, and E is independently a natural or non-natural amino acid;

D is a natural, or non-natural amino acid, amino acid analog

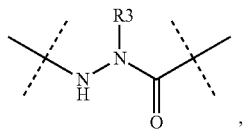

Figure 2:
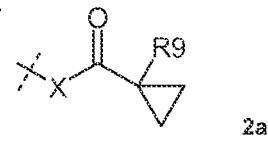
FIG. 2 depicts examples of warhead "moieties" that can be attached to amino acids.
Figure 2:
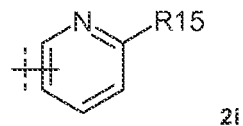
Figure 2:
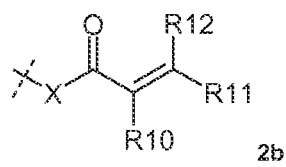
Figure 2:
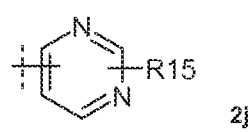
Figure 2:
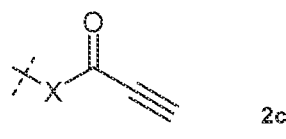
Figure 2:
Figure 2:
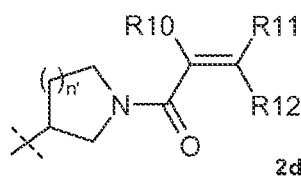
Figure 2:
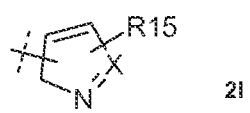
Figure 2:
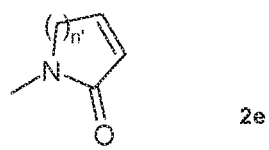
Figure 2:
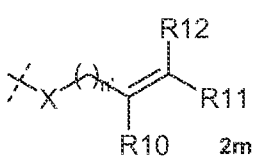
Figure 2:
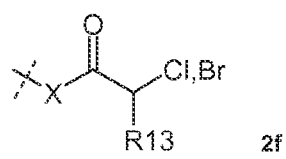
Figure 2:
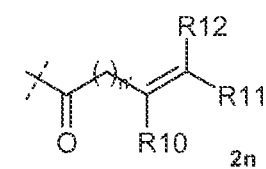
Figure 2:
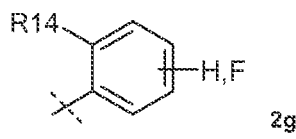
Figure 2:
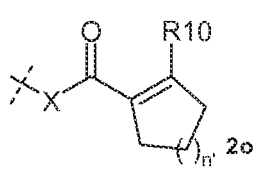
Figure 2:
Figure 2:
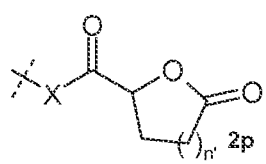

[—NH-L1-CO—], [—NH-L2-SO$_2$—] or [—NH-L3-];

W is a natural or non-natural amino acid or amino acid analog where the amino acid side chain contains a warhead;

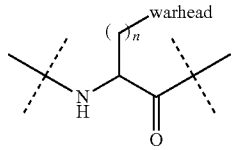

u and z are independently integers from 0-100;
t, v, w, x and y are independently integers from 0-10;
s is 0 or 1;
n is an integer from 1-5;
R$_a$ is (CH$_2$)$_n$, n=0-4, R$_b$ is CH$_2$, and R1 is —H, alkyl, alkenyl, alkynyl, arylalkyl, cycloalkyl, cycloalkylalkyl, heteroalkyl, or heterocycloalkyl, unsubstituted or substituted with halo; or R$_a$ is (CH$_2$)$_n$, n=0-4, R$_b$ is a CH$_2$, R1 is a CH$_2$ and R$_b$ and R1 are covalently bound to form a ring;
R$_c$ is (CH$_2$)$_n$, n=0-4, R$_d$ is CH$_2$, and R2 is —H, alkyl, alkenyl, alkynyl, arylalkyl, cycloalkyl, cycloalkylalkyl, heteroalkyl, or heterocycloalkyl, unsubstituted or substituted with halo; or R$_c$ is (CH$_2$)$_n$, n=0-4, R$_d$ is a CH$_2$, R2 is a CH$_2$ and R$_d$ and R2 are covalently bound to form a ring;

L is a macrocycle-forming linker of the formula -L1-L2-L3-;

L1, L2 and L3 are independently a bond, alkylene, alkenylene, alkynylene, heteroalkylene, cycloalkylene, heterocycloalkylene, cycloarylene, heterocycloarylene, or [—R4-K—R4-]$_p$, each being optionally substituted with R5, and p is an integer from 1 to 5;

R3 is hydrogen, alkyl, alkenyl, alkynyl, arylalkyl, heteroalkyl, cycloalkyl, heterocycloalkyl, cycloalkylalkyl, cycloaryl or heterocycloaryl, optionally substituted with R5;

each K is independently O, S, SO, SO$_2$, CO, CO$_2$, or CONR3;

each R4 is independently alkylene, alkenylene, alkynylene, heteroalkylene, cycloalkylene, heterocycloalkylene, arylene, or heteroarylene;

each R5 is independently halogen, alkyl, —OR6, —N(R6)$_2$, —SR6, —SOR6, —SO$_2$R6, —CO$_2$R6, a fluorescent moiety, a radioisotope or a therapeutic agent;

each R6 is independently —H, alkyl, alkenyl, alkynyl, arylalkyl, cycloalkylalkyl, heterocycloalkyl, a fluorescent moiety, a radioisotope or a therapeutic agent;

R7 is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R4, or part of a cyclic structure with an A residue;

R8 is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R4, or part of a cyclic structure with an E residue;

"warheads" include those disclosed herein, for example by the general structures presented in FIG. 2; 2a, 2b, 2c, 2d, 2e, 2f, 2g, 2h, 2i, 2j, 2k, 2l, 2m, 2n, 2o and 2p, wherein;

X is C, NH, NR8, O or S;
n' is an integer from 0-3;
R9 is hydrogen, CN, or (CO)CH$_3$;
R10 is hydrogen, a bivalent C1-4 saturated or unsaturated, straight or branched, hydrocarbon chain, or an electron-withdrawing group such as F or CF$_3$. In certain embodiments R10 is hydrogen, methyl, ethyl, allyl, propyl, isopropyl, butyl or iso-butyl;
R11 and R12 are each independently hydrogen, a bivalent C1-4 saturated or unsaturated, straight or branched, hydrocarbon chain. In certain embodiments R11 and R12 are each independently hydrogen, methyl, ethyl, allyl, propyl, isopropyl, butyl, iso-butyl. In other embodiments R11 and R12 are each independently —N(R6)$_2$, —CH$_2$N(R6)$_2$, —CH$_2$CH$_2$N(R6)$_2$, —C(O)N(R6)$_2$, —C(O)OCH$_3$, —CH$_2$C(O)OR6 or —CH$_2$CH$_2$C(O)OR6;
R13 is hydrogen, a bivalent C1-4 saturated or unsaturated, straight or branched, hydrocarbon chain. In certain embodiments R13 is hydrogen, methyl, ethyl, vinyl, allyl, propyl or butyl;
R14 is an electron-withdrawing group chosen from NO$_2$, CF$_3$ or CN. In certain embodiments R14 is

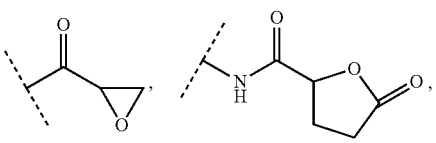

—NHC(O)CHCH$_2$, —NHC(O)CH$_2$Br, —SO$_2$F;

R15 is a halogen, a C$_2$ alkynyl side chain optionally substituted with oxo, halogen, NO$_2$, or CN, or a C$_2$ alkenyl side chain optionally substituted with oxo, halogen, NO$_2$, or CN. In certain embodiments R15 is —CH═CH$_2$ or —C≡CH.

When a bond in a compound formula herein is drawn in a non-stereochemical manner (e.g., flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95% the absolute stereoisomer depicted. In another embodiment, the compound may be at least 99% the absolute stereoisomer depicted.

DETAILED DESCRIPTION OF CERTAIN EMBODIMENTS OF THE INVENTION

As used herein, the term "macrocycle" refers to a molecule having a chemical structure including a ring or cycle formed by at least 9 covalently bonded atoms.

As used herein, the term "peptidomimetic macrocycle" or "crosslinked polypeptide" refers to a compound comprising a plurality of amino acid residues joined by a plurality of peptide bonds and at least one macrocycle-forming linker which forms a macrocycle between a first naturally-occurring or non-naturally-occurring amino acid residue (or analog) and a second naturally-occurring or non-naturally-occurring amino acid residue (or analog) within the same molecule. Peptidomimetic macrocycles include embodiments where the macrocycle-forming linker connects the α carbon of the first amino acid residue (or analog) to the α carbon of the second amino acid residue (or analog). The peptidomimetic macrocycles optionally include one or more non-peptide bonds between one or more amino acid residues and/or amino acid analog residues, and optionally include one or more non-naturally-occurring amino acid residues or amino acid analog residues in addition to any which form the macrocycle. A "corresponding uncrosslinked polypeptide" when referred to in the context of a peptidomimetic macrocycle is understood to relate to a polypeptide of the same length as the macrocycle and comprising the equivalent natural amino acids of the wild-type sequence corresponding to the macrocycle.

As used herein, the term "stability" refers to the maintenance of a defined secondary or tertiary structure in solution by a peptidomimetic macrocycle of the invention as measured by circular dichroism, NMR or another biophysical measure, or resistance to proteolytic degradation in vitro or in vivo. Non-limiting examples of secondary structures contemplated in this invention are helices, β-turns, and β-pleated sheets. Tertiary structures contemplated in this invention are the structural motifs constrained through macrocyclization of the macrocyclic loop structures defined above. In general the term "helix" or "helical" is used to refer to any type of helical structure, including 3$_{10}$-helices, α-helices and π-helices.

As used herein, the term "helical stability" refers to the maintenance of helical structure by a peptidomimetic macrocycle of the invention as measured by circular dichroism or NMR. For example, in some embodiments, the peptidomimetic macrocycles of the invention exhibit at least a 1.25, 1.5, 1.75 or 2-fold increase in helicity as determined by circular dichroism compared to a corresponding uncrosslinked macrocycle.

The term "α-amino acid" or simply "amino acid" refers to a molecule containing both an amino group and a carboxyl group bound to a carbon, which is designated the α-carbon. Suitable amino acids include, without limitation, both the D- and L-isomers of the naturally-occurring amino acids, as well as non-naturally occurring amino acids prepared by organic synthesis or other metabolic routes. Unless the context specifically indicates otherwise, the term amino acid, as used herein, is intended to include amino acid analogs.

The term "naturally occurring amino acid" comprises the residues of the natural amino acids (e.g. Ala, Arg, Asn, Asp, Cys, Glu, Gln, Gly, His, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a (C$_1$-C$_6$)alkyl, phenyl or benzyl ester or amide; or as an α-methylbenzyl amide). Other suitable amino and carboxy protecting groups are known to those skilled in the art (See for example, T. W. Greene, *Protecting Groups In Organic Synthesis*; Wiley: New York, 1981, and references cited therein).

The term "amino acid analog" or "non-natural amino acid" refers to a molecule which is structurally similar to an amino acid and which can be substituted for an amino acid in the formation of a peptidomimetic macrocycle. Amino acid analogs include, without limitation, compounds which are structurally identical to an amino acid, as defined herein, except for the inclusion of one or more additional methylene groups between the amino and carboxyl group (e.g., (α-amino β-carboxy acids), or for the substitution of the amino or carboxy group by a similarly reactive group (e.g., substitution of the primary amine with a secondary or tertiary amine, or substitution or the carboxy group with an ester). Amino acid analogs also include, without limitation, compounds which are structurally identical to an amino acid, as defined herein, except for the inclusion of a warhead on the side chain, which allows for ligand-directed covalent modification of Cys and Lys-containing proteins.

A "non-essential" amino acid residue is a residue that can be altered from the wild-type sequence of a polypeptide (e.g., a BH3 domain of the BCL2-A1 binding domain) without abolishing or substantially altering its essential biological or biochemical activity (e.g., receptor binding or activation). An "essential" amino acid residue is a residue that, when altered from the wild-type sequence of the polypeptide, results in abolishing or substantially abolishing the polypeptide's essential biological or biochemical activity.

A "conservative amino acid substitution" is one in which the amino acid residue is replaced with an amino acid residue having a similar side chain. Families of amino acid residues having similar side chains have been defined in the art. These families include amino acids with basic side chains (e.g., Lys, Arg, His), acidic side chains (e.g., Asp, Glu), uncharged polar side chains (e.g., Gly, Asn, Gln, Ser, Thr, Tyr, Cys), nonpolar side chains (e.g., Ala, Val, Leu, Ile, Pro, Phe, Met, Trp), beta-branched side chains (e.g., Thr, Val, Ile) and aromatic side chains (e.g., Phe, Trp, His). Thus, a predicted nonessential amino acid residue in a polypeptide, for example, is preferably replaced with another amino acid residue from the same side chain family. Other examples of acceptable substitutions are substitutions based on isosteric considerations (e.g. norleucine for methionine) or other properties (e.g. 2-thienylalanine for phenylalanine).

The term "member" as used herein in conjunction with macrocycles or macrocycle-forming linkers refers to the atoms that form or can form the macrocycle, and excludes substituent or side chain atoms. By analogy, cyclodecane, 1,2-difluoro-decane and 1,3-difluoro-decane are all considered ten-membered macrocycles as the hydrogen or fluoro substituents or methyl side chains do not participate in forming the macrocycle.

The term "amino acid side chain" refers to a moiety attached to the α-carbon in an amino acid. For example, the amino acid side chain for alanine is methyl, the amino acid side chain for phenylalanine is phenylmethyl, the amino acid side chain for cysteine is thiomethyl, the amino acid side chain for aspartate is guanidinylpropyl, the amino acid side chain for tyrosine is 4-hydroxyphenylmethyl, etc. Other non-naturally occurring amino acid side chains containing warheads are also included, for example, α,β, unsaturated esters, α,β, unsaturated amides, α,β, unsaturated sulfonamides, thiolactones, β-amino epoxides, substituted cyclopropyl amides, β-halo amides, and the like.

The term "α,α di-substituted amino" acid refers to a molecule or moiety containing both an amino group and a carboxyl group bound to a carbon (the α-carbon) that is attached to two natural or non-natural amino acid side chains.

The term "polypeptide" encompasses two or more naturally or non-naturally-occurring amino acids joined by a covalent bond (e.g., an amide bond). Polypeptides as described herein include full length proteins (e.g., fully processed proteins) as well as shorter amino acid sequences (e.g., fragments of naturally-occurring proteins or synthetic polypeptide fragments). The term "macrocyclization reagent" or "macrocycle-forming reagent" as used herein refers to any reagent which may be used to prepare a peptidomimetic macrocycle of the invention by mediating the reaction between two reactive groups. Reactive groups may be, for example, an azide and alkyne, in which case macrocyclization reagents include, without limitation, Cu reagents such as reagents which provide a reactive Cu(I) species, such as CuBr, CuI or CuOTf, as well as Cu(II) salts such as $Cu(CO_2CH_3)_2$, $CuSO_4$, and $CuCl_2$ that can be converted in situ to an active Cu(I) reagent by the addition of a reducing agent such as ascorbic acid or sodium ascorbate. Macrocyclization reagents may additionally include, for example, Ru reagents known in the art such as Cp*RuCl (PPh$_3$)$_2$, [Cp*RuCl]$_4$ or other Ru reagents which may provide a reactive Ru(II) species. In other cases, the reactive groups are terminal olefins. In such embodiments, the macrocyclization reagents or macrocycle-forming reagents are metathesis catalysts including, but not limited to, stabilized, late transition metal carbene complex catalysts such as Group VIII transition metal carbene catalysts. For example, such catalysts are Ru and Os metal centers having a +2 oxidation state, an electron count of 16 and pentacoordinated. Additional catalysts are disclosed in Grubbs et al., "Ring Closing Metathesis and Related Processes in Organic Synthesis" Acc. Chem. Res. 1995, 28, 446-452, and U.S. Pat. No. 5,811,515. In yet other cases, the reactive groups are thiol groups. In such embodiments, the macrocyclization reagent is, for example, a linker functionalized with two thiol-reactive groups such as halogen groups.

The term "halo" or "halogen" refers to fluorine, chlorine, bromine or iodine or a radical thereof.

The term "alkyl" refers to a hydrocarbon chain that is a straight chain or branched chain, containing the indicated number of carbon atoms. For example, $C_1$-$C_{10}$ indicates that the group has from 1 to 10 (inclusive) carbon atoms in it. In the absence of any numerical designation, "alkyl" is a chain (straight or branched) having 1 to 20 (inclusive) carbon atoms in it.

The term "alkylene" refers to a divalent alkyl (i.e., —R—).

The term "alkenyl" refers to a hydrocarbon chain that is a straight chain or branched chain having one or more carbon-carbon double bonds. The alkenyl moiety contains the indicated number of carbon atoms. For example, $C_2$-$C_{10}$ indicates that the group has from 2 to 10 (inclusive) carbon atoms in it. The term "lower alkenyl" refers to a $C_2$-$C_6$ alkenyl chain. In the absence of any numerical designation, "alkenyl" is a chain (straight or branched) having 2 to 20 (inclusive) carbon atoms in it.

The term "alkynyl" refers to a hydrocarbon chain that is a straight chain or branched chain having one or more carbon-carbon triple bonds. The alkynyl moiety contains the indicated number of carbon atoms. For example, $C_2$-$C_{10}$ indicates that the group has from 2 to 10 (inclusive) carbon atoms in it. The term "lower alkynyl" refers to a $C_2$-$C_6$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring are substituted by a substituent. Examples of aryl groups include phenyl, naphthyl and the like.

The term "arylalkyl" or the term "aralkyl" refers to alkyl substituted with an aryl.

The term "arylalkoxy" refers to an alkoxy substituted with aryl.

"Arylalkyl" refers to an aryl group, as defined above, wherein one of the aryl group's hydrogen atoms has been replaced with a $C_1$-$C_5$ alkyl group, as defined above. Representative examples of an arylalkyl group include, but are not limited to, 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-butylphenyl, 3-butylphenyl, 4-butylphenyl, 2-pentylphenyl, 3-pentylphenyl, 4-pentylphenyl, 2-isopropylphenyl, 3-isopropylphenyl, 4-isopropylphenyl, 2-isobutylphenyl, 3-isobutylphenyl, 4-isobutylphenyl, 2-sec-butylphenyl, 3-sec-butylphenyl, 4-sec-butylphenyl, 2-t-butylphenyl, 3-t-butylphenyl and 4-t-butylphenyl.

"Arylamido" refers to an aryl group, as defined above, wherein one of the aryl group's hydrogen atoms has been replaced with one or more —C(O)NH$_2$ groups. Representative examples of an arylamido group include 2-C(O)NH$_2$-phenyl, 3-C(O)NH$_2$-phenyl, 4-C(O)NH$_2$-phenyl, 2-C(O)NH$_2$-pyridyl, 3-C(O)NH$_2$-pyridyl, and 4-C(O)NH$_2$-pyridyl.

"Alkylheterocycle" refers to a C$_1$-C$_5$ alkyl group, as defined above, wherein one of the C$_1$-C$_5$ alkyl group's hydrogen atoms has been replaced with a heterocycle. Representative examples of an alkylheterocycle group include, but are not limited to, —CH$_2$CH$_2$-morpholine, —CH$_2$CH$_2$-piperidine, —CH$_2$CH$_2$CH$_2$-morpholine, and —CH$_2$CH$_2$CH$_2$-imidazole.

"Alkylamido" refers to a C$_1$-C$_5$ alkyl group, as defined above, wherein one of the C$_1$-C$_5$ alkyl groups hydrogen atoms has been replaced with a —C(O)NH$_2$ group. Representative examples of an alkylamido group include, but are not limited to, —CH$_2$C(O)NH$_2$, CH$_2$CH$_2$C(O)NH$_2$, —CH$_2$CH$_2$CH$_2$C(O)NH$_2$, —CH$_2$CH$_2$CH$_2$CH$_2$C(O)NH$_2$, —CH$_2$CH$_2$CH$_2$CH$_2$CH$_2$C(O)NH$_2$, —CH$_2$CH(C(O)NH)CH$_3$, —CH$_2$CH(C(O)NH)CH$_2$CH$_3$, —CH(C(O)NH)CH$_2$CH$_3$, —C(CH$_3$)$_2$CH$_2$C(O)NH$_2$, —CH$_2$CH$_2$NHC(O)CH$_3$, —CH$_2$CH$_2$NHC(O)CH$_2$CH$_3$, and —CH$_2$CH$_2$NHC(O)CH=CH$_2$.

"Alkanol" refers to a C$_1$-C$_5$ alkyl group, as defined above, wherein one of the C$_1$-C$_5$ alkyl group's hydrogen atoms has been replaced with a hydroxyl group. Representative examples of an alkanol group include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH(OH)CH$_3$, —CH$_2$CH(OH)CH$_2$CH$_3$, —CH(OH)CH$_3$ and —C(CH$_3$)$_2$CH$_2$OH.

"Alkylcarboxy" refers to a C$_1$-C$_5$ alkyl group, as defined above, wherein one of the C$_1$-C$_5$ alkyl group's hydrogen atoms has been replaced with a —COOH group. Representative examples of an alkylcarboxy group include, but are not limited to, —CH$_2$COOH, —CH$_2$CH$_2$COOH, —CH$_2$CH$_2$CH$_2$COOH, —CH$_2$CH$_2$CH$_2$CH$_2$COOH, —CH$_2$CH(COOH)CH$_3$, —CH$_2$CH$_2$CH$_2$CH$_2$CH$_2$COOH, —CH$_2$CH(COOH)CH$_2$CH$_3$, —CH(COOH)CH$_2$CH$_3$ and —C(CH$_3$)$_2$CH$_2$COOH.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally is optionally substituted. Some cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2, 3, or 4 atoms of each ring are substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of O, N, or S if monocyclic, bicyclic, or tricyclic, respectively), wherein 0, 1, 2 or 3 atoms of each ring are substituted by a substituent. Examples of heterocyclyl groups include piperazinyl, pyrrolidinyl, dioxanyl, morpholinyl, tetrahydrofuranyl, and the like.

The term "substituent" refers to a group replacing a second atom or group such as a hydrogen atom on any molecule, compound or moiety. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

In some embodiments, the compounds of this invention contain one or more asymmetric centers and thus occur as racemates and racemic mixtures, single enantiomers, individual diastereomers and diastereomeric mixtures. All such isomeric forms of these compounds are included in the present invention unless expressly provided otherwise. In some embodiments, the compounds of this invention are also represented in multiple tautomeric forms, in such instances, the invention includes all tautomeric forms of the compounds described herein (e.g., if alkylation of a ring system results in alkylation at multiple sites, the invention includes all such reaction products). All such isomeric forms of such compounds are included in the present invention unless expressly provided otherwise. All crystal forms of the compounds described herein are included in the present invention unless expressly provided otherwise.

As used herein, the terms "increase" and "decrease" mean, respectively, to cause a statistically significantly (i.e., $p<0.1$) increase or decrease of at least 5%.

As used herein, the recitation of a numerical range for a variable is intended to convey that the invention may be practiced with the variable equal to any of the values within that range. Thus, for a variable which is inherently discrete, the variable is equal to any integer value within the numerical range, including the end-points of the range. Similarly, for a variable which is inherently continuous, the variable is equal to any real value within the numerical range, including the end-points of the range. As an example, and without limitation, a variable which is described as having values between 0 and 2 takes the values 0, 1 or 2 if the variable is inherently discrete, and takes the values 0.0, 0.1, 0.01, 0.001, or any other real values >0 and <2 if the variable is inherently continuous.

As used herein, unless specifically indicated otherwise, the word "or" is used in the inclusive sense of "and/or" and not the exclusive sense of "either/or."

The term "biological activity" encompasses structural and functional properties of a macrocycle of the invention. Biological activity is, for example, structural stability, alpha-helicity, affinity for a target, resistance to proteolytic degradation, cell penetrability, intracellular stability, in vivo stability, or any combination thereof.

As used herein, "covalent bond" and "valence bond" refer to a chemical bond between two atoms created by the sharing of electrons, usually in pairs, by the bonded atoms.

As used herein, "non-covalent bond" refers to an interaction between atoms and/or molecules that does not involve the formation of a covalent bond between them.

As used herein an "irreversible inhibitor" is a compound that covalently binds a target polypeptide through a covalent bond and inhibits the activity of the target polypeptide for a period of time that is longer than the functional life of the protein. Irreversible inhibitors usually are characterized by time dependency, i.e. the degree of inhibition of the target polypeptide increases until activity is eradicated, with the time that the target polypeptide is in contact with the irreversible inhibitor. Recovery of target polypeptide activity when inhibited by an irreversible inhibitor is dependent upon new protein synthesis. Target polypeptide activity that is inhibited by an irreversible inhibitor remains substantially inhibited in a "wash out" study. Suitable methods for determining if a compound is an irreversible inhibitor are well-known in the art. For example, irreversible inhibition can be identified or confirmed using kinetic analysis (e.g., competitive, uncompetitive, non-competitive) of the inhibition profile of the compound with the target polypeptide, the use of mass spectrometry of the protein drug target modified in the presence of the inhibitor compound, discontinuous exposure, also known as "washout" studies, and the use of labeling, such as radiolabelled inhibitor, to show covalent modification of the enzyme, or other methods known to one of skill in the art. In certain preferred embodiments, the target polypeptide has catalytic activity and the irreversible inhibitor forms a covalent bond with a Cys or Lys reside that is not a catalytic residue.

As used herein "stapled silencer peptides" are peptidomimetic macrocyclic inhibitors with sequences excised from protein-protein interaction interface structures containing a warhead amino acid side chain capable of binding irreversibly to the opposing protein of said interface.

As used herein, a "reversible inhibitor" is a compound that reversibly binds a target polypeptide and inhibits the activity of the target polypeptide. A reversible inhibitor may bind its target polypeptide non-covalently or through a mechanism that includes a transient covalent bond. Recovery of target polypeptide activity when inhibited by a reversible inhibitor can occur by dissociation of the reversible inhibitor from the target polypeptide. Target polypeptide activity is recovered when a reversible inhibitor is "Washed out" in a wash out study. Preferred reversible inhibitors are "potent" inhibitors of the activity of their target polypeptides. A "potent" reversible inhibitor inhibits the activity of its target polypeptide with an $IC_{50}$ of about 50 µM or less, about 1 µM or less, about 100 nM or less, or about 1 nM or less, and/or a $K_i$ of about 50 pM or less, about 1 µM or less, about 100 nM or less, or about 1 nM or less.

The terms "$IC_{50}$" and "inhibitory concentration 50" are terms of art that are well-understood to mean the concentration of a molecule that inhibits 50% of the activity of a biological process of interest, including, without limitation, catalytic activity, cell viability, protein translation activity and the like.

The term "$K_i$" and "inhibition constant" are terms of art that are well-understood to be the dissociation constant for the polypeptide (e.g. enzyme)-inhibitor complex.

As used herein, a "warhead" is a chemical group comprising a reactive chemical functionality or functional group and optionally containing a linker moiety. The reactive functional group can form a covalent bond with an amino acid residue such as Cys (i.e., the ~SH group in the Cys side chain), or Lys (i.e. the $NH_2$ group in the Lys side chain) or other amino acid residues capable of being covalently modified that are present in the binding pocket of the target protein thereby irreversibly inhibiting the target polypeptide. It will be appreciated that the W group of Formula I as defined and described herein, provides such warhead groups for covalently, and irreversibly, inhibiting the target protein.

The term "in silico" is a term of art that is understood to refer to methods and processes that are performed on a computer, for example, using computational modeling programs, computational chemistry, molecular graphics, molecular modeling, and the like to produce computer simulations.

As used herein, the term "computational modeling programs" refers to computer software programs that deal with the visualization and engineering of proteins and small molecules including but not limited to computational chemistry, chemoinformatics, energy calculations, protein modeling, and the like. Examples of such programs are known to one of ordinary skill in the art, and certain examples are provided herein.

As used herein, the term "sequence alignment" refers to an arrangement of two or more protein or nucleic acid sequences, which allows comparison and highlighting of their similarity (or difference). Methods and computer programs for sequence alignment are well known (e.g., BLAST). Sequences may be padded with gaps (usually denoted by dashes) so that wherever possible columns contain identical or similar characters from the sequences involved.

As used herein, the term "crystal" refers to any three-dimensional ordered array of molecules that diffracts X-rays.

As used herein the terms "atomic co-ordinates" and "structure co-ordinates" refer to mathematical co-ordinates (represented as "X," "Y" and "Z" values) that describe the positions of atoms in a three-dimensional model/structure or experimental structure of a protein.

As used herein, the term "homology modeling" refers to the practice of deriving models for three-dimensional structures of macromolecules from existing three-dimensional structures for their homologues. Homology models are obtained using computer programs that make it possible to alter the identity of residues at positions where the sequence of the molecule of interest is not the same as that of the molecule of known structure.

As used herein, "computational chemistry" refers to calculations of the physical and chemical properties of molecules.

As used herein, "molecular graphics" refers to two or three dimensional representations of atoms preferably on a computer screen.

As used herein, "molecular modeling" refers to methods or procedures that can be performed with or without a computer to make one or more models and, optionally, to make predictions about structure activity relationships of ligands. The methods used in molecular modeling range from molecular graphics to computational chemistry.

The invention relates to algorithms and methods for designing irreversible inhibitors of target polypeptides, such as enzymes. The irreversible inhibitors designed using the invention are part of the invention and are capable of potent and selective inhibition of the target polypeptide. In general the invention is a rational algorithm and design method in which design choices are guided by the structure of the target polypeptide, the structure of a reversible inhibitor of the target polypeptide, and the interaction of the reversible inhibitor with the target polypeptide. Irreversible inhibitors or candidate irreversible inhibitors, designed using the method of the invention, comprise a template or scaffold to which one or more warheads are bonded. The resulting compound has binding affinity for the target polypeptide and once bound, the warhead reacts with a Cys or Lys residue in the binding site of the target polypeptide to form a covalent bond, resulting in irreversible inhibition of the target polypeptide.

The invention provides a method for designing a peptidomimetic macrocycle inhibitor that covalently binds a target polypeptide. The method includes providing a structural model of a reversible peptidomimetic macrocycle inhibitor bound to a binding site in a target polypeptide. The reversible peptidomimetic macrocycle inhibitor makes non-covalent contacts with the binding site. Using the structural model a Cys or Lys residue in the binding site of the target polypeptide that is adjacent to the reversible inhibitor when the reversible peptidomimetic macrocycle inhibitor is bound to the binding site is identified. A single Cys or Lys residue, all Cys or Lys residues or a desired number of Cys or Lys residues that are adjacent to the reversible inhibitor when the reversible peptidomimetic macrocycle inhibitor is bound to the binding site can be identified.

Structural models of one or more candidate peptidomimetic macrocycle inhibitors that are designed to covalently bind the target polypeptide are produced. The candidate peptidomimetic macrocycle inhibitors include a warhead-containing amino acid substitution. For example, the warhead contains a reactive chemical functionality capable or reacting with and forming a covalent bond with the thiol or amino group in the side chain of a Cys or Lys residue respectively, and optionally a linker that positions the reactive chemical functionality within bonding distance of one or more of the identified Cys or Lys residues in the binding site of the target polypeptide. Substitutable positions of the reversible peptidomimetic macrocycle inhibitor that result in the reactive chemical functionality of the warhead being within bonding distance of an identified Cys or Lys residue in the binding site of the target polypeptide when the candidate peptidomimetic macrocycle inhibitor is bound to the binding site are identified. A determination is made of whether a candidate irreversible peptidomimetic macrocycle inhibitor containing a warhead, that is attached to an identified substitutable position and is within bonding distance of an identified Cys or Lys residue in the binding site of the target polypeptide when the candidate inhibitor is bound to the binding site, is likely to be an inhibitor that covalently binds the target polypeptide, and preferably is an irreversible inhibitor of the target polypeptide, by forming a covalent bond between the sulfur or nitrogen atom of the Cys or Lys residue respectively in the binding site and the reactive chemical functionality of the warhead when the candidate inhibitor is bound to the binding site. A covalent bond length less than about 2.1 angstroms, for the bond formed between the sulfur or nitrogen atom of the Cys or Lys residue respectively in the binding site and the reactive chemical functionality of the warhead, indicates that the candidate inhibitor is an inhibitor that covalently binds a target polypeptide.

The method of the invention can be performed using any suitable structural model, such as physical models or preferably molecular graphics. The method can be performed manually or can be automated. Preferably, the method is performed in silico.

As will be apparent from the foregoing and more detailed description that follows conceptually the algorithm and method of the invention comprises A) providing a target and a reversible peptidomimetic macrocycle inhibitor, B) identifying a target Cys or Lys, C) producing structural models of candidate peptidomimetic macrocycle inhibitors that contain a warhead, D) determining proximity of warhead to target Cys or Lys, and E) forming a covalent bond.

Inhibitors of BCL2-A1

In some embodiments, the peptidomimetic macrocycle has the Formula I:

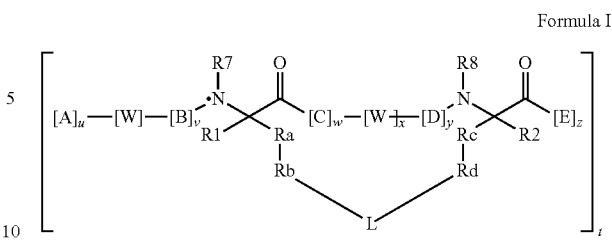

Formula I wherein: each A, B, C and E is independently a natural or non-natural amino acid;

D is a natural, or non-natural amino acid, amino acid analog,

[—NH-L1-CO—], [—NH-L2-SO$_2$—] or [—NH-L3-];

W is a natural or non-natural amino acid or amino acid analog where the amino acid side chain contains a warhead;

u and z are independently integers from 0-100;
t, v, w, x and y are independently integers from 0-10;
s is 0 or 1;
n is an integer from 1-5;
$R_a$ is $(CH_2)_n$, n=0-4, $R_b$ is $CH_2$, and R1 is —H, alkyl, alkenyl, alkynyl, arylalkyl, cycloalkyl, cycloalkylalkyl, heteroalkyl, or heterocycloalkyl, unsubstituted or substituted with halo; or $R_a$ is $(CH_2)_n$, n=0-4, $R_b$ is a $CH_2$, R1 is a $CH_2$ and $R_b$ and R1 are covalently bound to form a ring;
$R_c$ is $(CH_2)_n$, n=0-4, $R_d$ is $CH_2$, and R2 is —H, alkyl, alkenyl, alkynyl, arylalkyl, cycloalkyl, cycloalkylalkyl, heteroalkyl, or heterocycloalkyl, unsubstituted or substituted with halo; or $R_c$ is $(CH_2)_n$, n=0-4, $R_d$ is a $CH_2$, R2 is a $CH_2$ and $R_d$ and R2 are covalently bound to form a ring;
L is a macrocycle-forming linker of the formula -L1-L2-;
L1, L2 and L3 are independently alkylene, alkenylene, alkynylene, heteroalkylene, cycloalkylene, heterocycloalkylene, cycloarylene, heterocycloarylene, or [—R4-K—R4-]$_p$, each being optionally substituted with R5, and p is an integer from 1 to 5;
R3 is hydrogen, alkyl, alkenyl, alkynyl, arylalkyl, heteroalkyl, cycloalkyl, heterocycloalkyl, cycloalkylalkyl, cycloaryl or heterocycloaryl, optionally substituted with R5;
each K is independently O, S, SO, SO$_2$, CO, CO$_2$, or CONR3;
each R4 is independently alkylene, alkenylene, alkynylene, heteroalkylene, cycloalkylene, heterocycloalkylene, arylene, or heteroarylene;
each R5 is independently halogen, alkyl, —OR6, —N(R6)$_2$, —SR6, —SOR6, —SO$_2$R6, —CO$_2$R6, a fluorescent moiety, a radioisotope or a therapeutic agent;

each R6 is independently —H, alkyl, alkenyl, alkynyl, arylalkyl, cycloalkylalkyl, heterocycloalkyl, a fluorescent moiety, a radioisotope or a therapeutic agent;

R7 is —H, alkyl, alkenyl, alkynyl, arylalkyl, cycloalkyl, heteroalkyl, cycloalkylalkyl, heterocyeloalkyl, cycloaryl, or heterocycloaryl, optionally substituted with R4, or part of a cyclic structure with an A residue;

R8 is —H, alkyl, alkenyl, alkynyl, arylalkyl, cycloalkyl, heteroalkyl, eycloalkylalkyl, heterocycloalkyl, cycloaryl, or heterocycloaryl, optionally substituted with R4, or part of a cyclic structure with an E residue;

"warheads" include those disclosed herein, for example by the general structures presented in FIG. 2; 2a, 2b, 2c, 2d, 2e, 2f, 2g, 2h, 2i, 2j, 2k, 2l, 2m, 2n, 2o and 2p, wherein;

X is C, NH, NR8, O or S;

n' is an integer from 0-3;

R9 is hydrogen, CN, or (CO)CH$_3$;

R10 is hydrogen, a bivalent C1-4 saturated or unsaturated, straight or branched, hydrocarbon chain, or an electron-withdrawing group such as F or CF$_3$. In certain embodiments R10 is hydrogen, methyl, ethyl, allyl, propyl, isopropyl, butyl or iso-butyl;

R11 and R12 are each independently, a bivalent C1-4 saturated or unsaturated, straight or branched, hydrocarbon chain. In certain embodiments R11 and R12 are each independently hydrogen, methyl, ethyl, allyl, propyl, isopropyl, butyl, iso-butyl. In other embodiments R11 and R12 are each independently —N(R6)$_2$, —CH$_2$N(R6)$_2$, —CH$_2$CH$_2$N(R6)$_2$, —C(O)N(R6)$_2$, —C(O)OR6, —CH$_2$C(O)OR6 or —CH$_2$CH$_2$C(O)OR6;

R13 is hydrogen, a bivalent C1-4 saturated or unsaturated, straight or branched, hydrocarbon chain. In certain embodiments R13 is hydrogen, methyl, ethyl, vinyl, allyl, propyl or butyl;

R14 is an electron-withdrawing group chosen from NO$_2$, CF$_3$ or CN. In certain embodiments R14 is

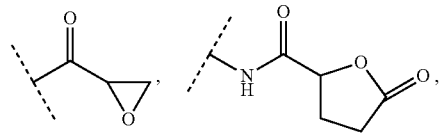

—NHC(O)CHCH$_2$, —NHC(O)CH$_2$Br, —SO$_2$F;

R15 is a halogen, a C$_2$ alkynyl side chain optionally substituted with oxo, halogen, NO$_2$, or CN, or a C$_2$ alkenyl side chain optionally substituted with oxo, halogen, NO$_2$, or CN. In certain embodiments R15 is —CH=CH$_2$ or —C≡CH.

In some embodiments, at least one of R1 and R2 is alkyl, unsubstituted or substituted with halo. In another embodiment, both R1 and R2 are alkyl, unsubstituted or substituted with halo. In some embodiments, at least one of R1 and R2 is methyl. In other embodiments, R1 and R2 are methyl.

In some embodiments of the invention, w+x+y is at least 3. In other embodiments of the invention w+x+y is 1, 2, 3, 4, 5, 6, 7, 8, 9 or 10. Each occurrence of A, B, C, D or E in a macrocycle or macrocycle precursor of the invention is independently selected. For example, a sequence represented by the formula [C]$_w$ when w is 3, encompasses embodiments where the amino acids are not identical, e.g. Gln-Asp-Ala as well as embodiments where the amino acids are identical, e.g. Gln-Gln-Gln. This applies for any value of w, x or y in the indicated ranges.

Similarly, when t is greater than 1, each compound of the invention may encompass peptidomimetic macrocycles which are the same or different. For example, a compound of the invention may comprise peptidomimetic macrocycles comprising different linker lengths or chemical compositions.

In some embodiments, the peptidomimetic macrocycle of the invention comprises a secondary structure which is an α-helix and R8 is —H, allowing intra helical hydrogen bonding. In some embodiments, at least one of A, B, C, D, or E is an α,α-disubstituted amino acid. In one example, B is an α,α-disubstituted amino acid. For instance, at least one of A, B, C, D or E is 2-aminoisobutyric acid.

In other embodiments, at least one of A, B, C, D or E is

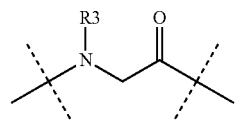

In other embodiments, the length of the macrocycle-forming linker L as measured from a first Cα to a second Cα is selected to stabilize a desired secondary peptide structure, such as an α-helix formed by residues of the peptidomimetic macrocycle including, but not necessarily limited to, those between the first Cα to a second Cα.

In one embodiment, the peptidomimetic macrocycle of Formula (I) is:

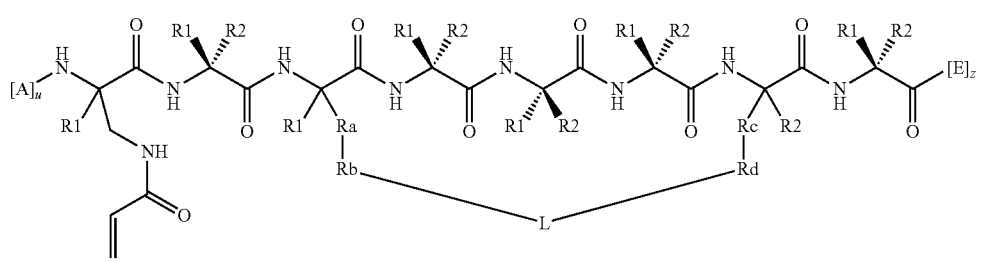

Ia wherein each R1 and R2 is independently H, alkyl, alkenyl, alkynyl, arylalkyl, cycloalkyl, cycloalkylalkyl, heteroalkyl, or heterocycloalkyl, unsubstituted or substituted with halo. In related embodiments, the peptidomimetic macrocycle of Formula (I) is:

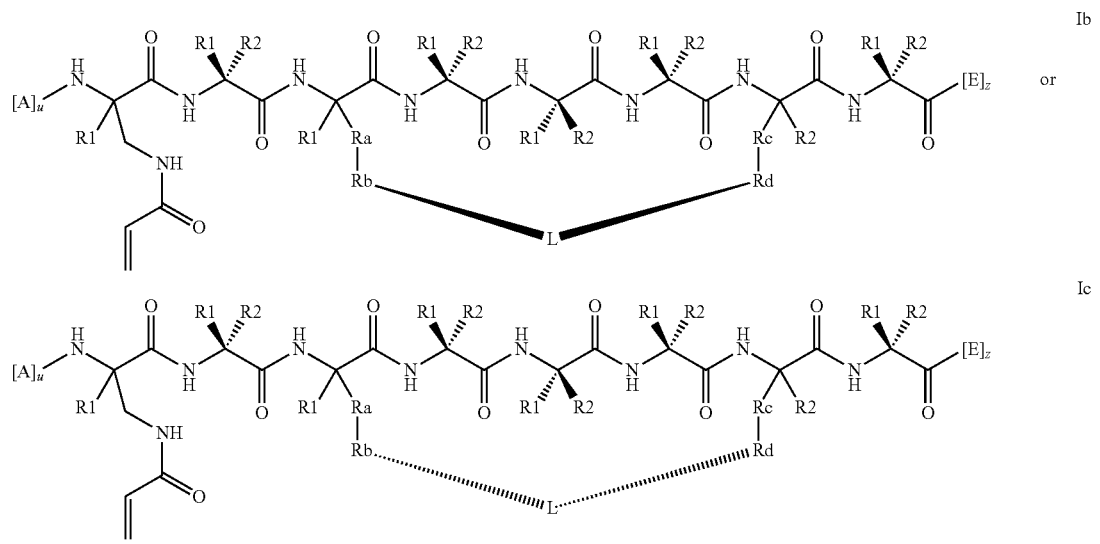
In other embodiments the peptidomimetic macrocycle of Formula (I) is a compound of any of the formulas shown below:

Id  Ie  If
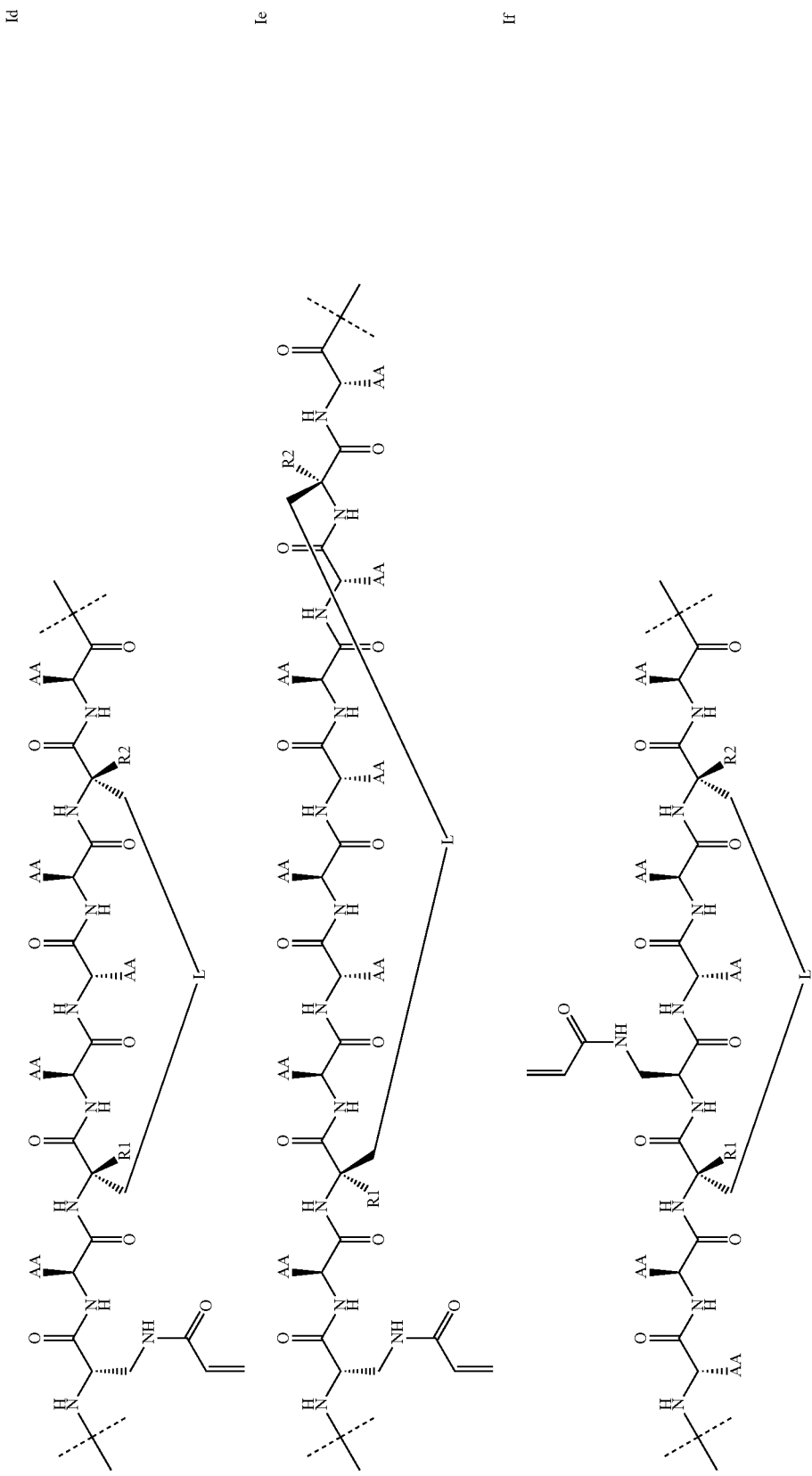

-continued
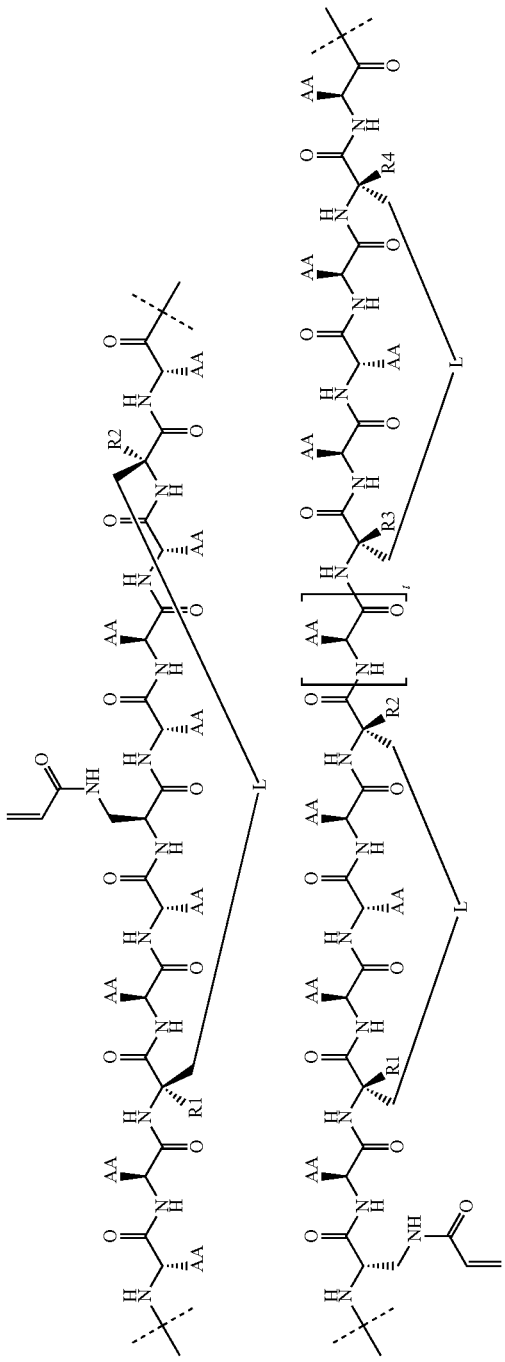
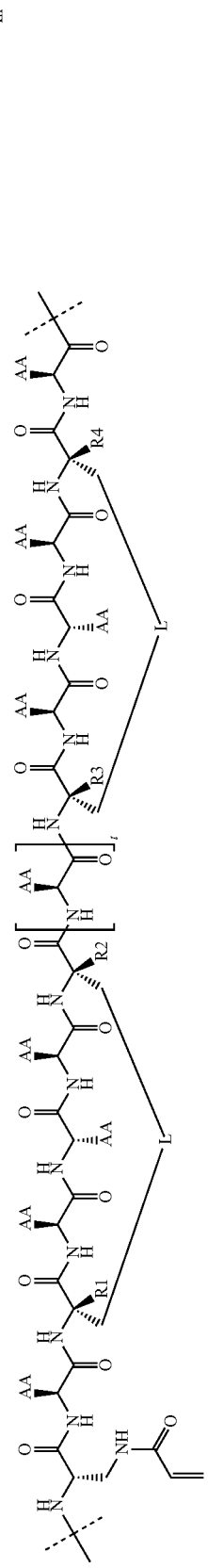
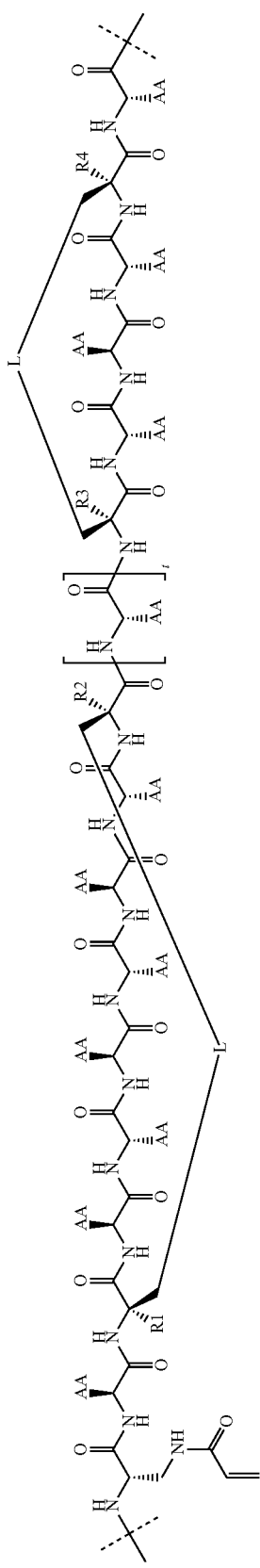
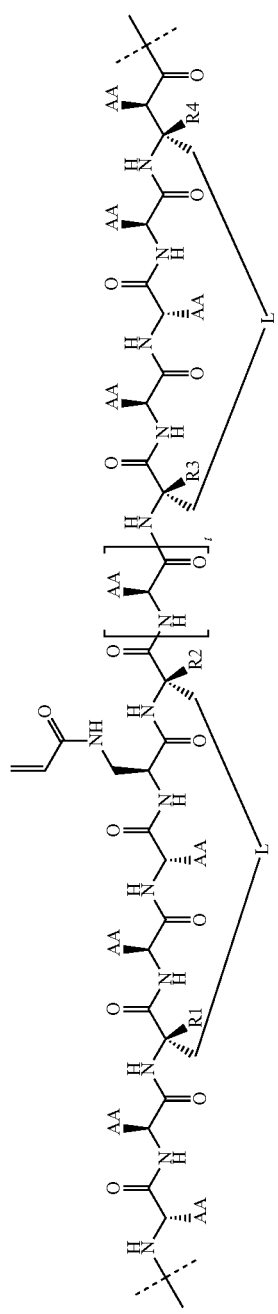

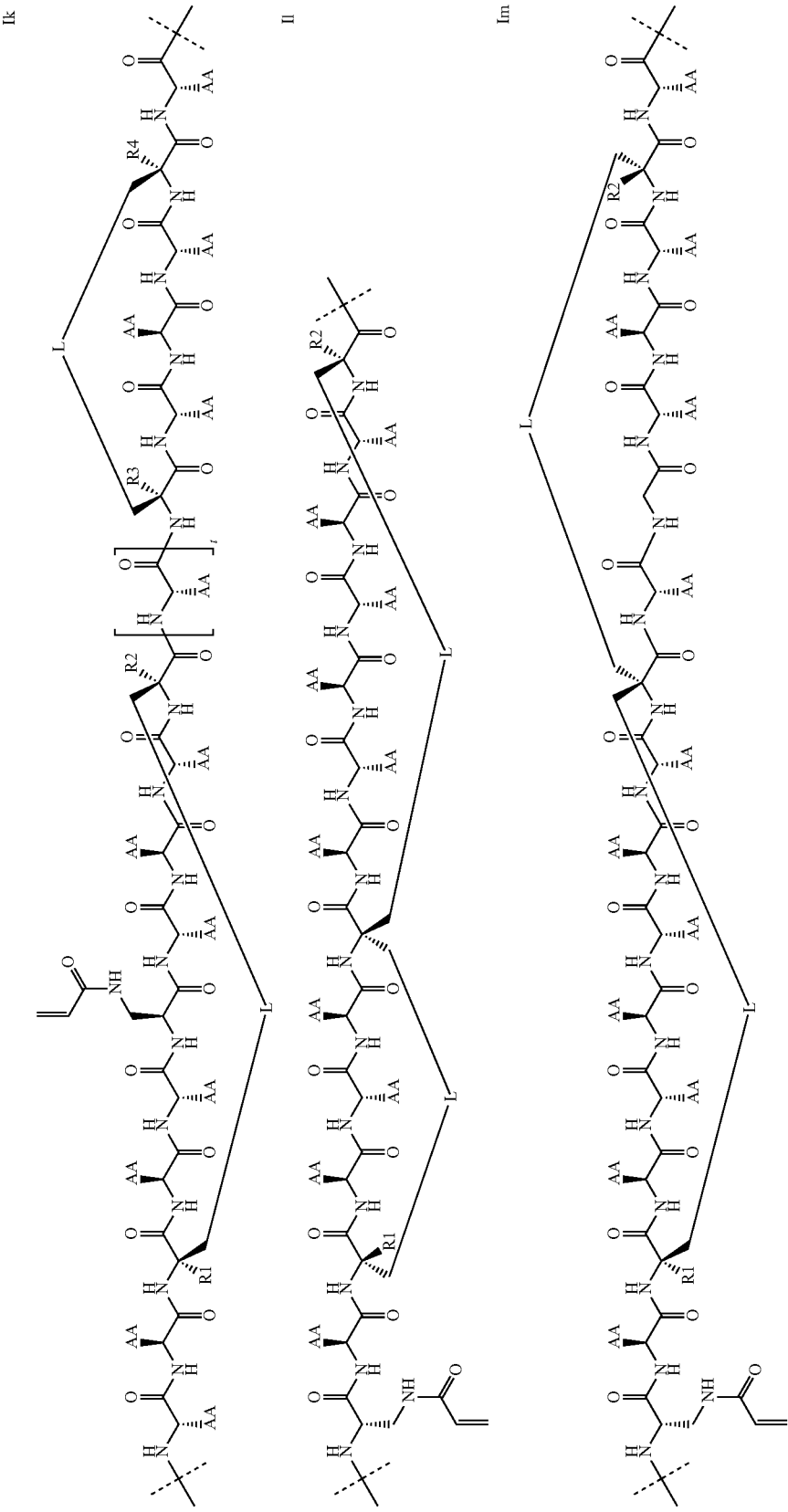

-continued
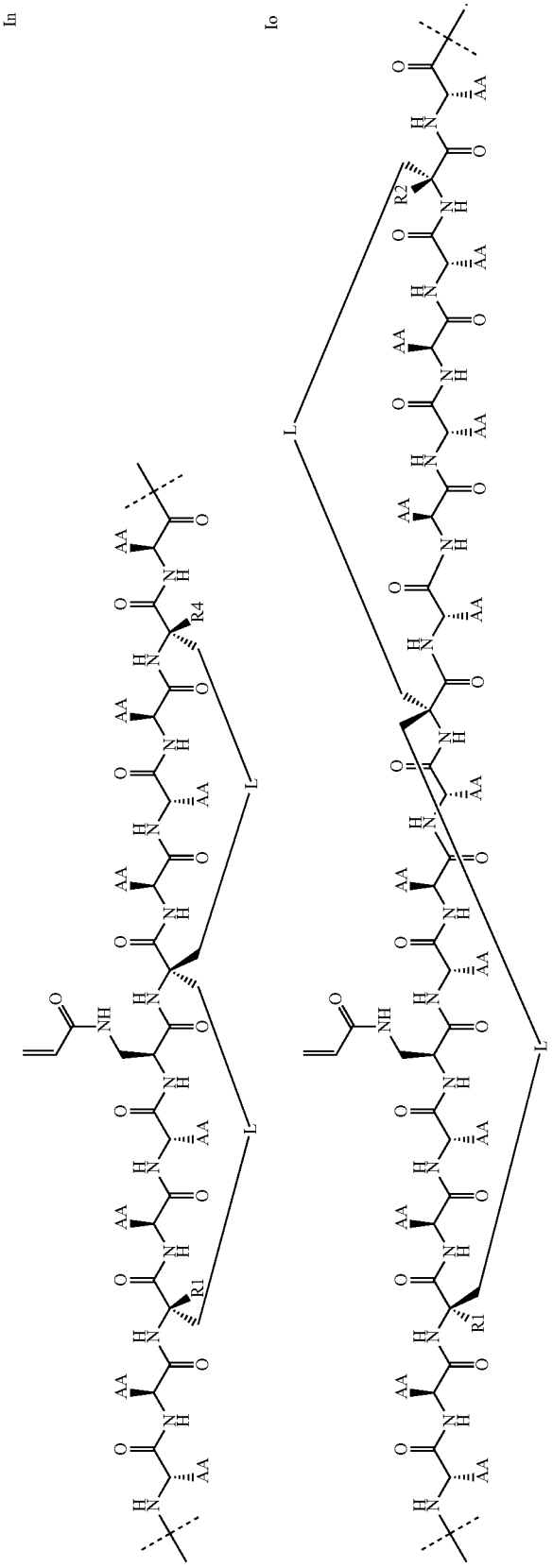

In other embodiments the peptidomimetic macrocycle of Formula (I) is a compound of any of the formulas shown below:

Ip    Iq    Ir
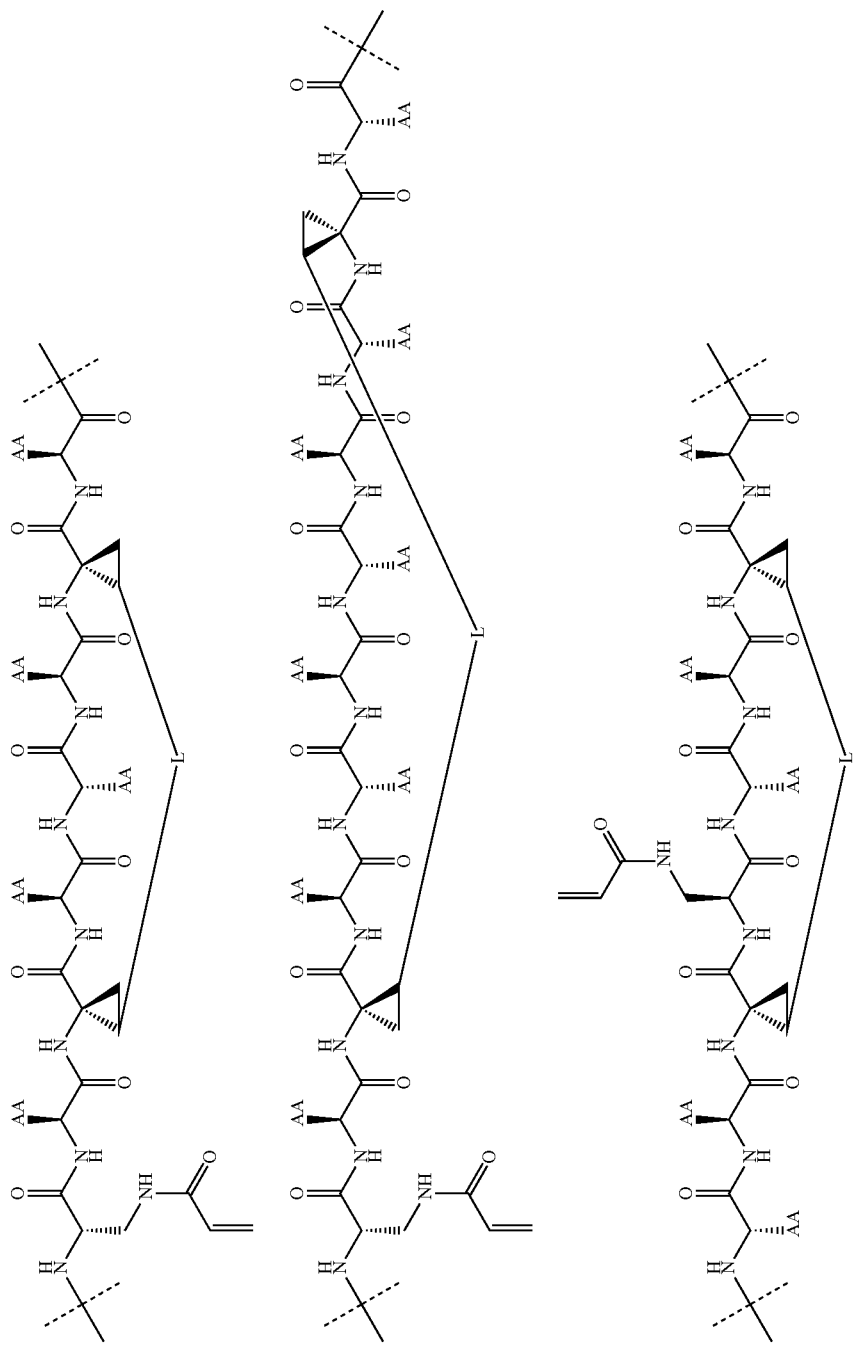

-continued
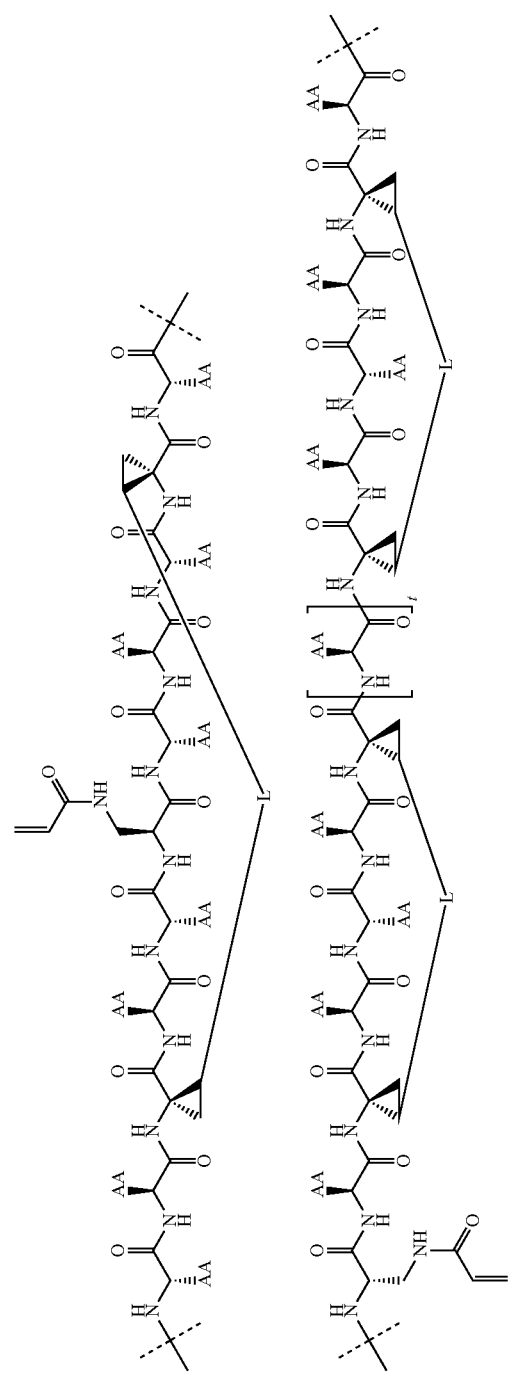
Is
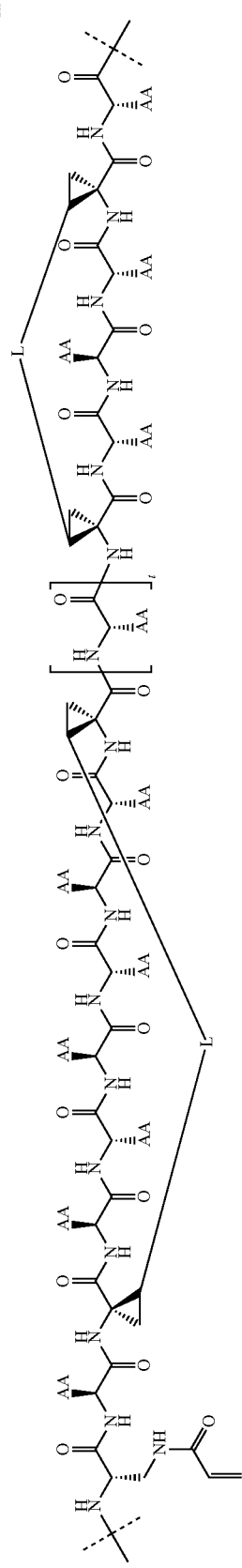
It
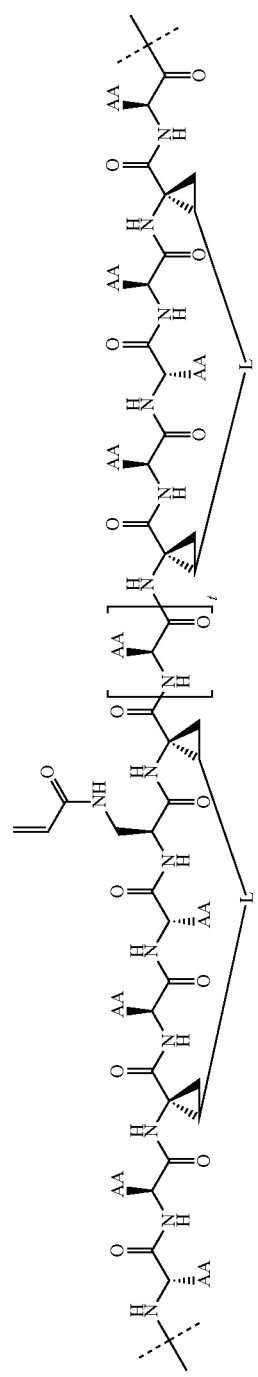
Iu
Iv

-continued
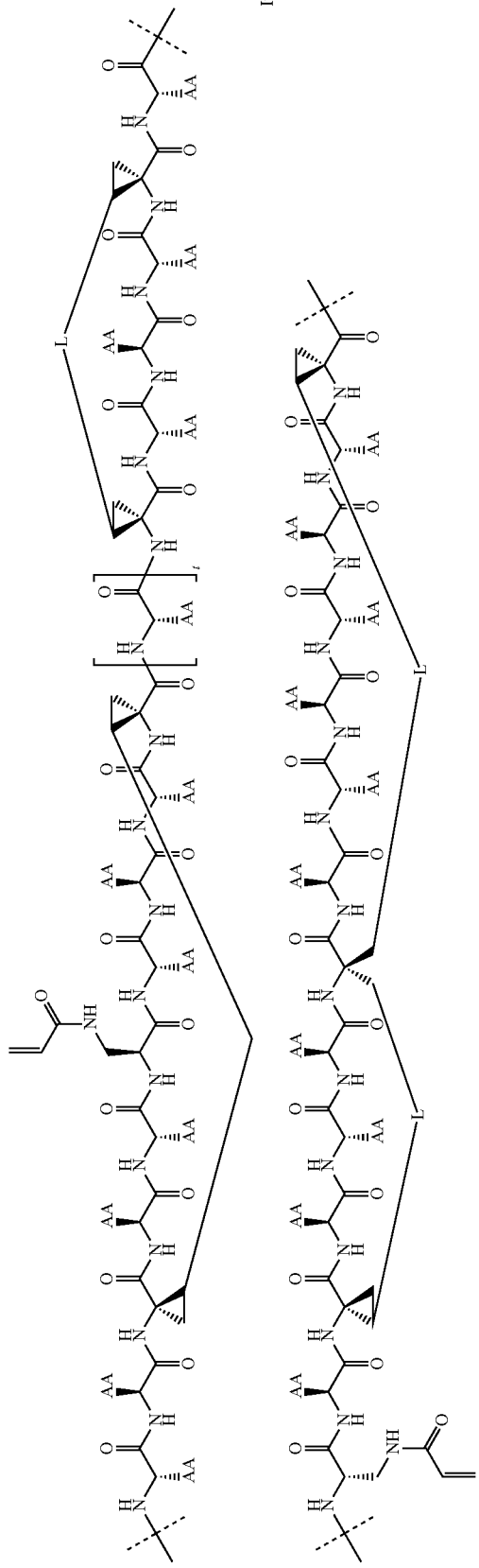
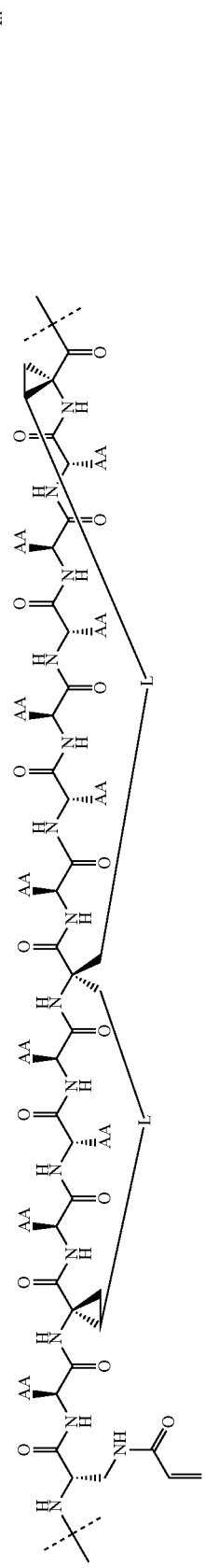
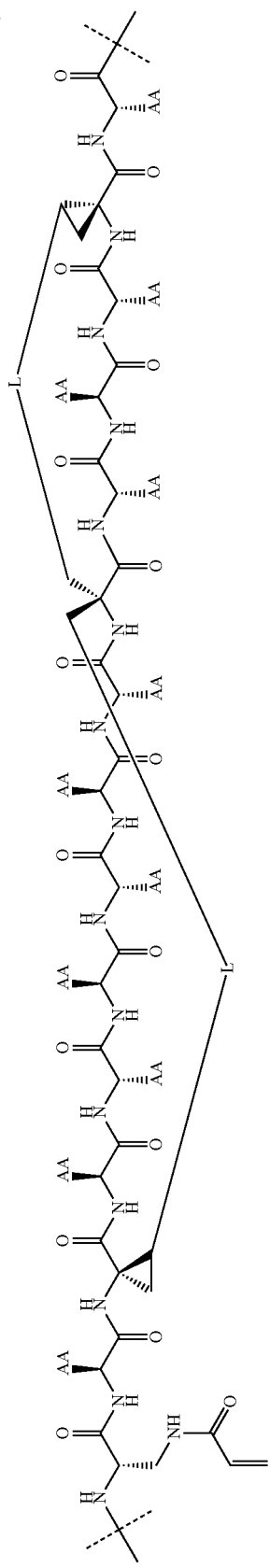

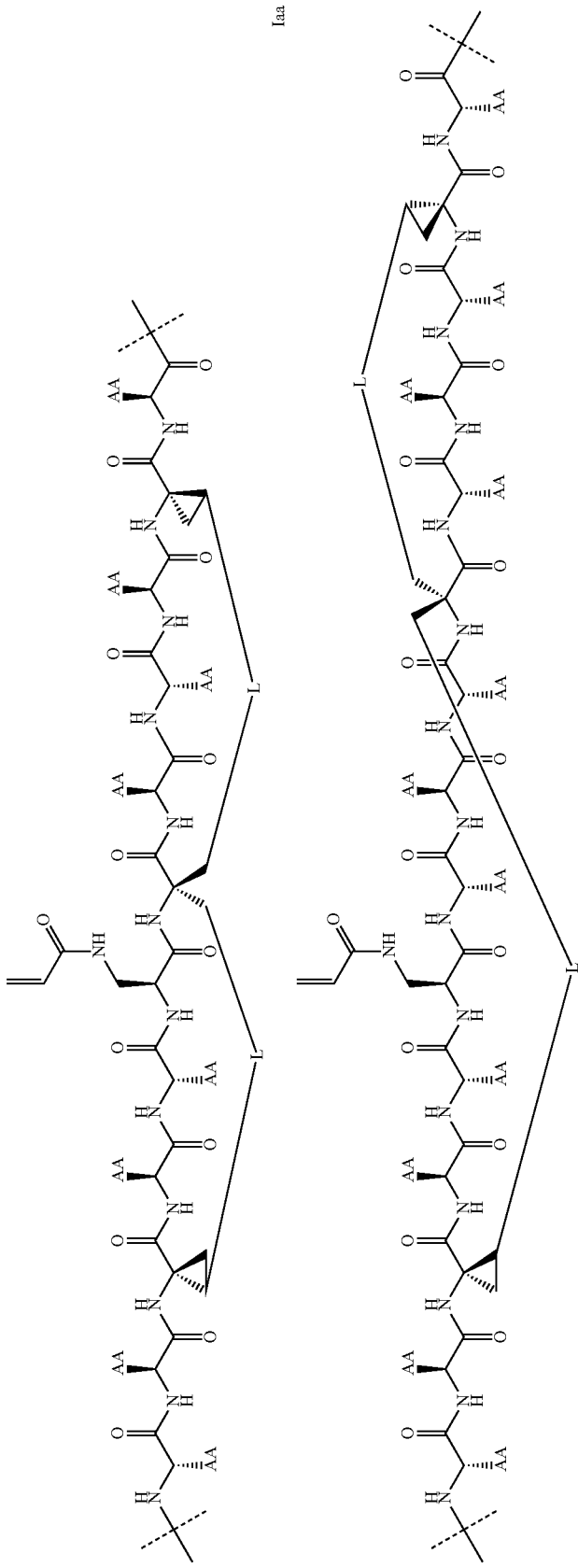

In other embodiments the peptidomimetic macrocycle of Formula (I) is a compound of any of the formulas shown below:

Ibb  Icc  Idd
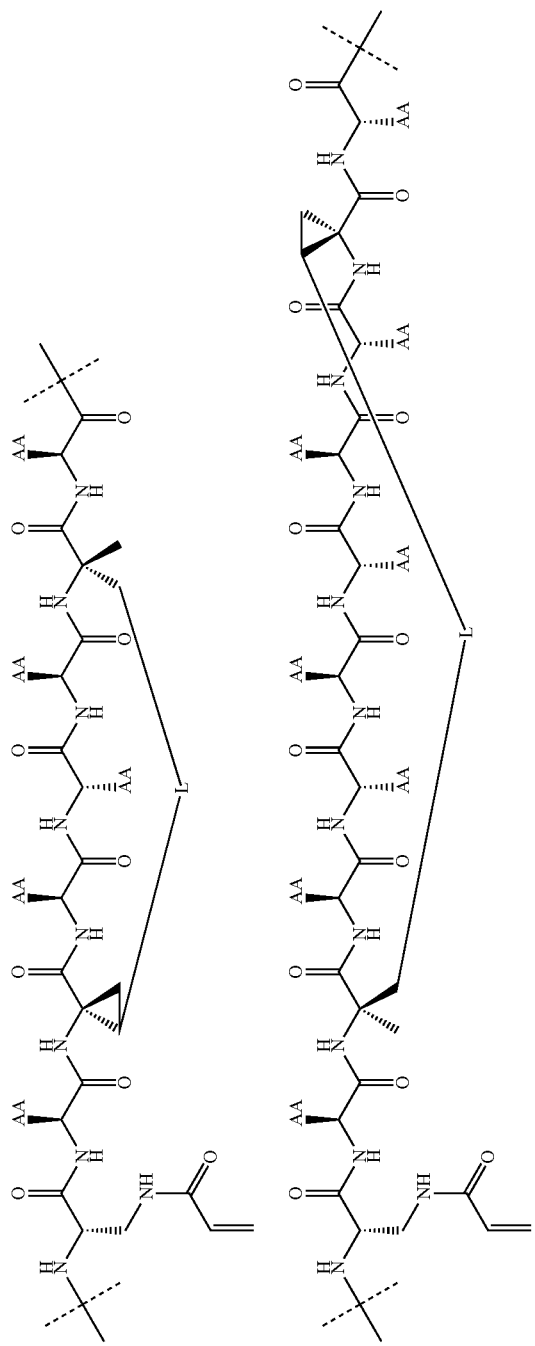

-continued
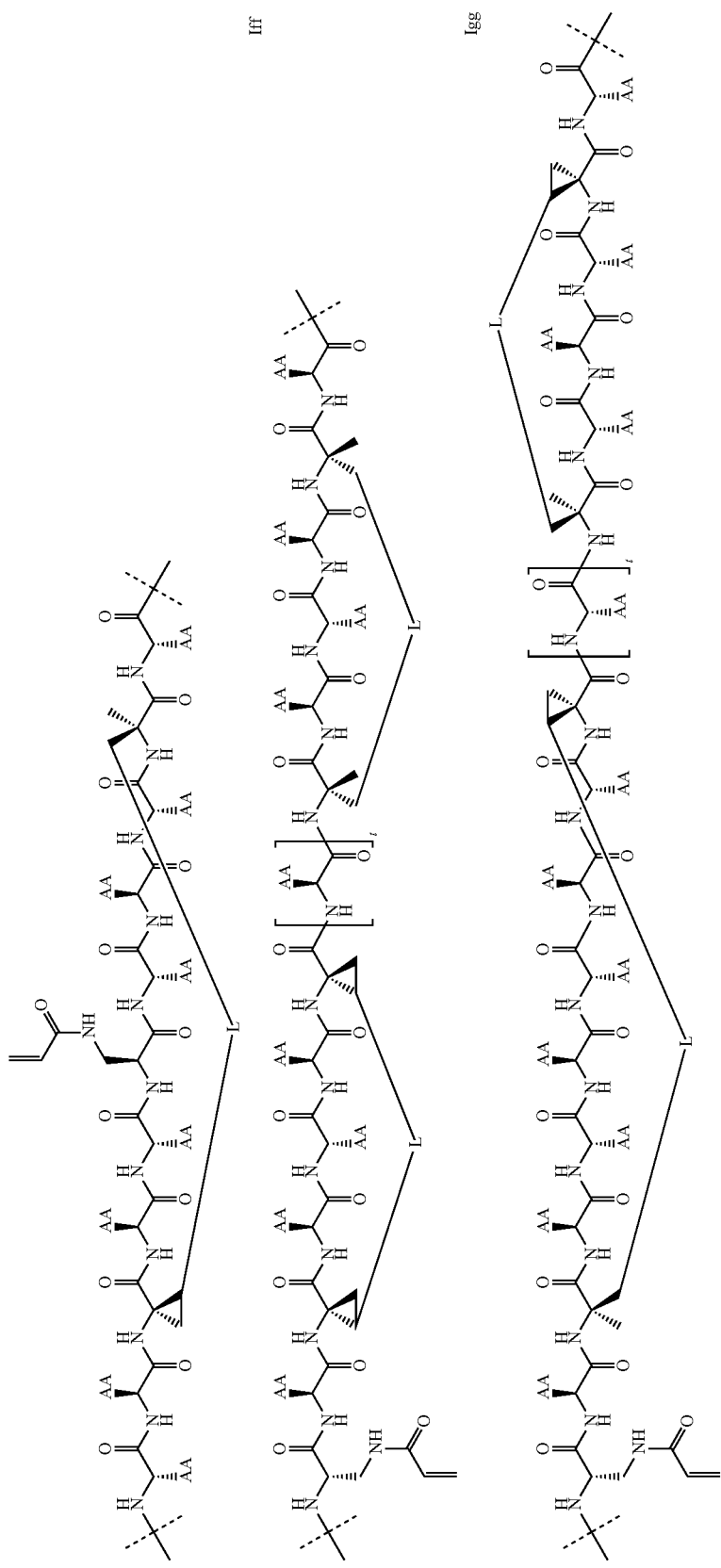

-continued
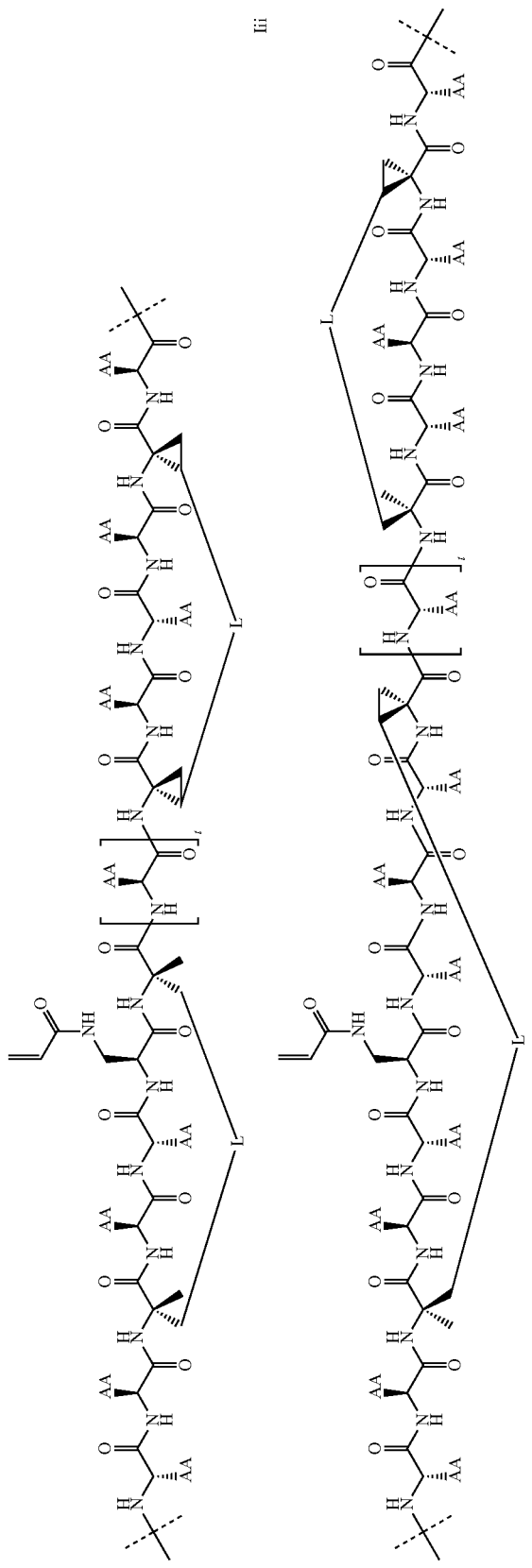

wherein "AA" represents any natural or non-natural amino acid side chain and "╱" is $[A]_u$ and $[E]_z$ as defined above, and t is an integer between 0 and 20, 50 or 100. In some embodiments t is 0. In other embodiments, t is less than 50.

Exemplary embodiments of the macrocycle-forming linker L are shown below.

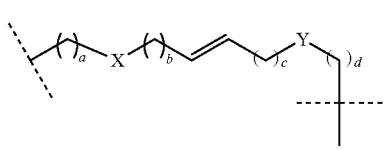
L3 where X, Y = —CH$_2$—, O, S or NH
a, b, c, d = 0-10

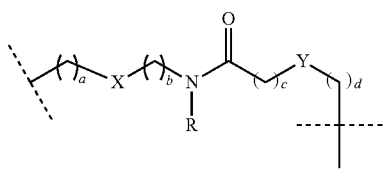
L4 where X, Y = —CH$_2$—, O, S or NH
a, b, c, d = 0-10
R = H, alkyl, other substituent

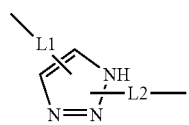
L5

L1 and L2 are independently alkylene, alklylene
or —R4—K—R4— R4 is independently alkylene or alkylene
K is O, S, SO, SO$_2$, CO, CO$_2$ or CONR4

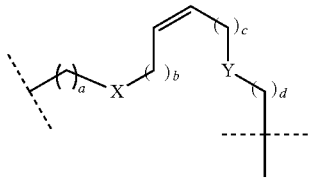
L6 where X, Y = —CH$_2$—, O, S or NH
a, b, c, d = 0-10

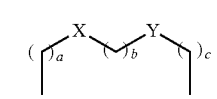
L7 where X, Y = —CH$_2$—, O, S or NH
a, b, c, d = 0-10

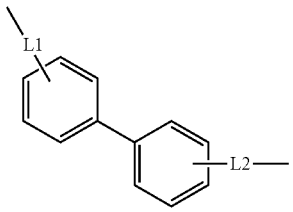
L8

L1 and L2 are independently alkylene, alklylene
or —R4—K—R4— R4 is independently alkylene or alkylene
K is O, S, SO, SO$_2$, CO, CO$_2$ or CONR4

Exemplary embodiments of the peptidomimetic macrocycles of the invention are shown below.

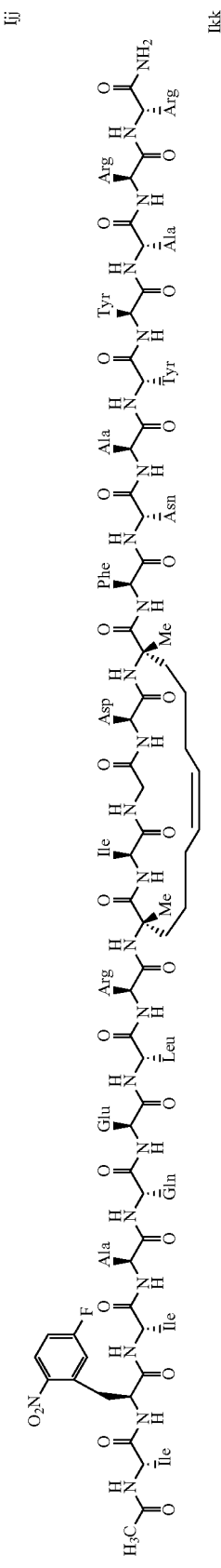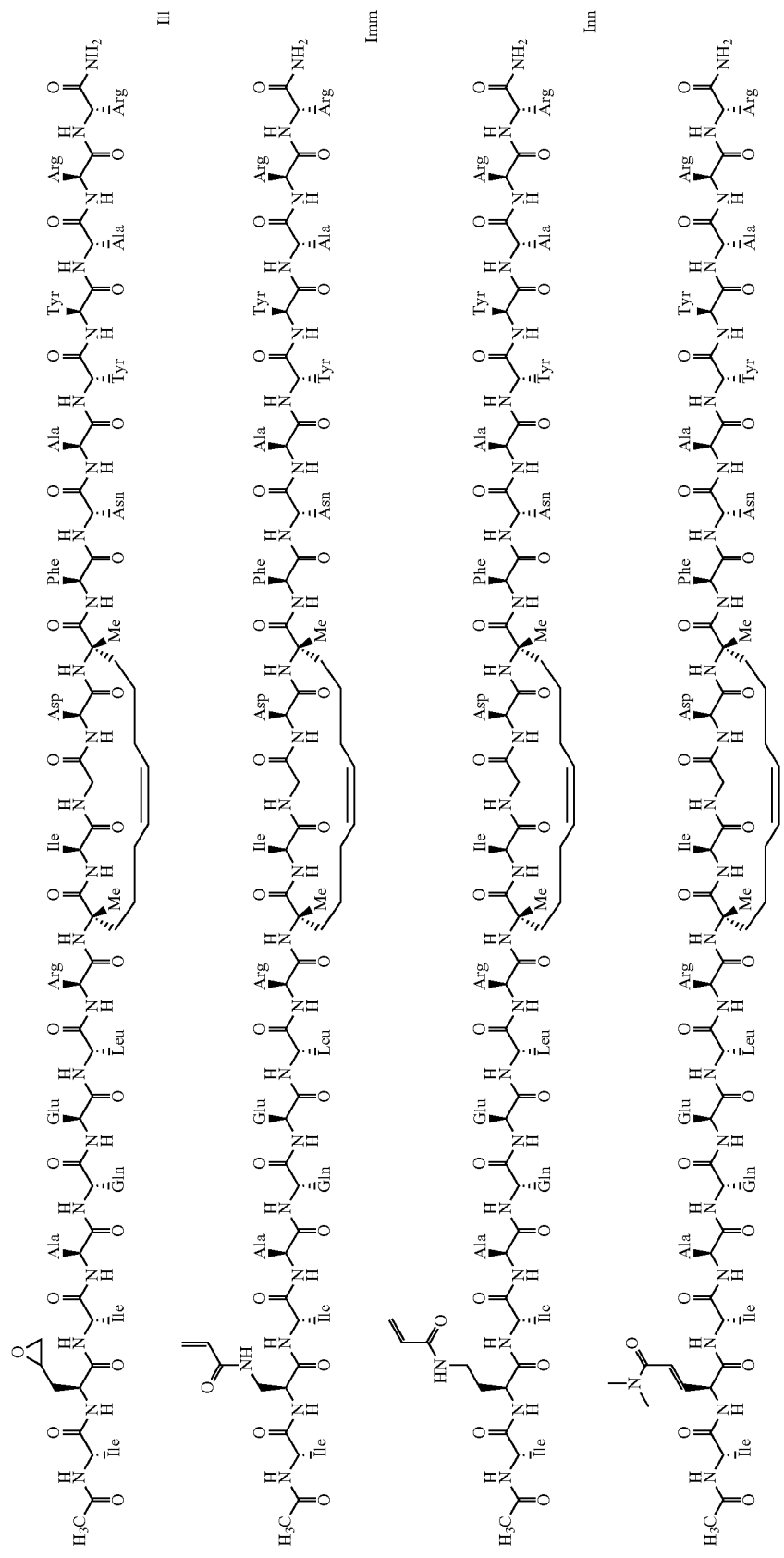

-continued
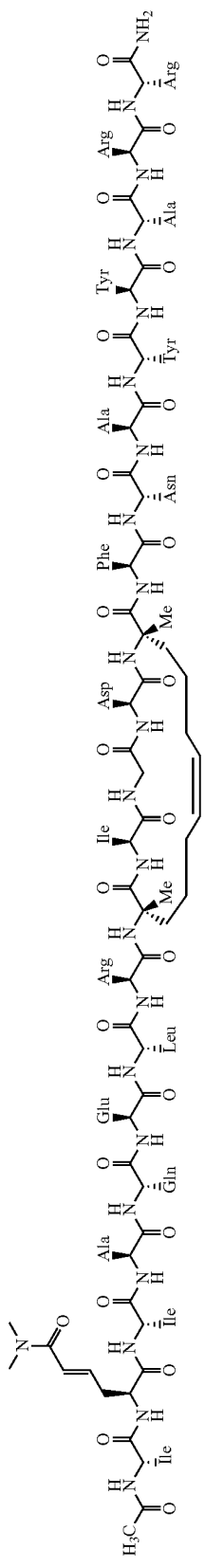
Ioo
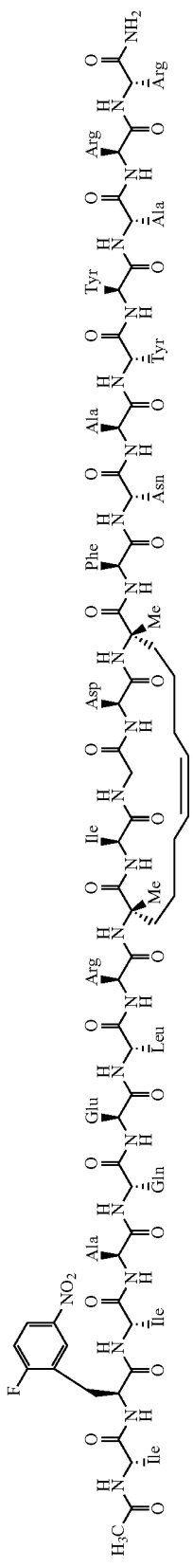
Ipp
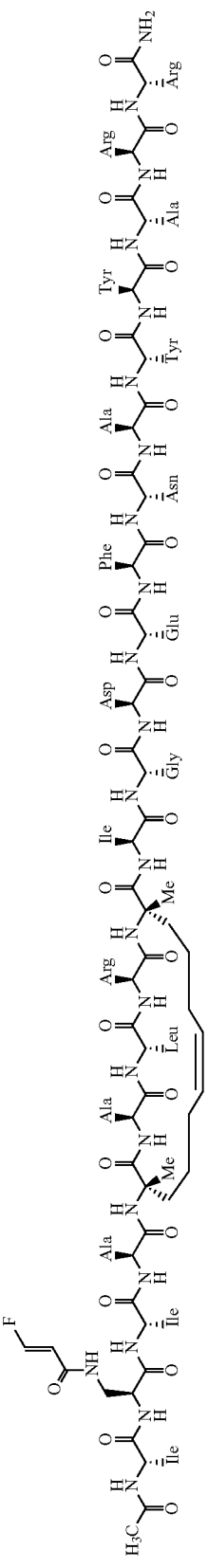
Iqq
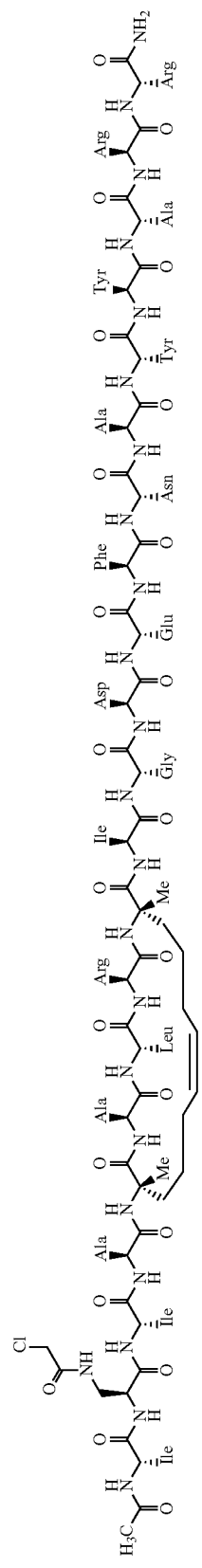
Irr

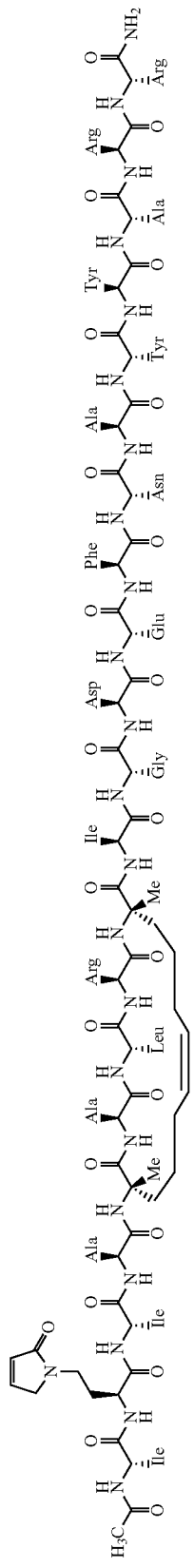
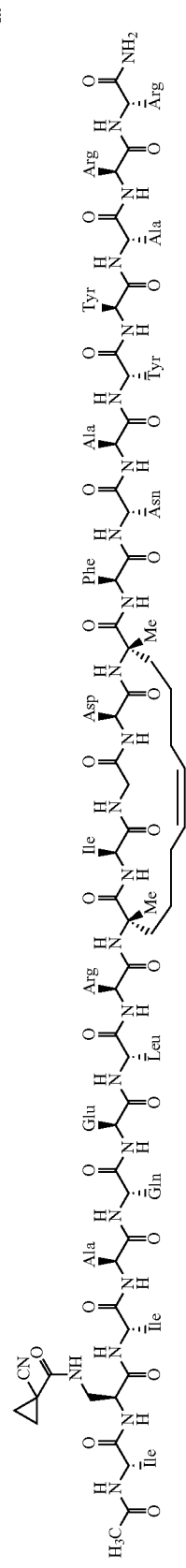
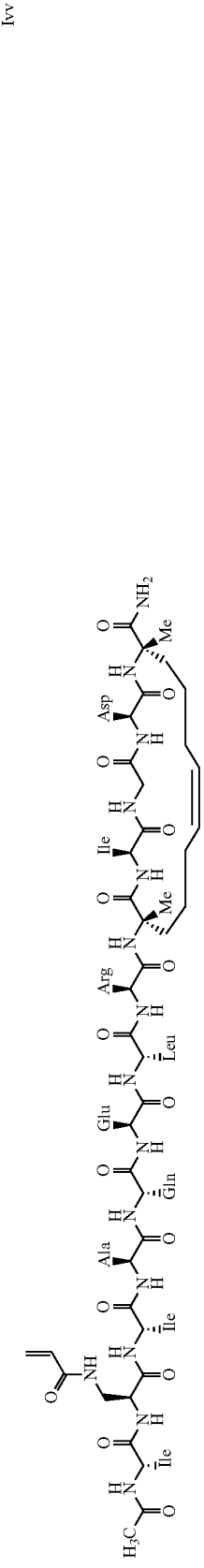
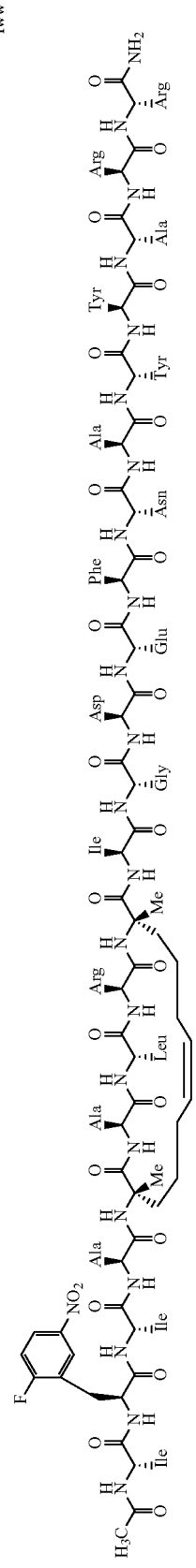

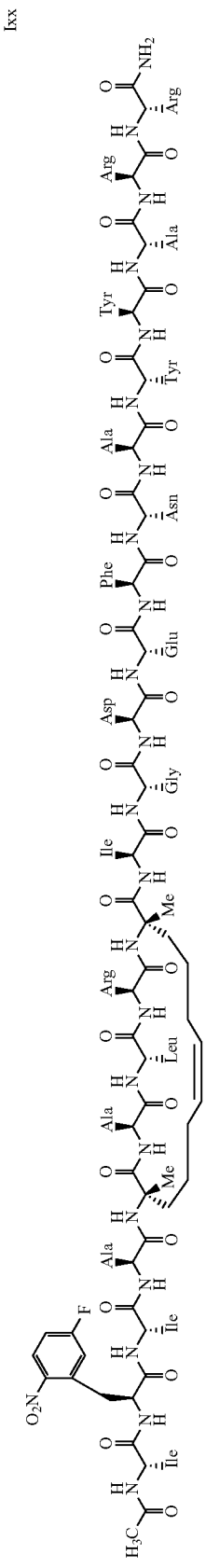
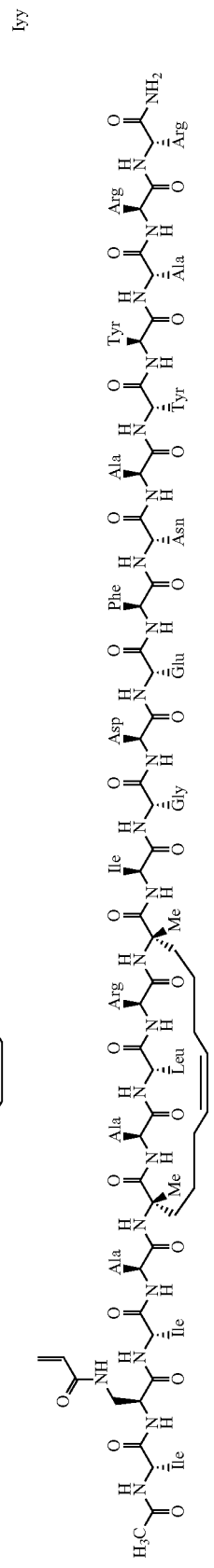
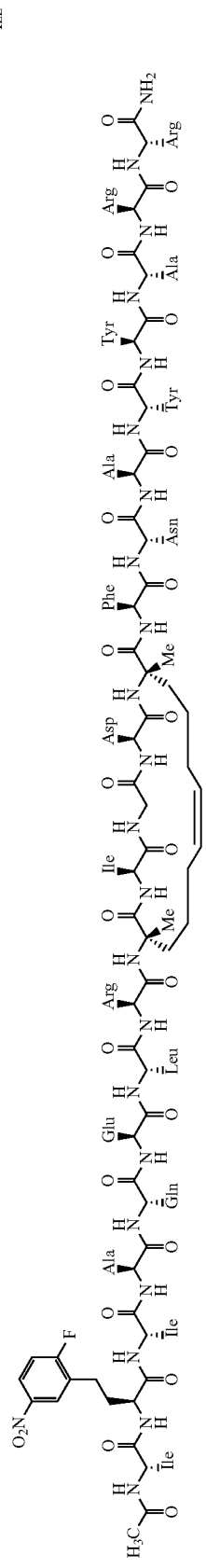
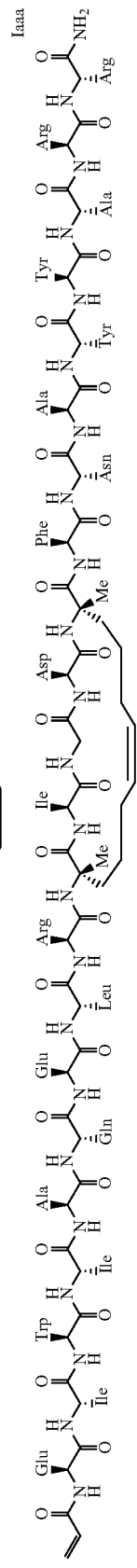
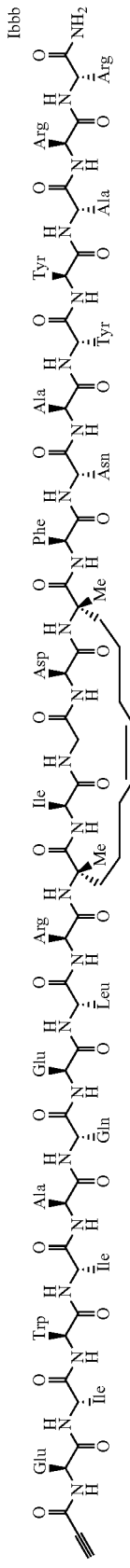
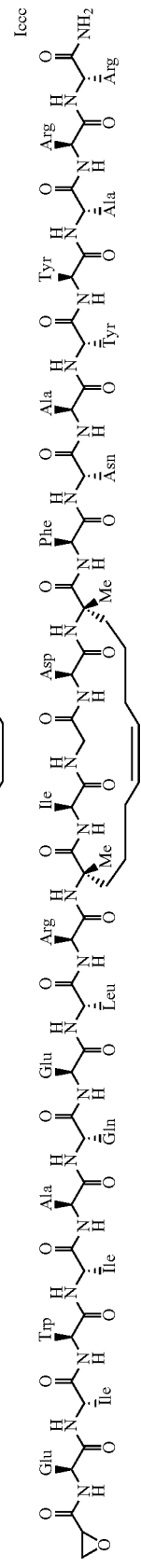

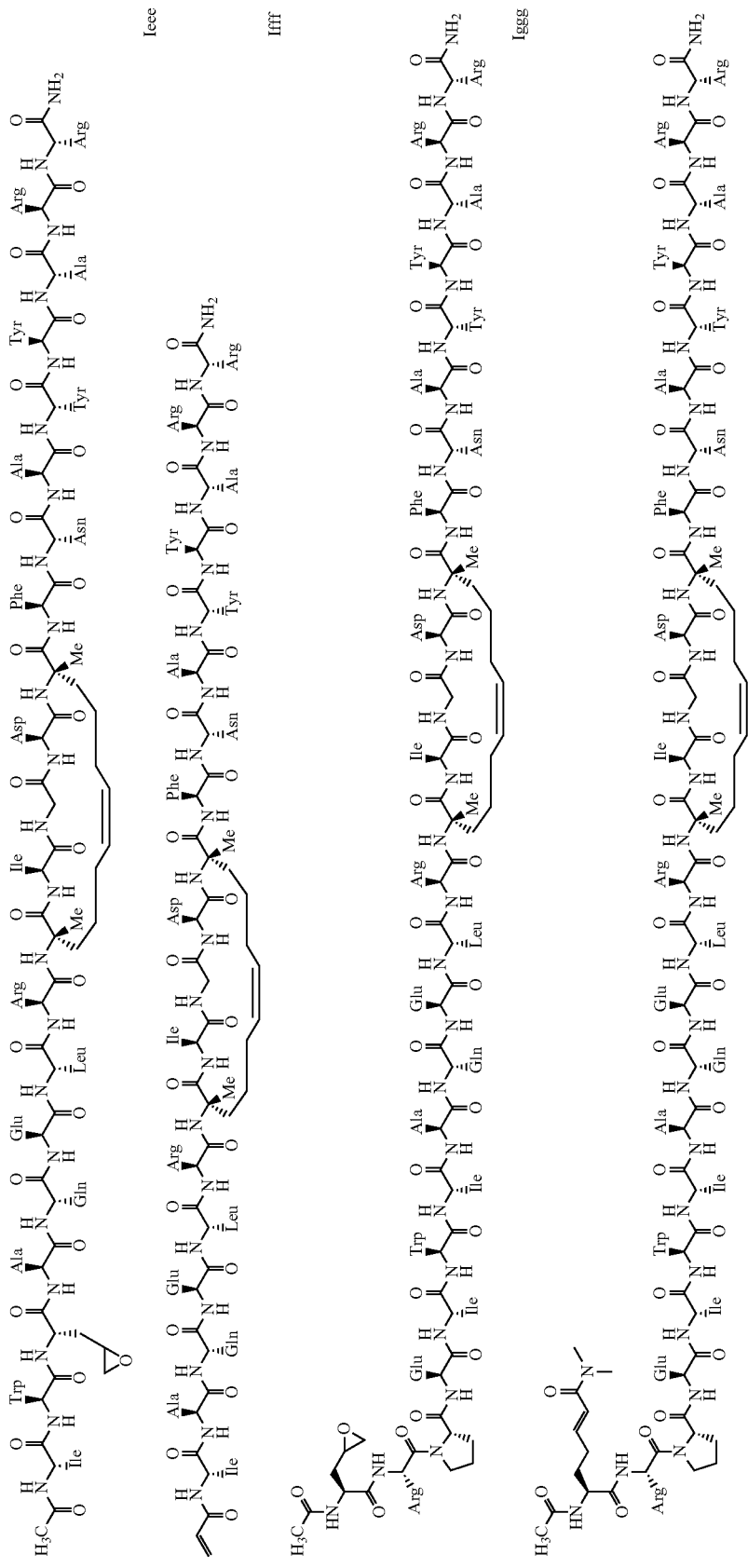

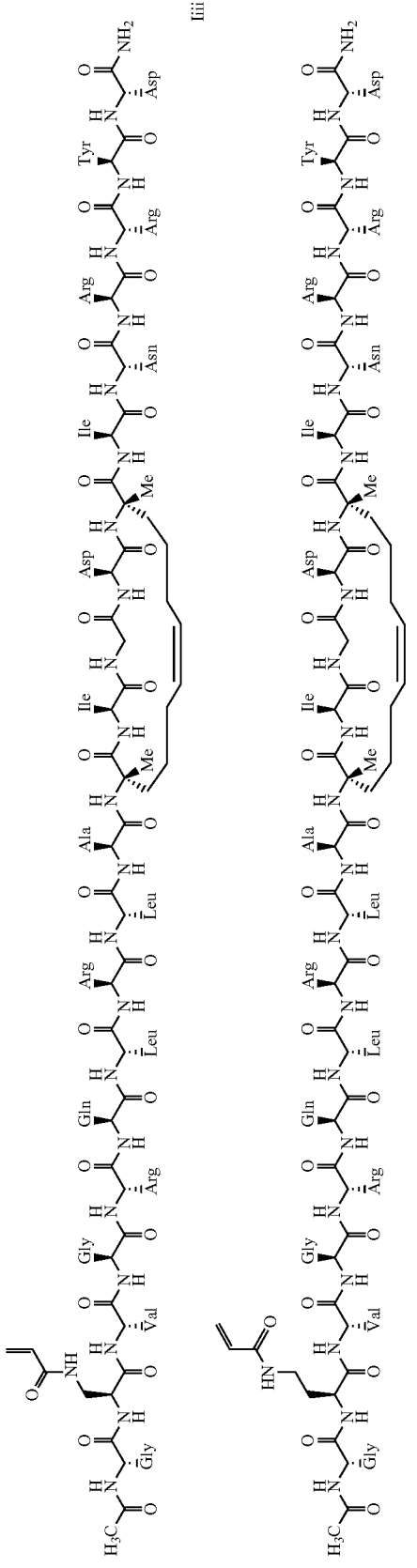

Preparation of Peptidomimetic Macrocycles

Peptidomimetic macrocycles of the invention may be prepared by any of a variety of methods known in the art. For example, the preparation of peptidomimetic macrocycles is described in Schafmeister et al. (2000), J. Am. Chem. Soc. 122: 5891-5892; Walensky et al. (2004) Science 305: 1466-1470 and U.S. Pat. No. 7,192,713. In some examples the warhead is installed in the last step of the synthetic sequence as in the Lys modified amino acid containing warheads. Certain α,α-disubstituted amino acids and amino acid precursors may be employed in the synthesis of the peptidomimetic macrocycle precursor polypeptides of Formula I. For example, the precursor "olefin amino acids" that may be used are (S)-α-(2'-pentenyl) alanine and (R)-α-(2'-octenyl) alanine Following incorporation of such amino acids into precursor polypeptides, the terminal olefins are reacted with a metathesis catalyst, leading to the formation of the peptidomimetic macrocycle.

In some embodiments, the synthesis of these peptidomimetic macrocycles involves a multi-step process that features the synthesis of a peptidomimetic precursor containing an azide moiety and an alkyne moiety; followed by contacting the peptidomimetic precursor with a macrocyclization reagent to generate a triazole-linked peptidomimetic macrocycle. Such a process is described, for example, in US Patent Application Publication No. 2008-0262200 A1. Macrocycles or macrocycle precursors are synthesized, for example, by solution phase or solid-phase methods, and can contain both naturally-occurring and non-naturally-occurring amino acids. See, for example, Hunt, "The Non-Protein Amino Acids" in Chemistry and Biochemistry of the Amino Acids, edited by G. C. Barrett, Chapman and Hall, 1985.

In some embodiments, the peptidomimetic precursor is purified prior to the contacting step. In other embodiments, the peptidomimetic macrocycle is purified after the contacting step. In still other embodiments, the peptidomimetic macrocycle is refolded after the contacting step. The method may be performed in solution, or, alternatively, the method may be performed on a solid support.

In some embodiments, w+x+y is 3, and A, B and C are independently natural or non-natural amino acids. In other embodiments, w+x+y is 6, and C, W and D are independently natural or non-natural amino acids.

In some embodiments, the contacting step is performed in a solvent selected from the group consisting of protic solvent, aqueous solvent, organic solvent, and mixtures thereof. For example, the solvent may be chosen from the group consisting of $H_2O$, THF, THF/$H_2O$, t-BuOH/$H_2O$, DMF, DIPEA, $CH_3CN$ or $CH_2Cl_2$, $ClCH_2CH_2Cl$ or a mixture thereof. The solvent may be a solvent which favors helix formation.

Alternative but equivalent protecting groups, leaving groups or reagents may be employed, and certain of the synthetic steps may be performed in alternative sequences or orders to produce the desired compounds. Synthetic chemistry transformations and protecting group methodologies (protection and deprotection) useful in synthesizing the compounds described herein include, for example, those such as described in Larock, Comprehensive Organic Transformations, VCH Publishers (1989); Greene and Wuts, Protective Groups in Organic Synthesis, 2d. Ed., John Wiley and Sons (1991); Fieser and Fieser, Fieser and Fieser's Reagents for Organic Synthesis, John Wiley and Sons (1994); and Paquette, ed., Encyclopedia of Reagents for Organic Synthesis, John Wiley and Sons (1995), and subsequent editions thereof.

The peptidomimetic macrocycles of the invention are made, for example, by chemical synthesis methods, such as described in Fields et al., Chapter 3 in Synthetic Peptides: A User's Guide, ed. Grant, W. H. Freeman & Co., New York, N.Y., 1992, p. 77. Hence, for example, peptides are synthesized using the automated Merrifield techniques of solid phase synthesis with the amine protected by either tBoc or Fmoc chemistry using side chain protected amino acids on, for example, an automated peptide synthesizer.

One manner of producing the peptidomimetic precursors and peptidomimetic macrocycles described herein uses solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Side chain functional groups are protected as necessary with base stable, acid labile groups.

Longer peptidomimetic precursors are produced, for example, by conjoining individual synthetic peptides using native chemical ligation. Alternatively, the longer synthetic peptides are biosynthesized by well known recombinant DNA and protein expression techniques. Such techniques are provided in well-known standard manuals with detailed protocols. To construct a gene encoding a peptidomimetic precursor of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The present invention contemplates the use of non-naturally-occurring amino acids and amino acid analogs in the synthesis of the peptidomimetic macrocycles described herein. Any amino acid or amino acid analog amenable to the synthetic methods employed for the synthesis of warhead containing peptidomimetic macrocycles can be used in the present invention. For example, L-Lys is contemplated as a useful amino acid in the present invention. However, other analogs of L-Lys containing a shorter side chain are also useful in the invention. For example, L-ornithine containing 3 methylene units attached to a primary amine, L-2,4-diamino-n-butyric acid containing 2 methylene units attached to the primary amine and L-2,3-diaminopropanoic acid containing 1 methylene unit attached to the primary amine are useful in the invention. However other analogs of Lys containing a longer side chain are also useful in the invention. For example, (S)-2,7-diaminoheptanoic acid containing 5 methylene units attached to a primary amine and (S)-2,8-octanoic acid containing 6 methylene units attached to the primary amine are useful in the invention.

In some embodiments the amino acids and amino acid analogs are of the D-configuration. In other embodiments they are of the L-configuration. In some embodiments, some of the amino acids and amino acid analogs contained in the peptidomimetic are of the D-configuration while some of the amino acids and amino acid analogs are of the L-configuration. In some embodiments the amino acid analogs are α,α-disubstituted, such as α-methyl-L-propargylglycine and α-methyl-D-propargylglycine. In some embodiments the amino acid analogs are N-alkylated, e.g., N-methyl-L-propargylglycine and N-methyl-D-propargylglycine.

In some embodiments, the —NH moiety of the amino acid is protected using a protecting group, including without limitation -Fmoc, -Boc and 4-methyltrityl (-Mtt). In some embodiments the protected amino acid analogs are α,α-disubstituted, such as (S)-2-Fmoc-2-methylhept-6-enoic acid. In other embodiments the —NH moiety of the amino acid is bis-protected using Fmoc and Mtt, such as NE-Mtt-Nα-Fmoc-L-lysine and analogs thereof. In other embodiments, the amino acid is not protected prior to synthesis of the peptidomimetic macrocycle.

Figure 3:
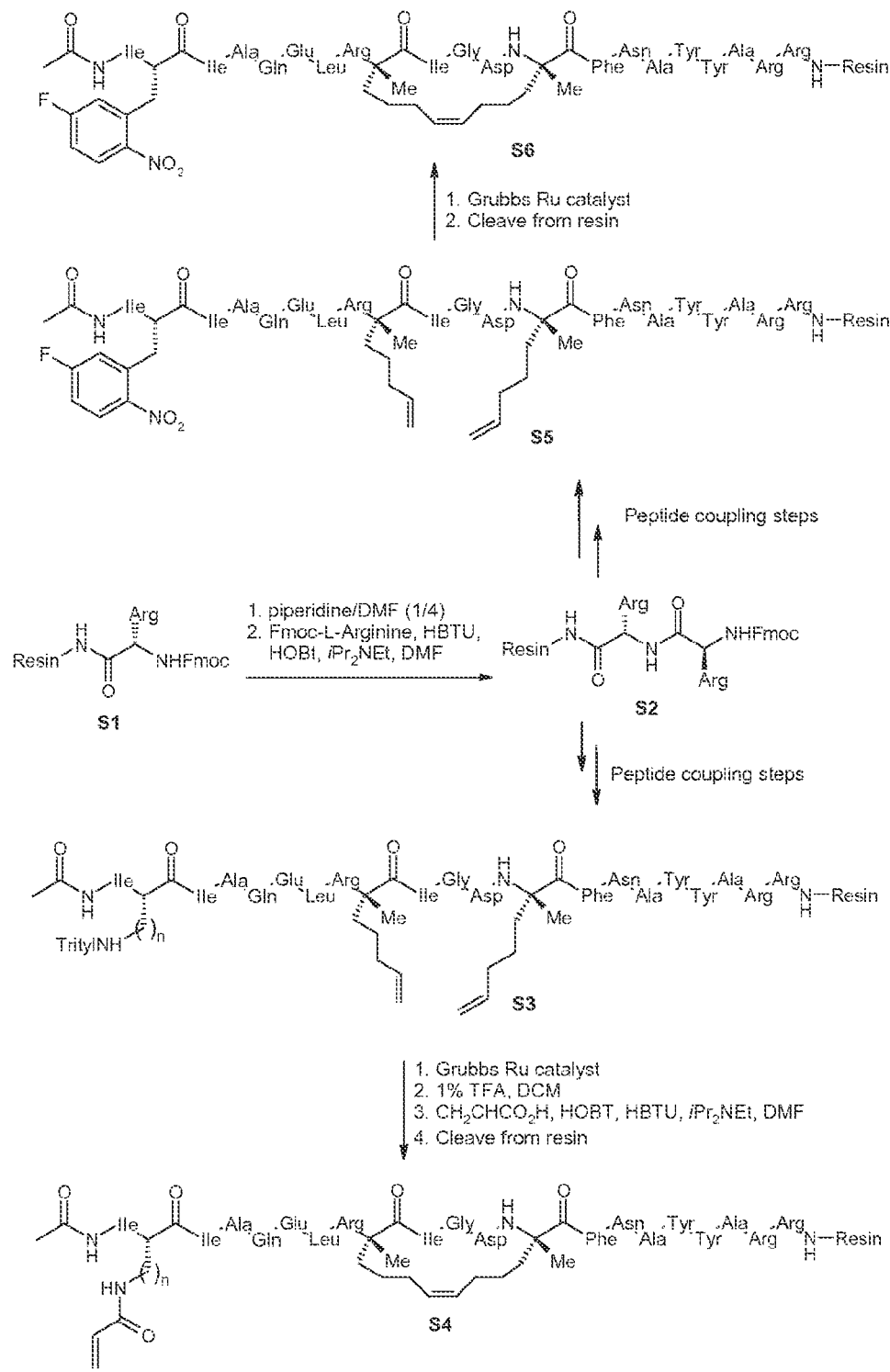
FIG. 3 depicts the preparation of S4 and S6 stapled silencer peptides from Fmoc-L-arginine with the acrylamide group and the 3-fluoro-5-nitro phenyl group as the warheads.

In some embodiments Fmoc-L-arginine is attached to a resin via the carboxylic acid to afford S1 (FIG. 3). Deprotection of the Fmoc protecting group using piperidine/DMF (1/4) followed by coupling with Fmoc-L-arginine would then afford S2. Repeating these steps using amino acids analogous to the BIM-BH3 protein sequence, using (S)-2-Fmoc-2-methylhept-6-enoic acid (precursors for the i+4 staple steps) and NE-Mtt-Nα-Fmoc-L-lysine (precursor to warhead containing amino acid) would afford the peptide S3. Metathesis of the vinyl groups using Grubbs Ruthenium catalyst would install the i+4 staple. Deprotection of the Mtt group using 1% TFA in DCM followed by coupling of the amine with acrylic acid under standard peptide coupling conditions would afford the corresponding acrylamide. Cleavage from the resin would afford the stapled silencer peptide S4 shown in FIG. 3.

In other embodiments the intermediate S2 would be homologated using amino acids analogous to the BIM-BH3 protein sequence using (S)-2-Fmoc-2-methylhept-6-enoic acid (precursors for the i+4 staple steps) and (S)-2-(Fmoc) amino-3-(5-fluoro-2-nitrophenyl)propanoic acid to afford the peptide S5. Metathesis of the vinyl groups using Grubbs Ruthenium catalyst would install the i+4 staple followed by cleavage from the resin would afford the stapled silencer peptide S6 shown in FIG. 3.

Figure 4:
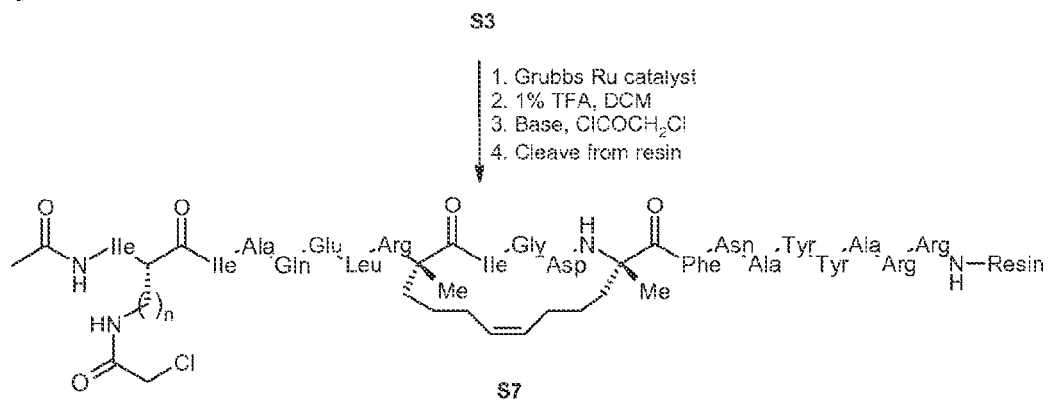
FIG. 4 depicts the preparation of S7 stapled silencer peptides from the intermediate S3 with the chloromethyl amide group as the warhead.

In other embodiments the intermediate peptide S3 would undergo the metathesis reaction followed by the deprotection of the Mtt group and reaction with chloroacetyl chloride to afford the stapled silencer peptide S7 as shown in FIG. 4.

Figure 5:
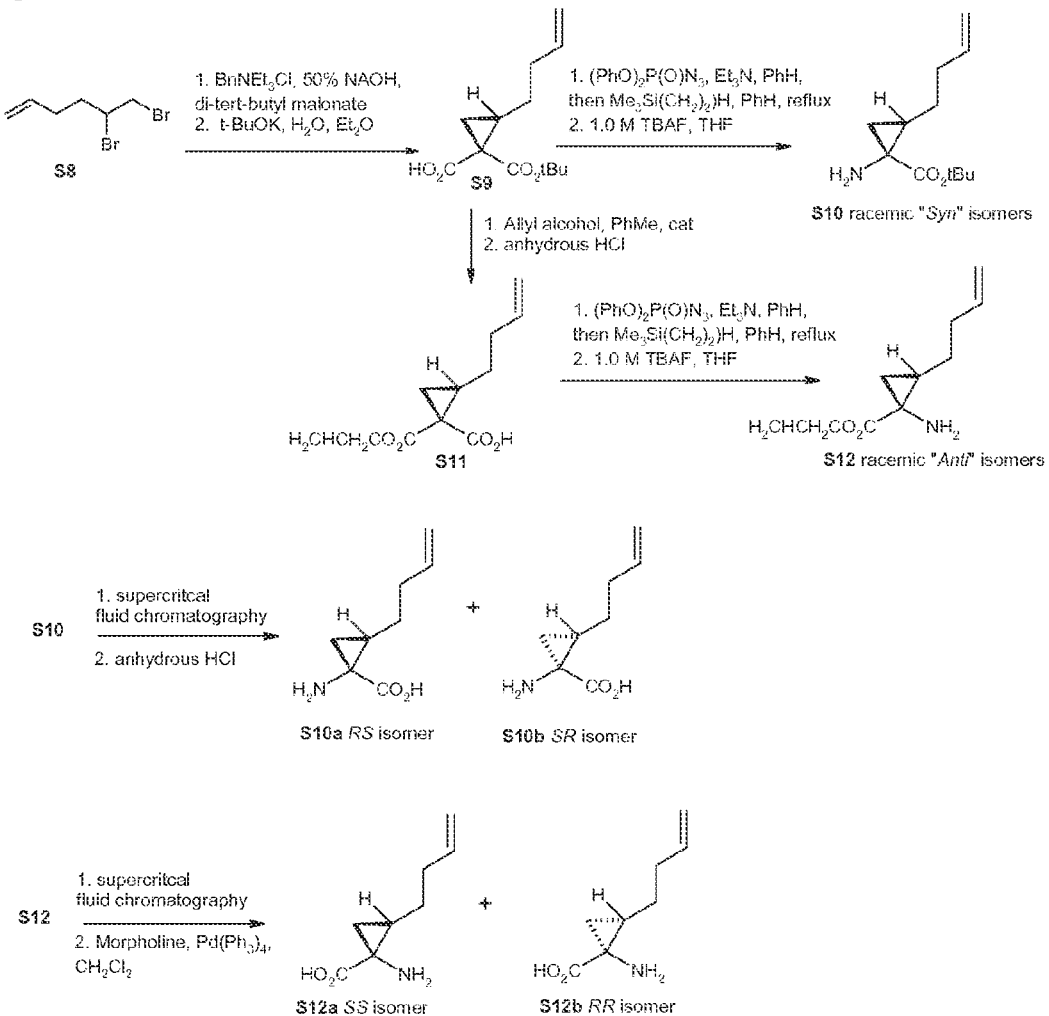
FIG. 5 depicts the preparation of the four chiral isomers (S10 and S12) of 1-amino-2-(but-3-en-1yl)cyclopropanecarboxylic acid.

In other embodiments homoallyl substituted aminocyclopropane carboxylic acids are synthesized as described in FIG. 5 (Tzantrizos et al. (2004), J. Org. Chem. 69: 6185-6201; Rancourt et al. (2004), J. Med. Chem 47: 2511-2522) Dialkylation of di-tert-butylmalonate with 1,2-dibromo-5-hexene S8 followed by selective hydrolysis of the less hindered ester would afford the monoester intermediate S9. The racemic mixture of syn isomers S10 (having the homoallyl side chain syn to the tert-butyl ester) can be prepared via Curtius rearrangement followed by trapping of the products as the 2-(trimethylsilyl)ethyl carbamate derivatives. Deprotection of the carbamate protecting groups with tetrabutylammoniumfluoride (TBAF) would afford the racemic syn isomers S10. In other embodiments the anti isomers S12 (having the homoallyl side chain anti to the tert-butyl ester) could be prepared from the intermediate acid S9 by first converting the carboxylic acid to the corresponding allyl ester and then treating with anhydrous HCl to deprotect the tert-butyl ester. The liberated carboxylic acid can then be transformed into the corresponding amine following the sequence of steps described above for the preparation of the syn isomers. In some embodiments the racemic mixture S10 can be separated into the corresponding RR and SS isomers using supercritical column chromatography (SFC). Hydrolysis of the tert-butyl esters with anhydrous HCl would then afford (1R,2S)-1-amino-2-(but-3-en-1-yl)cyclopopanecarboxylic acid S10a and (1S,2R)-1-amino-2-(but-3-en-1-yl)cyclopopanecarboxylic acid S10b. Similarly, separation of the racemic mixture S12 using SFC followed by Pd(0) catalyzed cleavage of the allyl esters would afford (1S,2S)-1-amino-2-(but-3-en-1-yl)cyclopopanecarboxylic acid S12a and (1R,2R)-1-amino-2-(but-3-en-1-yl)cyclopopanecarboxylic acid S12b as outlined in FIG. 5.

Figure 6:
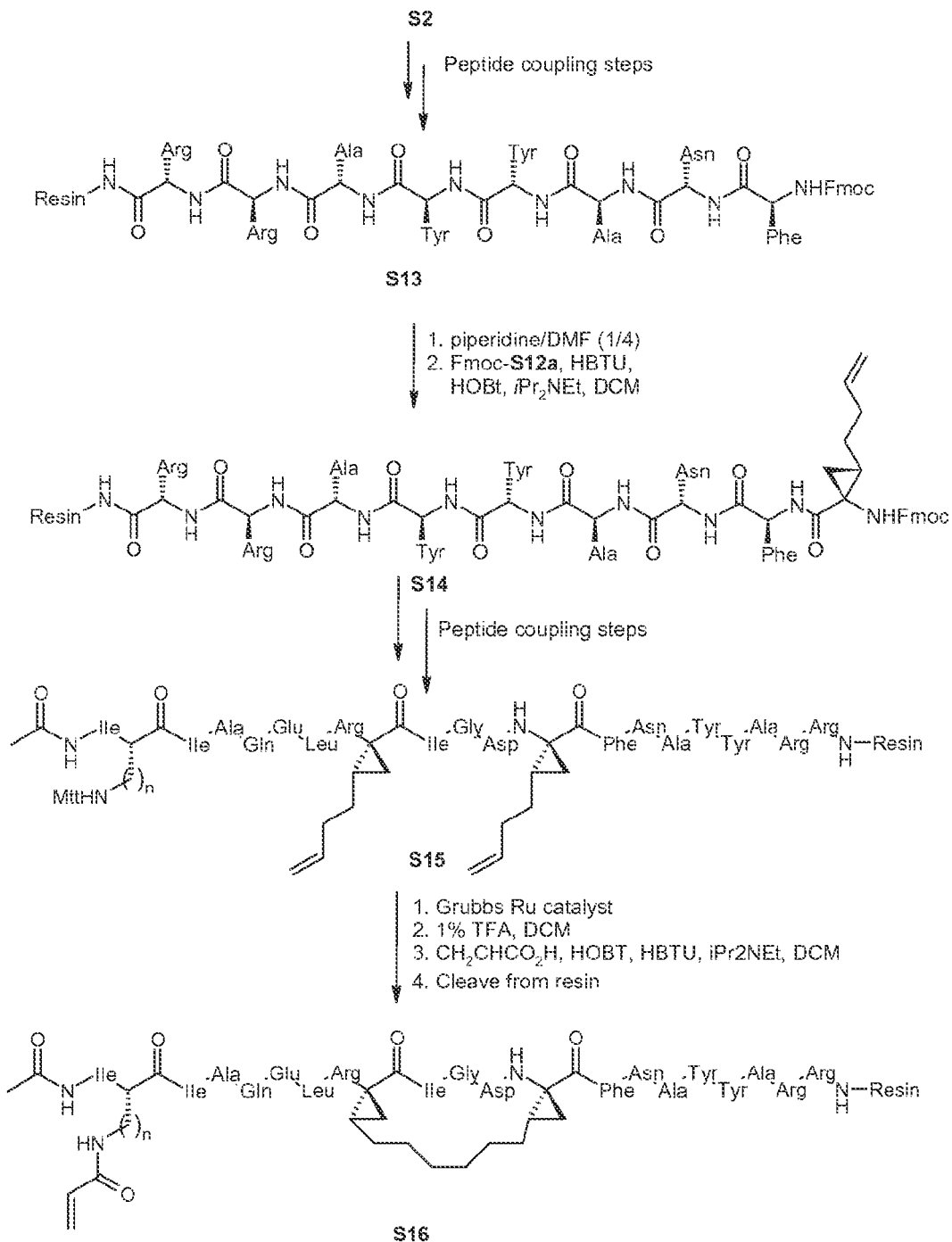
FIG. 6 depicts the preparation of S16 stapled silencer peptides from Fmoc-L-arginine using 1-amino-2-(but-3-en-1yl)cyclopropanecarboxylic acid to provide the linker.

In some embodiments deprotection of the Fmoc protecting group of S2 using piperidine/DMF (1/4) followed by coupling with the Fmoc-L-amino acids asparagine and isoleucine to build the partial sequence analogous to the BIM-BH3 protein sequence would then give the peptide S13. Deprotection of the Fmoc protecting group using piperidine/DMF (1/4) followed by coupling with Fmoc-(1R, 2S)-1-amino-2-(but-3-en-1-yl)cyclopopanecarboxylic acid would then afford S14. Repeating these steps using the amino acid sequence analogous to the BIM-BH3 peptide using and Nε-Mtt-Nα-Fmoc-L-Lys (precursor to warhead containing amino acid) would afford the peptide S15. Metathesis of the vinyl groups using Grubbs Ruthenium catalyst would install the i+4 staple. Deprotection of the Mtt group using 1% TFA in DCM followed by reaction of the amine with acrylic acid would afford the corresponding acrylamide. Cleavage from the resin would afford the stapled silencer peptide S16 shown in FIG. 6.

Figure 7:
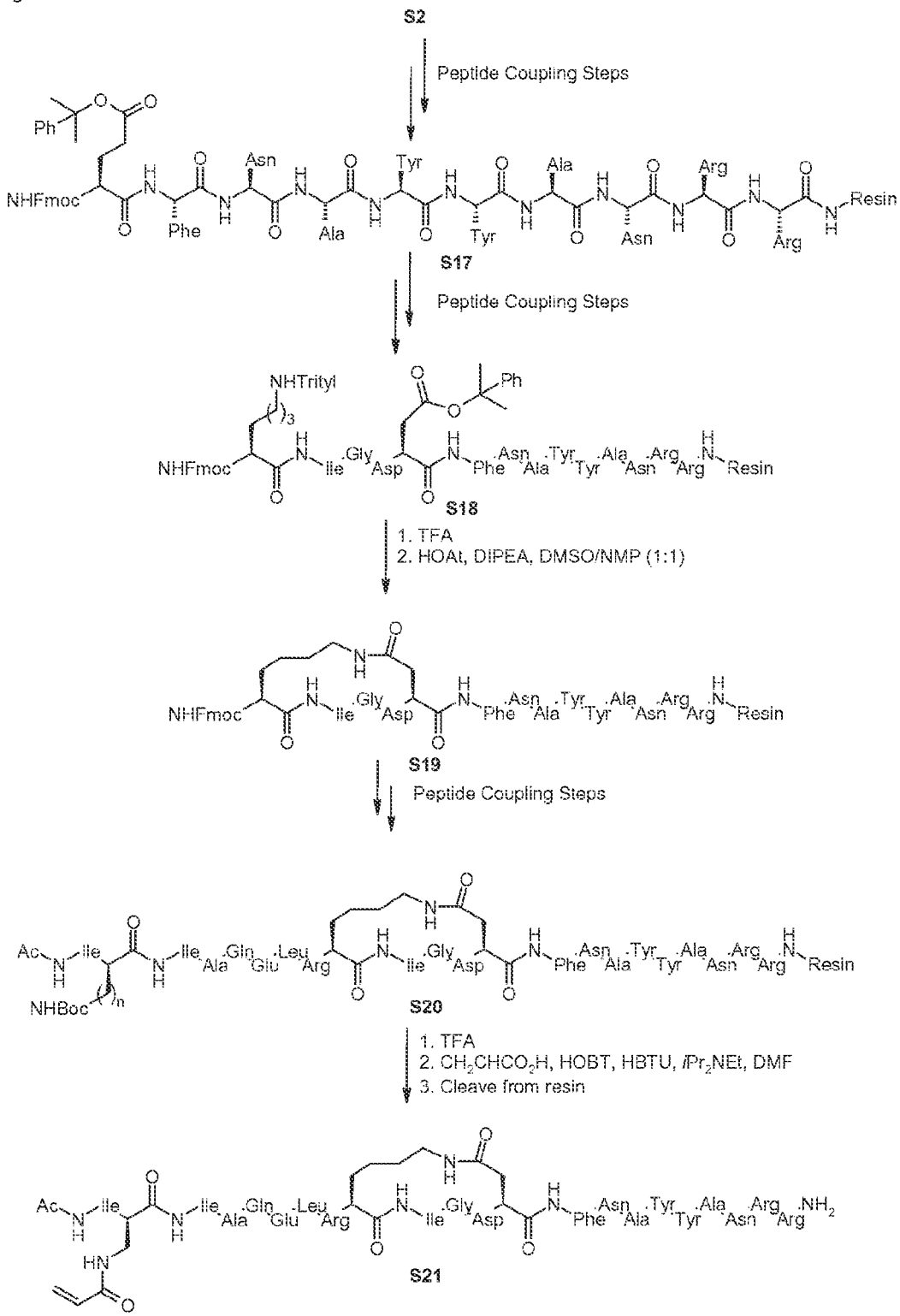
FIG. 7 depicts the preparation of S21 stapled silencer peptides using a lactam macrocycle as the staple.

In some embodiments deprotection of the Fmoc protecting group of S2 followed by peptide coupling with Fmoc-L-amino acids analogous to the BIM-BH3 protein sequence and using the Fmoc protected phenyl isopropyl ester of aspartic acid as the last amino acid in the sequence would afford S17 (FIG. 7). Repeating the coupling steps an additional 4 times using the Fmoc protected methyl trityl group of Lys would afford the amino acid sequence S18. Deprotection of the trityl protected amine and phenyl isopropyl ester groups followed by cyclization on-resin (Harrison et al. (2010), PNAS, 107:11686-11691) using 1-hydroxy-7-azabenzotriazole (HOAt) and N,N, diisoproylethylamine (DIPEA) in DMSO/NMP (1:1) would afford the corresponding lactam S19. Repeating these steps using the amino acid sequence analogous to the BIM-BH3 peptide using and Nε-Boc-Nα-Fmoc-L-Lys (precursor to warhead containing amino acid) would afford the peptide S20. Deprotection of the Boc group using TFA followed by reaction of the amine with acrylic acid would afford the corresponding acrylamide containing stapled silencer peptide S21 (FIG. 7).

Examples of stapled silencer peptides of the invention are shown in Table 3.

| Peptide | Peptide Sequence | Purity % | Calculated Mass m/z | Observed Mass m/z |
|---|---|---|---|---|
| Ijj | Ac-I-Phe(2-F,5-NO$_2$)-IAQALR-X-IGD-X-FNAYYARR-CONH$_2$ | >96 | 2615.03 | 2615.83 |
| Ill | Ac-I-Dap(acrylyl)-I-AQELR-X-IGD-X-FNAYYARR-CONH$_2$ | >98 | 2601.03 | 2601.26 |

-continued

| Peptide | Peptide Sequence | Purity % | Calculated Mass m/z | Observed Mass m/z |
|---|---|---|---|---|
| Iww | Ac-I-Phe(2-F,5-NO$_2$)-IA-X-ALR-X-IGDEFNAYYARR-CONH$_2$ | >98 | 2616.02 | 2616.43 |
| Iyy | Ac-I-Dap(acrylyl)-IA-X-ALR-X-IGDEFNAYYARR-CONH$_2$ | >97 | 2543.98 | 2543.24 |
| Ihhh | Ac-I-Dap(acrylyl)-VGRQLA-X-IGD-X-INRRYD-CONH$_2$ | >98 | 2234.57 | 2234.40 |
| Iiii | Ac-I-Dab(acrylyl)-VGRQLA-X-IGD-X-INRRYD-CONH$_2$ | >98 | 2248.59 | 2248.14 |

X = (S)-2-(4-pentyl)alanine hydrocarbon stapled peptide
Dap = diaminopropionic acid
Dab = diaminobutanoic acid

Methods of Use

In one aspect, the present invention provides novel peptidomimetic macrocycles that are useful in competitive binding assays to identify agents which bind to the natural ligand(s) of the proteins or peptides upon which the peptidomimetic macrocycles are modeled. For example, the anti-apoptotic BCL2 proteins, BCL2-A1 and MCL-1 have been identified as important cellular oncogenes that not only promote tumorigenesis but also contribute to the resistance of chemotherapeutic drugs and failure of anti-cancer treatments. The binding partners of BCL2-A1 and MCL-1 include the BH3-only proteins, BIM, BID and NOXA. Labeled peptidomimetic macrocycles based on BH3 can be used in a BIM binding assay along with small molecules that competitively bind to BCL2-A1 or MCL-1. Conversely, labeled peptidomimetic macrocycles based on BH3 can be used in a BID binding assay along with small molecules that competitively bind to BCL2-A1 and MCL-1. Competitive binding studies allow for rapid in vitro evaluation and determination of drug candidates specific for the BCL2-A1/BIM or BID or NOXA system. Such binding studies may be performed with any of the peptidomimetic macrocycles disclosed herein and their binding partners.

In other aspects, the present invention provides for both prophylactic and therapeutic methods of treating a subject at risk of (or susceptible to) a disorder or having a disorder associated with aberrant (e.g. excessive) expression or activity of the BCL2 proteins including BCL2-A1 and MCL-1. In another embodiment, a disorder is caused, at least in part, by an abnormal level of BCL2-A1 or MCL-1, (e.g., over expression), or by the presence of BCL2-A1 or MCL-1 exhibiting abnormal activity. As such, the reduction in the level and/or activity of the BCL2-A1 or MCL-1 is used, for example, to ameliorate or reduce the adverse symptoms of the disorder.

In some embodiments, the administration of the compounds of the present invention induces cell growth arrest or apoptosis. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

In some embodiments, the peptidomimetic macrocycles of the invention is used to treat, prevent, and/or diagnose cancers and neoplastic conditions. As used herein, the terms "cancer", "hyperproliferative" and "neoplastic" refer to cells having the capacity for autonomous growth, e.g., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A metastatic tumor can arise from a multitude of primary tumor types, including but not limited to those of breast, lung, liver, colon and ovarian origin. "Pathologic hyperproliferative" cells occur in disease states characterized by malignant tumor growth. Examples of non-pathologic hyperproliferative cells include proliferation of cells associated with wound repair. Examples of cellular proliferative and/or differentiative disorders include cancer, e.g., carcinoma, sarcoma, or metastatic disorders. In some embodiments, the peptidomimetic macrocycles are novel therapeutic agents for controlling breast cancer, ovarian cancer, colon cancer, lung cancer, metastasis of such cancers and the like.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, mecllullary carcinoma, bronchogenic carcinoma, renal cell carcinoma, hepatoma, bile duct carcinoma, choriocarcinoma, serninoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hernangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus (1991), Crit Rev. Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Stemberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (rnucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, non-neoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometrioid tumors, clear cell adenocarcinoma, cystadenofibroma, Brenner tumor, surface epithelial tumors; germ cell tumors such as mature (benign) teratomas, monodermal teratomas, immature malignant teratomas, dysgerminoma, endodermal sinus rumor, choriocarcinoma; sex cord-stomal tumors such as, granulosa-theca cell tumors, thecomafibromas, androblastomas, hill cell tumors, and gonadoblastoma; and metastatic tumors such as Krukenberg tumors.

In other or further embodiments, the peptidomimetic macrocycles described herein are used to treat, prevent or diagnose conditions characterized by overactive cell death or cellular death due to physiologic insult, etc. Some examples of conditions characterized by premature or unwanted cell death are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, and myelodysplasia. In other or further embodiments, the peptidomimetic macrocycles of the invention that act to decrease apoptosis are used to treat disorders associated with an undesirable level of cell death. Thus, in some embodiments, the anti-apoptotic peptidomimetic macrocycles of the invention are used to treat disorders such as those that lead to cell death associated with viral infection, e.g., infection associated with infection with human immunodeficiency virus (HIV).

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. In other or further embodiments, the anti-apoptotic peptidomimetic macrocycles of the invention are used to treat all such disorders associated with undesirable cell death.

In another embodiment, the peptidomimetic macrocycles described herein are used to treat, prevent or diagnose inflammatory disorders. Numerous types of inflammatory disorders exist. Certain inflammatory diseases are associated with the immune system, for example, autoimmune diseases. Autoimmune diseases arise from an overactive immune response of the body against substances and tissues normally present in the body, i.e. self antigens. In other words, the immune system attacks its own cells. Autoimmune diseases are a major cause of immune-mediated diseases. Rheumatoid arthritis is an example of an autoimmune disease, in which the immune system attacks the joints, where it causes inflammation (i.e. arthritis) and destruction. It can also damage some organs, such as the lungs and skin. Rheumatoid arthritis can lead to substantial loss of functioning and mobility. Rheumatoid arthritis is diagnosed with blood tests especially the rheumatoid factor test. Some examples of autoimmune diseases that are treated with the peptidomimetic macrocycles described herein include, but are not limited to, acute disseminated encephalomyelitis (ADEM), Addison's disease, ankylosingspondylitis, antiphospholipid antibody syndrome (APS), autoimmune hemolytic anemia, autoimmune hepatitis, autoimmune inner ear disease, Bechet's disease, bullous pemphigoid, coeliac disease, Chagas disease, Churg-Strauss syndrome, chronic obstructive pulmonary disease (COPD), Crohn's disease, demiatomyositis, diabetes mellitus type 1, endometriosis, Goodpasture's syndrome, Graves' disease, Guillain-Barré syndrome (GBS), Hashimotds disease, Hidradenitis suppurativa, idiopathic thrombocytopenic purpura, inflammatory bowel disease (IBD), interstitial Cystitis, lupus erythematosus, morphea, multiple sclerosis, myasthenia gravis, narcolepsy, neuromyotonia, pemphigus vulgaris, pernicious anaemia, Polymyositis, polymyalgia rheumatica, primary biliary cirrhosis, psoriasis, rheumatoid arthritis, schizophrenia, scleroderma, Sjogren's syndrome, temporal arteritis (also known as "giant cell arteritis"), Takayasu's arteritis, Vasculitis, Vitiligo, and Wegener's granulomatosis.

Some examples of other types of inflammatory disorders that are treated with the peptidomimetic macrocycles described herein include, but are not limited to, allergy including allergic rhinitis/sinusitis, skin allergies (urticaria/hives, angioedema, atopic dermatitis), food allergies, drug allergies, insect allergies, and rare allergic disorders such as mastocytosis, asthma, arthritis including osteoarthritis, rheumatoid arthritis, and spondyloanhropathies, primary angitis of the CNS, sarcoidosis, organ transplant rejection, fibromyalgia, fibrosis, pancreatitis, and pelvic inflammatory disease.

Examples of cardiovascular disorders (e.g., inflammatory disorders) that are treated or prevented with the peptidomimetic macrocycles of the invention include, but are not limited to, aortic valve stenosis, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

Pharmaceutical Compositions and Methods of Administration

The peptidomimetic macrocycles of the invention also include pharmaceutically acceptable derivatives or prodrugs thereof. A "pharmaceutically acceptable derivative" means any pharmaceutically acceptable salt, ester, salt of an ester, pro-drug or other derivative of a compound of this invention which, upon administration to a recipient, is capable of providing (directly or indirectly) a compound of this invention. Particularly favored pharmaceutically acceptable derivatives are those that increase the bioavailability of the compounds of the invention when administered to a mammal (e.g., by increasing absorption into the blood of an orally administered compound) or which increases delivery of the active component to a biological compartment (e.g., the brain or lymphatic system) relative to the parent species. Some pharmaceutically acceptable derivatives include a chemical group, which increases aqueous solubility or active transport across the gastrointestinal mucosa.

In some embodiments, the peptidomimetic macrocycles of the invention are modified by covalently or non-covalently joining appropriate functional groups to enhance selective biological properties. Such modifications include those which increase biological penetration into a given biological compartment (e.g., blood, lymphatic system, central nervous system), increase oral availability, increase solubility to allow administration by injection, alter metabolism, and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts.

For preparing pharmaceutical compositions from the compounds of the present invention, pharmaceutically acceptable carriers include either solid or liquid carriers. Solid form preparations include powders, tablets, pills, capsules, cachets, suppositories, and dispersible granules. A solid carrier can be one or more substances, which also acts as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Maack Publishing Co, Easton Pa.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of Formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of Formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.2 to about 100 mg/kg, e.g., from about 0.5 to about 75 mg/kg of body weight per day, such as 1 to about 20 mg per kilogram body weight of the recipient per day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Compounds of the invention can also be administered in combination with other therapeutic agents, for example, other agents that are useful for the treatment of cancer. Examples of such agents include gemcitabine (Gemzar). Accordingly, in one embodiment the invention also provides a composition comprising a compound of Formula I, or a pharmaceutically acceptable salt thereof, at least one other therapeutic agent, and a pharmaceutically acceptable diluent or carrier. The invention also provides a kit comprising a compound of Formula I, or a pharmaceutically acceptable salt thereof, at least one other therapeutic agent, packaging material, and instructions for administering the compound of Formula I or the pharmaceutically acceptable salt thereof and the other therapeutic agent or agents to an animal to treat cancer.

When the compositions of this invention comprise a combination of a peptidomimetic macrocycle and one or more additional therapeutic or prophylactic agents, both the compound and the additional agent should be present at dosage levels of between about 1 to 100%, and more preferably between about 5 to 95% of the dosage normally administered in a monotherapy regimen. In some embodiments, the additional agents are administered separately, as part of a multiple dose regimen, from the compounds of this invention. Alternatively, those agents are part of a single dosage form, mixed together with the compounds of this invention in a single composition.

ASSAYS AND EXAMPLES

The properties of the peptidomimetic macrocycles of the invention are assayed, for example, by using the methods described below.

Assay to Determine α-Helicity

In solution, the secondary structure of polypeptides with α-helical domains will reach a dynamic equilibrium between random coil structures and α-helical structures, often expressed as a "percent helicity". Thus, for example, unmodified pro-apoptotic BH3 domains are predominantly random coils in solution, with α-helical content usually under 25%. Peptidomimetic macrocycles with optimized linkers, on the other hand, possess, for example, an alpha-helicity that is at least two-fold greater than that of a corresponding uncrosslinked polypeptide. In some embodiments, macrocycles of the invention will possess an alpha-helicity of greater than 50%. To assay the helicity of peptidomimetic macrocyles of the invention, such as BH3 domain-based macrocycles, the compounds are dissolved in an aqueous solution (e.g. 50 mM potassium phosphate solution at pH 7, or distilled $H_2O$, to concentrations of 25-50 µM). Circular dichroism (CD) spectra are obtained on a spectropolarimeter (e.g., Jasco J-710) using standard measurement parameters (e.g. temperature, 20° C.; wavelength, 190-260 nm; step resolution, 0.5 nm; speed, 20 nm/sec; accumulations, 10; response, 1 sec; bandwidth, 1 nm; path length, 0.1 cm). The α-helical content of each peptide is calculated by dividing the mean residue ellipticity (e.g. [φ]222obs) by the reported value for a model helical decapeptide (Yang et al. (1986), Methods Enzymol. 130:208)).

Assay to Determine Melting Temperature (Tm)

A peptidomimetic macrocycle of the invention comprising a secondary structure such as an α-helix exhibits, for example, a higher melting temperature than a corresponding uncrosslinked polypeptide. Typically peptidomimetic macrocycles of the invention exhibit Tm of >60° C. representing a highly stable structure in aqueous solutions. To assay the effect of macrocycle formation on melting temperature, peptidomimetic macrocycles or unmodified peptides are dissolved in distilled $H_2O$ (e.g. at a final concentration of 50 µM) and the Tm is determined by measuring the change in ellipticity over a temperature range (e.g. 4 to 95° C.) on a spectropolarimeter (e.g., Jasco J-710) using standard parameters (e.g. wavelength 222 nm; step resolution, 0.5 nm; speed, 20 nm/sec; accumulations, 10; response, 1 sec; bandwidth, 1 nm; temperature increase rate: 1° C./min; path length, 0.1 cm).

Protease Resistance Assay

The amide bond of the peptide backbone is susceptible to hydrolysis by proteases, thereby rendering peptidic compounds vulnerable to rapid degradation in vivo. Peptide helix formation, however, typically buries the amide backbone and therefore may shield it from proteolytic cleavage. The peptidomimetic macrocycles of the present invention may be subjected to in vitro trypsin proteolysis to assess for any change in degradation rate compared to a corresponding uncrosslinked polypeptide, For example, the peptidomimetic macrocycle and a corresponding uncrosslinked polypeptide are incubated with trypsin agarose and the reactions quenched at various time points by centrifugation and subsequent HPLC injection to quantitate the residual substrate by ultraviolet absorption at 280 nm. Briefly, the peptidomimetic macrocycle and peptidomimetic precursor (5 µg) are incubated with trypsin agarose (Pierce) (S/E ~125) for 0, 10, 20, 90, and 180 minutes. Reactions are quenched by tabletop centrifugation at high speed; remaining substrate in the isolated supernatant is quantified by HPLC-based peak detection at 280 um. The proteolytic reaction displays first order kinetics and the rate constant, k, is determined from a plot of ln [S] versus time (k=–1×slope).

Ex Vivo Stability Assay

Peptidomimetic macrocycles with optimized linkers possess, for example, an ex vivo half-life that is at least two-fold greater than that of a corresponding uncrosslinked polypeptide, and possess an ex vivo half-life of 12 hours or more. For ex vivo serum stability studies, a variety of assays may be used. For example, a peptidomimetic macrocycle and/or a corresponding uncrosslinked polypeptide (2 µg) are each incubated with fresh mouse, rat and/or human serum (e.g. 1-2 mL) at 37° C. for 0, 1, 2, 4, 8, and 24 hours. Samples of differing macrocycle concentration may be prepared by serial dilution with serum. To determine the level of intact compound, the following procedure may be used: The samples are extracted by transferring 100 µl of serum to 2 ml centrifuge tubes followed by the addition of 10 µL of 50% formic acid and 500 µL acetonitrile and centrifugation at 14,000 RPM for 10 min at 4° C. The supernatants are then transferred to fresh 2 ml tubes and evaporated on Turbovap under nitrogen <10 psi, 37° C. The samples are reconstituted in 100 µL of 50:50 acetonitrile:water and submitted to LC-MS/MS analysis. Equivalent or similar procedures for testing ex vivo stability are known and may be used to determine stability of macrocycles in serum.

Protein Production for Assay Experiments

To assess the binding and affinity of peptidomimetic macrocycles to acceptor proteins, the proteins are produced using standard protocols. Recombinant and tagless BCL-XLΔC, MCL-1ΔNΔC, BCL-wΔC, and BFL-1/A1ΔC are produced and purified using published protocols (Walensky et al. (2006), *Mol. Cell*, 24(2):199-210; Stewart et al. (2010), *Nat. Chem. Biol*, 6(8):595-601). Briefly, glutathione-S-transferase fusion proteins are expressed in *Escherichia coli* BL21 (DE3) using pGEX2T (Pharmacia Biotech) constructs. Bacterial cells are cultured in ampicillin-containing Luria Broth, and protein expression is induced with 0.5 mM isopropyl β-D-1-thiogalactopyranoside. The bacterial pellet is resuspended in PBS containing 1 mg/ml lysozyme, complete protease inhibitor tablet, and 1% (v/v) Triton X-100 and sonicated, and, after centrifugation at 45,000 g for 45 minutes, the supernatant is applied to a glutathione-agarose (Sigma-Aldrich) column and washed with PBS. Tagless protein is obtained by overnight on-bead digestion with thrombin (50 units) (GE Healthcare) in PBS (3 ml) at room temperature, and the cleaved proteins are purified by size exclusion chromatography using 150 mM NaCl and 50 mM Tris (pH 7.4) buffer conditions.

Cell Viability Assay

To assess the cytotoxicity of peptidomimetic macrocycles cells are incubated in the presence of the peptidomimetic macrocycle. Cancer cells ($1 \times 10^4$ cells, 50 µl) are aliquoted in 96-well opaque plates and treated with serial dilutions of vehicle (0.2% DMSO) and peptidomimetic macrocycles in serum-free RPMI media for 2 hours, followed by serum replacement with 20% FBS-containing RPMI media (50 µl) for a final volume of 100 µl containing 10% FBS. Cell viability was assayed at 24 hours by addition of CellTiter-Glo chemiluminescence reagent (Promega), and luminescence measured by a SpectraMax M5 microplate reader (Molecular Devices). For adherent fibroblasts, WS1 (2.5× 103) and WT ($2.5 \times 10^3$) and DKO ($1.5 \times 10^3$) cells were plated in their respective culture media (see above), and, 24 hours later (~75%-90% cellular confluence), media was removed and the cells were washed with the corresponding serum-free media. The indicated doses of peptidomimetic macrocycle were then added in serum free media (50 µl), serum was replaced after 2 hours (20% FBS-containing media, 50 µl), and cell viability was measured at 24 hours as above.

Annexin V Binding Assay

To assess whether the peptidomimetic macrocycles kill cells by activating the apoptotic machinery the percentage of annexin can be measured. Cancer cells ($5 \times 10^4$ cells) are treated with peptidomimetic macrocycles, washed with PBS and annexin V binding buffer after 6 hours, and incubated with FITC-annexin V (BD Pharmingen) for 20 minutes at room temperature in the dark (Billen et al. (2008), *PLos Biol.*, 6(6):e147). Cells are then washed with binding buffer and analyzed by flow cytometry on a FACS Calibur (Becton Dickinson), and the percentage annexin V positivity is calculated using FlowJo software.

Caspase-3/7 Activation Assay

To assess whether the peptidomimetic macrocycles kill cells by activating the apoptotic machinery the percentage of caspase 3/7 activation can be measured. Cancer cells and fibroblasts are treated with peptidomimetic macrocycles, for cell viability assays, and caspase-3/7 activation is measured at 6 hours by addition of the Caspase-Glo 3/7 chemiluminescence reagent in accordance with the manufacturer's protocol (Promega). Luminescence is detected by a SpectraMax M5 microplate reader (Molecular Devices).

In Vitro Binding Assays

To assess the binding and affinity of peptidomimetic macrocycles to acceptor proteins, a fluorescence polarization assay (FPA) is used, for example. The FPA technique measures the molecular orientation and mobility using polarized light and fluorescent tracer. When excited with polarized light, fluorescent tracers (e. g., FITC) attached to molecules with high apparent molecular weights (e.g. FITC-labeled peptides bound to a large protein) emit higher levels of polarized fluorescence due to their slower rates of rotation as compared to fluorescent tracers attached to smaller molecules (e.g. FITC-labeled peptides that are free in solution). For example, fluoresceinated peptidomimetic macrocycles (25 nM) are incubated with the acceptor protein (25-1000 nM) in binding buffer (140 mM NaCl, 50 mM Tris-HCL, pH 7.4) for 30 minutes at room temperature. Binding activity is measured, for example, by fluorescence polarization on a luminescence spectrophotometer (e.g. Perkin-Elmer LSSOB). Kd values may be determined by nonlinear regression analysis using, for example, Graphpad Prism software (GraphPad Software, Inc., San Diego, Calif.). A peptidomimetic macrocycle of the invention shows, in some instances, similar or lower Kd than a corresponding uncrosslinked polypeptide. Acceptor proteins for BH3-peptides such as BCL-2, BCL-XL, BAX, BCL2-A1 or MCL1 may, for example, be used in this assay.

In Vitro Displacement Assays to Characterize Antagonists of Peptide-Protein Interactions To assess the binding and affinity of compounds that antagonize the interaction between a peptide (e. g. a BH3 peptide or a p53 peptide) and an acceptor protein, a fluorescence polarization assay (FPA) utilizing a fluoresceinated peptidomimetic macrocycle derived from a peptidomimetic precursor sequence is used, for example. The FPA technique measures the molecular orientation and mobility using polarized light and fluorescent tracer. When excited with polarized light, fluorescent tracers (e.g., FITC) attached to molecules with high apparent molecular weights (e. g. FITC-labeled peptides bound to a large protein) emit higher levels of polarized fluorescence due to their slower rates of rotation as compared to fluorescent tracers attached to smaller molecules (e.g. FITC-labeled peptides that are flee in solution). A compound that antagonizes the interaction between the fluoresceinated peptidomimetic macrocycle and an acceptor protein will be detected in a competitive binding FPA experiment. For example, putative antagonist compounds (1 nM to 1 mM) and a fluoresceinated peptidomimetic macrocycle (25 nM) are incubated with the acceptor protein (50 nM) in binding buffer (140 mM NaCl, 50 mM Tris-HCL, pH 7.4) for 30 minutes at room temperature. Antagonist binding activity is measured, for example, by fluorescence polarization on a luminescence spectrophotometer (e.g. Perkin-Elmer LSSOB). Kd values may be determined by nonlinear regression analysis using, for example, Graphpad Prism software (GraphPad Software, Inc., San Diego, Calif.). Any class of molecule, such as small organic molecules, peptides, oligonucleotides or proteins can be examined as putative antagonists in this assay. Acceptor proteins for BH3-peptides such as BCL2, BCL-XL, BAX or MCLI can be used in this assay.

Binding Assays in Cell Lysates or Intact Cells

It is possible to measure binding of peptides or peptidomimetic macrocycles to their natural acceptors in cell lysates or intact cells by immunoprecipitation and pull-down experiments. For example, intact cells are incubated with fluoresceinated (FITC-labeled) or biotinylated compounds for 4 hrs in the absence of serum, followed by serum replacement and further incubation that ranges from 4-18 hrs. Alternatively, cells can be incubated for the duration of the experiment in Opti-MEM (Invitrogen). Cells are then pelleted and incubated in lysis buffer (50 mM Tris [pH 7.6], 150 mM NaCl, 1% CHAPS and protease inhibitor cocktail) for 10 minutes at 4° C. 1% NP-40 or Triton X-100 may be used instead of CHAPS. Extracts are centrifuged at 14,000 rpm for 15 minutes and supernatants collected and incubated with 10 µl goat anti-FITC antibody or streptavidin-coated beads for 2 hrs, rotating at 4° C. followed by further 2 hrs incubation at 4° C. with protein A/G Sepharose (50 µl of 50% bead slurry). No secondary step is necessary if using streptavidin beads to pull down biotinylated compounds. Alternatively FITC-labeled or biotinylated compounds are incubated with cell lysates, prepared as described above, for 2 hrs, rotating at 4° C. followed by incubation with 10 pl goat anti-FITC antibody or streptavidin-coated beads for 2 hrs, rotating at 4° C. followed by further 2 hrs incubation at 4° C. with protein A/G Sepharose (50 pl of 50% bead slurry), no secondary step is necessary if using streptavidin beads to pull down biotinylated compounds. After quick centrifugation, the pellets may be washed in lysis buffer containing increasing salt concentration (e.g., 150, 300, 500 mM of NaCl). The beads may be then re-equilibrated at 150 mM NaCl before addition of SDS-containing sample buffer and boiling. The beads and cell lysates may be electrophoresed using 4%-12% gradient Bis-Tris gels followed by transfer into Immobilon-P membranes. Alter blocking, blots may be incubated with an antibody that detects FITC or biotin, respectively and also with one or more antibodies that detect proteins that bind to the peptidomimetic macrocycle, including BCL2, MCL1, BCL-XL, A1, BAX, and BAK. The lysate blots are also probed with anti-Hsc-70 for loading control. Alternatively, after electrophoresis the gel may be silver stained to detect proteins that come down specifically with FITC-labeled or biotinylated compounds.

Cellular Penetrability Assays

A peptidomimetic macrocycle is, for example, more cell permeable compared to a corresponding uncrosslinked polypeptide. In some embodiments, the peptidomimetic macrocycles are more cell permeable than corresponding uncrosslinked polypeptides. Peptidomimetic macrocycles with optimized linkers possess, for example, cell penetrability that is at least two-fold greater than a corresponding uncrosslinked polypeptide, and often 20% or more of the applied peptidomimetic macrocycle will be observed to have penetrated the cell after 4 hours. To measure the cell penetrability of peptidomimetic macrocycles and corresponding uncrosslinked polypeptides, intact cells are incubated with fluoresceinated peptidomimetic macrocycles or corresponding uncrosslinked polypeptides (10 µM) for 4 hrs in serum free media at 37° C., washed twice with media and incubated with trypsin (0.25%) for 10 min at 37° C. The cells are washed again and resuspended in PBS. Cellular fluorescence is analyzed, for example, by using either a FACSCalibur flow cytometer or Cellomics' KineticScan® HCS Reader. Additional methods of quantitating cellular penetration may be used.

Cellular Efficacy Assays

The efficacy of certain peptidomimetic macrocycles is determined, for example, in cell-based killing assays using a variety of tumorigenic and non-tumorigenic cell lines and primary cells derived from human or mouse cell populations. Cell viability is monitored, for example, over 24-96 hrs of incubation with peptidomimetic macrocycles (0.5 to 50 µM) to identify those that kill at $EC_{50}<10$ µM. In this context, $EC_{50}$ refers to the half maximal effective concentration, which is the concentration of peptidomimetic macrocycle at which 50% of the population is viable. Several standard assays that measure cell viability are commercially available and are optionally used to assess the efficacy of the peptidomimetic macrocycles. In addition, assays that measure Annexin V and caspase activation are optionally used to assess whether the peptidomimetic macrocycles kill cells by activating the apoptotic machinery. For example, the Cell Titer-glo assay is used which determines cell viability as a function of intracellular ATP concentration.

In Vivo Stability Assay

To investigate the in vivo stability of the peptidomimetic macrocycles, the compounds are, for example administered to mice and/or rats by IV, IP, SC, PO or inhalation routes at concentrations ranging from 0.1 to 50 mg/kg and blood specimens withdrawn at 0', 5', 15', 30', 1 hr, 4 hrs, 8 hrs, 12 hrs, 24 hrs and 48 hrs post-injection. Levels of intact compound in 25 uL of fresh serum are then measured by LC-MS/MS as described herein.

In Vivo Efficacy in Animal Models

To determine the anti-oncogenic activity of peptidomimetic macrocycles of the invention in vivo, the compounds are, for example, given alone (IP, IV, SC, PO, by inhalation or nasal routes) or in combination with sub-optimal doses of relevant chemotherapy (e. g., cyclophosphamide, doxorubicin, etoposide). In one example, $5 \times 10^6$ SEMK2 cells (established from the bone marrow of a patient with acute lymphoblastic leukemia) that stably express luciferase are injected by tail vein in NOD-SCID, SCID-beige or NOD.1L2rg KO mice 3 hrs after they have been subjected to total body irradiation. Non-radiated mice may also be used for these studies. If left untreated, this form of leukemia is fatal in 3 weeks in this model. The leukemia is readily monitored, for example, by injecting the mice with D-luciferin (60 mg/kg) and imaging the anesthetized animals (e.g., Xenogen In Vivo Imaging System, Caliper Life Sciences, Hopkinton, Mass.). Total body bioluminescence is quantified by integration of photonic flux (photons/sec) by Living Image Software (Caliper Life Sciences, Hopkinton, Mass.). Peptidomimetic macrocycles alone or in combination with sub-optimal doses of relevant chemotherapeutics agents are, for example, administered to leukemic mice (8-10 days after injection/day 1 of experiment, in bioluminescence range of 14-16) by tail vein or IP routes at doses ranging from 0.1 mg/kg to 50 mg/kg for 7 to 21 days. Optionally, the mice are imaged throughout the experiment every other day and survival monitored daily for the duration of the experiment. Expired mice are optionally subjected to necropsy at the end of the experiment. Another animal model is implantation into NOD-SCID mice of DoHH2, a cell line derived from human follicular lymphoma that stably expresses luciferase. These in vivo tests optionally generate preliminary pharmacokinetic, pharmacodynamic and toxicology data.

Clinical Trials

To determine the suitability of the peptidomimetic macrocycles of the invention for treatment of humans, clinical trials are performed. For example, patients diagnosed with cancer and in need of treatment are selected and separated into treatment and one or more control groups, wherein the treatment group is administered a peptidomimetic macrocycle of the invention, while the control groups receive a placebo, a known anti-cancer drug, or the standard of care. The treatment safety and efficacy of the peptidomimetic macrocycles of the invention can thus be evaluated by performing comparisons of the patient groups with respect to factors such as survival and quality-of-life. In this example, the patient group treated with a peptidomimetic macrocycle show improved long-term survival compared to a patient control group treated with a placebo or the standard of care.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise

What is claimed is:

1. A compound of Formula (I):

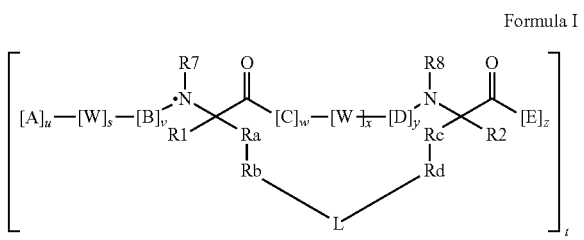

Formula I wherein each A, B, C, and E is independently a natural or non-natural amino acid;
D is a natural, or non-natural amino acid, amino acid analog,

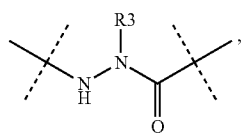

[—NH-L1-CO—], [—NH-L2-SO$_2$—] or [—NH-L3-];
W is a natural or non-natural amino acid or amino acid analog where the amino acid side chain contains a warhead;

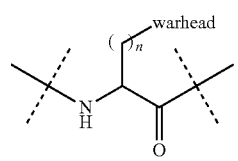

u and z are independently integers from 0-100;
v, w, and y are independently integers from 0-10;
t is 1,
s is 0 or 1, x is 0 or 1, wherein provided s is 0, x is 1, or provided x is 0, s is 1;
n is an integer from 1-5;
$R_a$ is $(CH_2)_m$, m=0-4, $R_b$ is $CH_2$, and R1 is —H, alkyl, alkenyl, alkynyl, arylalkyl, cycloalkyl, cycloalkylalkyl, heteroalkyl, or heterocycloalkyl, unsubstituted or substituted with halo; or $R_a$ is $(CH_2)_m$, m=0-4, $R_b$ is a $CH_2$, R1 is a $CH_2$ and $R_b$ and R1 are covalently bound to form a ring;
$R_c$ is $(CH_2)_m$, m=0-4, $R_d$ is $CH_2$, and R2 is —H, alkyl, alkenyl, alkynyl, arylalkyl, cycloalkyl, cycloalkylalkyl, heteroalkyl, or heterocycloalkyl, unsubstituted or substituted with halo; or $R_c$ is $(CH_2)_m$, m=0-4, $R_d$ is a $CH_2$, R2 is a $CH_2$ and $R_d$ and R2 are covalently bound to form a ring;
L is a macrocycle-forming linker of the formula -L1-L2-L3-;
L1, L2 and L3 are independently a bond, alkylene, alkenylene, alkynylene, heteroalkylene, cycloalkylene, heterocycloalkylene, cycloarylene, heterocycloarylene, or [—R4-K—R4-]$_p$, each being optionally substituted with R5, and p is an integer from 1 to 5;
R3 is hydrogen, alkyl, alkenyl, alkynyl, arylalkyl, heteroalkyl, cycloalkyl, heterocycloalkyl, cycloalkylalkyl, cycloaryl or heterocycloaryl, optionally substituted with R5;
each K is independently O, S, SO, SO$_2$, CO, CO$_2$, or CONR$_3$;
each R4 is independently alkylene, alkenylene, alkynylene, heteroalkylene, cycloalkylene, heterocycloalkylene, arylene, or heteroarylene;
each R5 is independently halogen, alkyl, —OR6, —N(R6)$_2$, —SR6, —SOR6, —SO2R6, —CO$_2$R6, a fluorescent moiety, a radioisotope or a therapeutic agent;
each R6 is independently —H, alkyl, alkenyl, alkynyl, arylalkyl, cycloalkylalkyl, heterocycloalkyl, a fluorescent moiety, a radioisotope or a therapeutic agent;
R7 is —H, alkyl, alkenyl, alkynyl, arylalkyl, cycloalkyl, heteroalkyl, cycloalkylalkyl, heterocyeloalkyl, cycloaryl, or heterocycloaryl, optionally substituted with R4, or part of a cyclic structure with an A residue;
R8 is —H, alkyl, alkenyl, alkynyl, arylalkyl, cycloalkyl, heteroalkyl, cycloalkylalkyl, heterocycloalkyl, cycloaryl, or heterocycloaryl, optionally substituted with R4, or part of a cyclic structure with an E residue;
warhead is one of the moieties 2a, 2b, 2c, 2d, 2e, 2f, 2g, 2h, 2i, 2j, 2k, 2m, 2n, 2o or 2p shown as follows,

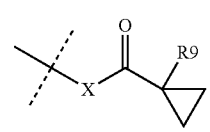

2a

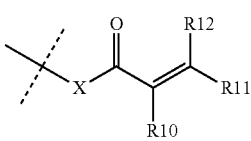

2b

-continued

2c 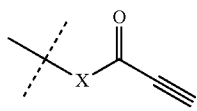

2d 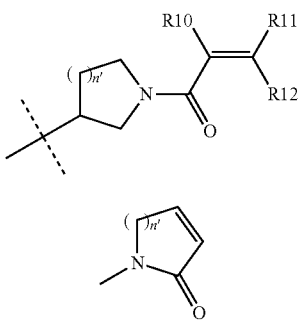

2e

2f

2g

2h 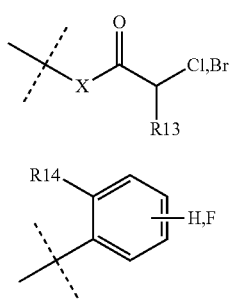

2i

2j 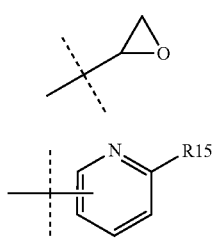

2k

2l 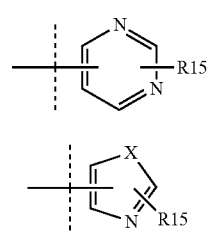

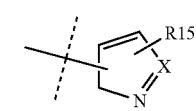

-continued

2m 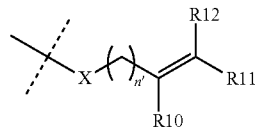

2n 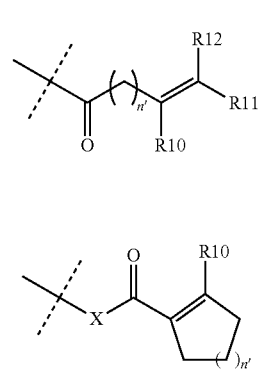

2o

2p wherein;

X is C, NH, NR8, O or S;

n' is an integer from 0-3;

R9 is hydrogen, CN, or (CO)CH$_3$;

R10 is hydrogen, or a bivalent C1-4 saturated or unsaturated, straight or branched, hydrocarbon chain, or an electron-withdrawing group;

R11 and R12 are each independently hydrogen, a bivalent C1-4 saturated or unsaturated, straight or branched, hydrocarbon chain, —N(R6)$_2$, —CH$_2$N(R6)$_2$, —CH$_2$CH$_2$N(R6)$_2$, C(O)N(R6)$_2$, —C(O)OR6, —CH$_2$C(O)OR6 or —CH$_2$CH$_2$C(O)OR6;

R13 is hydrogen, a bivalent C1-4 saturated or unsaturated, straight or branched, hydrocarbon chain;

R14 is an electron-withdrawing group chosen from NO$_2$, CF$_3$, CN, —NHC(O)CHCH$_2$, —NHC(O)CH$_2$Br,

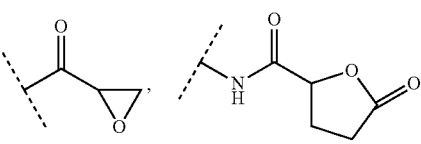

or SO$_2$F;

R15 is a halogen, a C2 alkynyl side chain optionally substituted with oxo, halogen, NO$_2$, or CN, or a C2 alkenyl side chain optionally substituted with oxo, halogen, NO$_2$, or CN.

2. A compound of claim 1, wherein R15 is —CH=CH$_2$ or —C≡CH.

3. A compound of claim 1, which is a compound of Formula Ia,
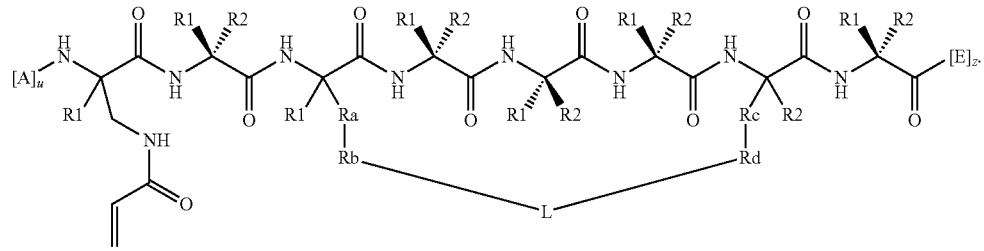
4. A compound of claim 1, which is a compound of Formula Id-Io,

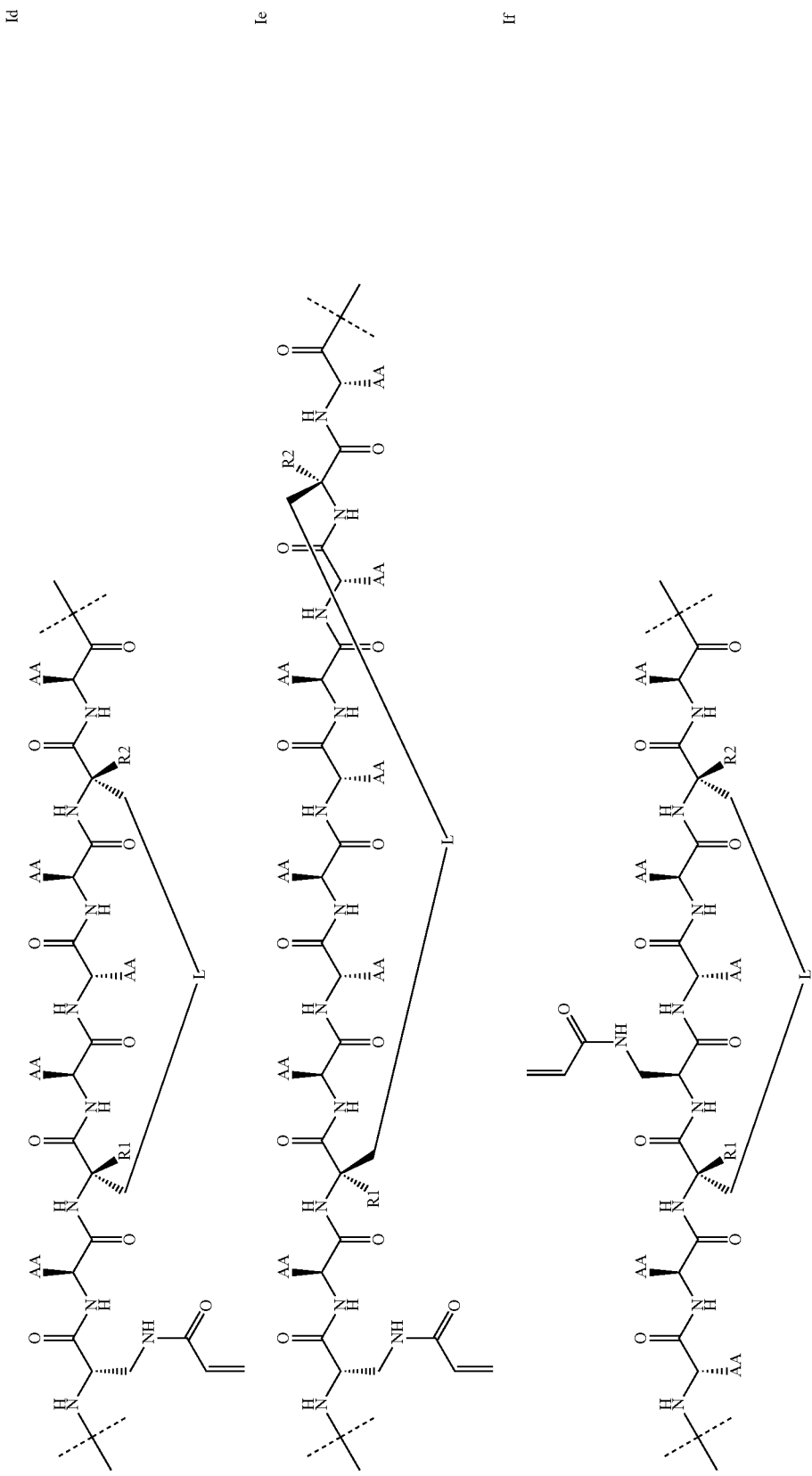

-continued
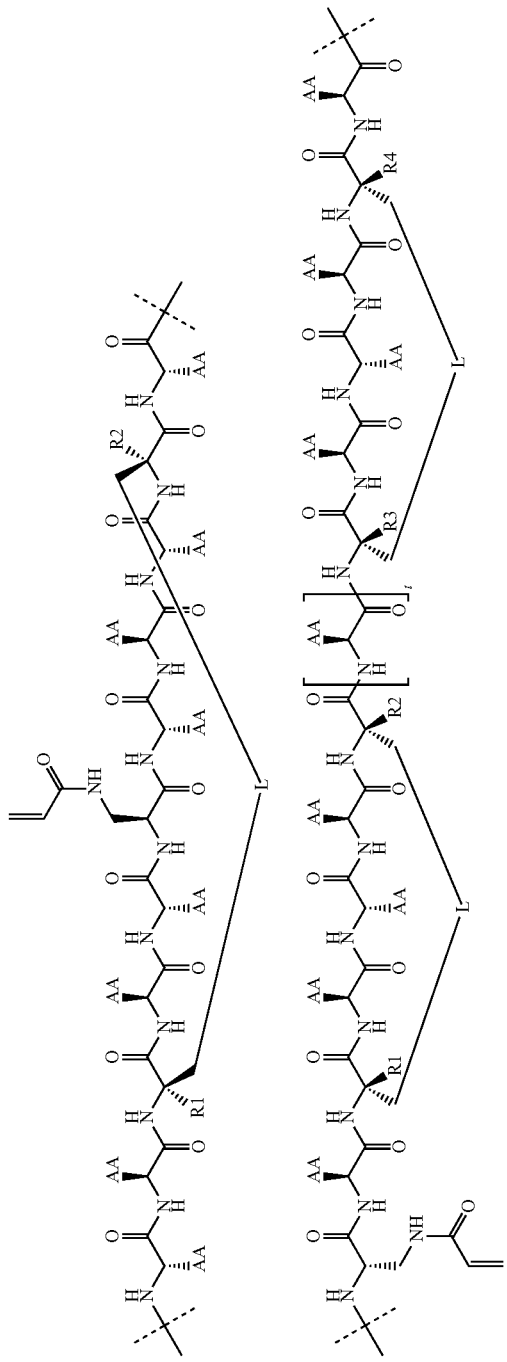
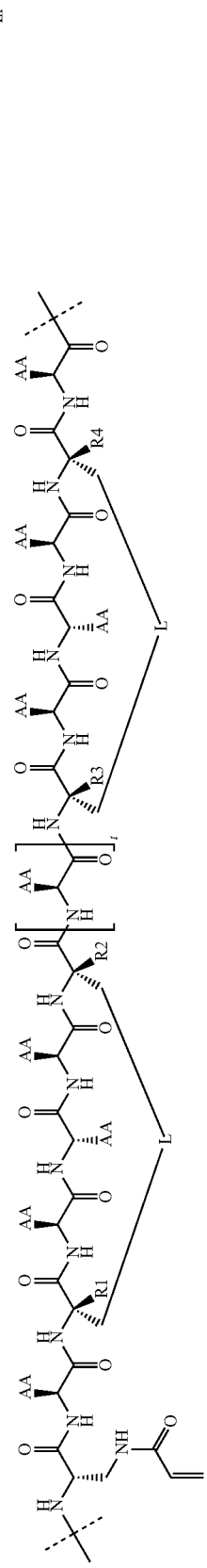
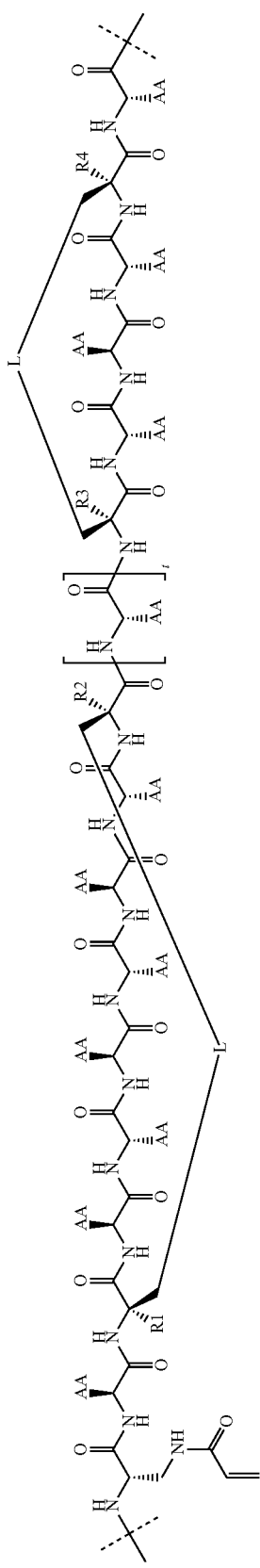
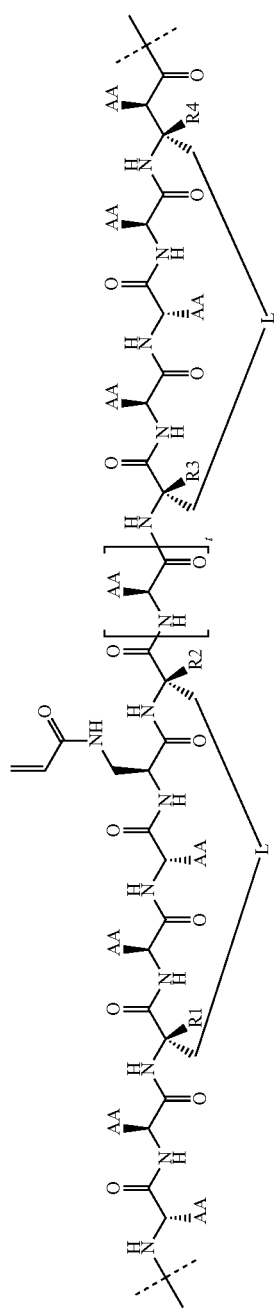

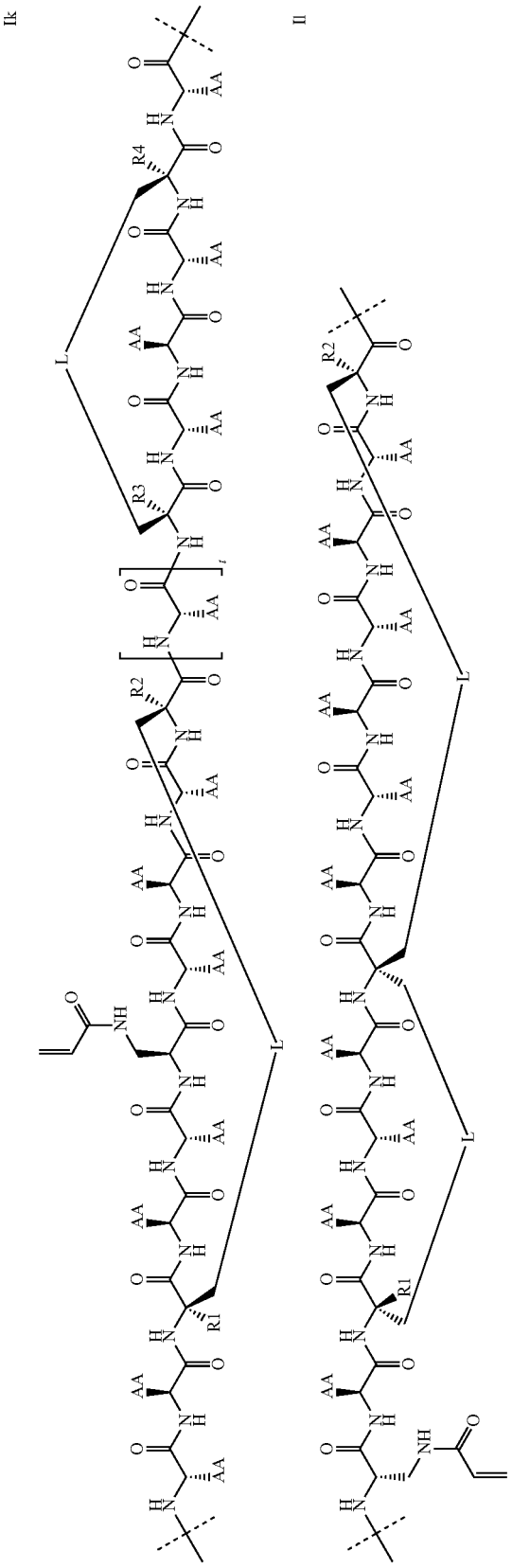
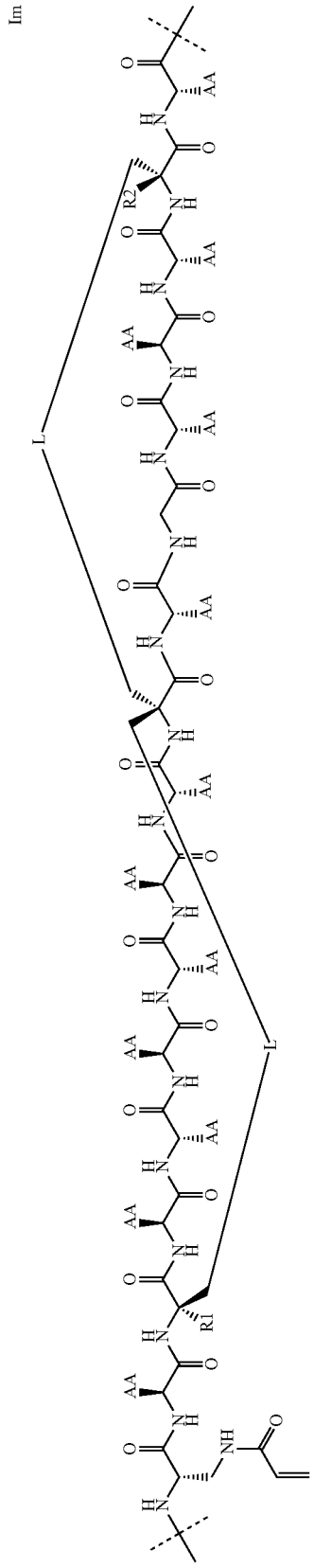

-continued
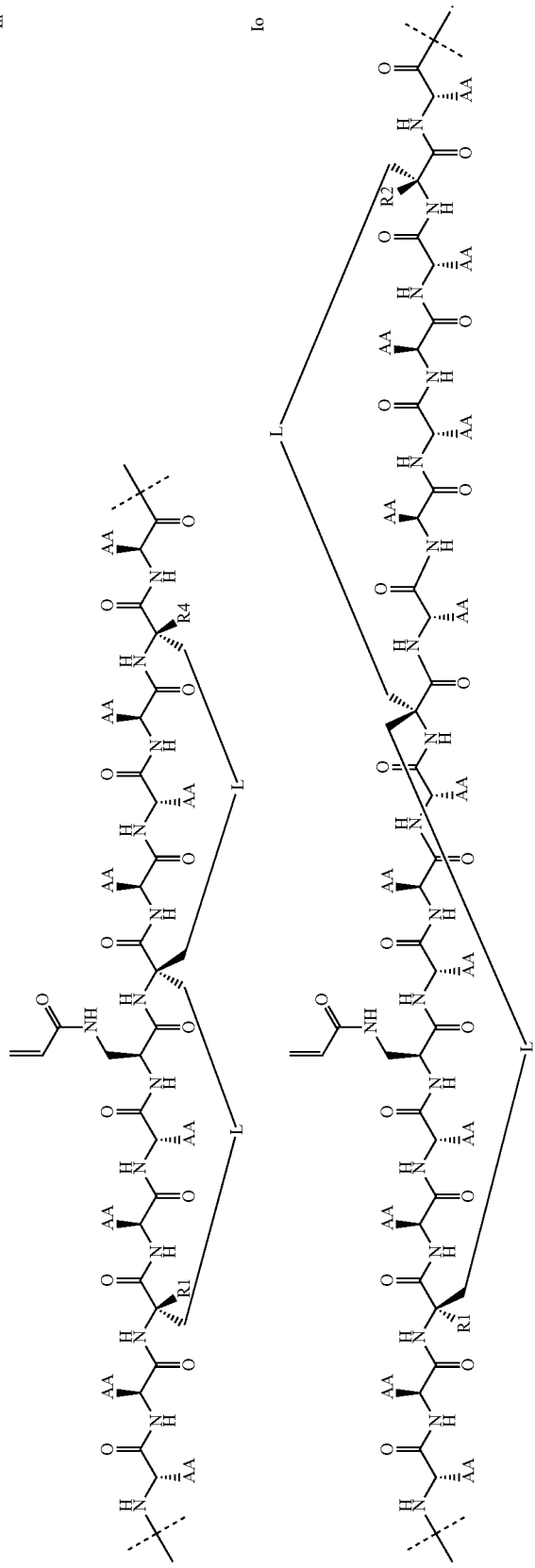

5. A compound of claim 1, wherein L is one of L3-L8,

L3
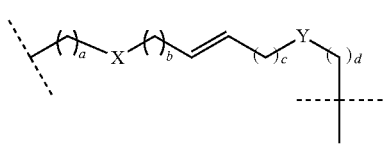

where X, Y = —CH$_2$—, O, S or NH
a, b, c, d = 0-10

L4
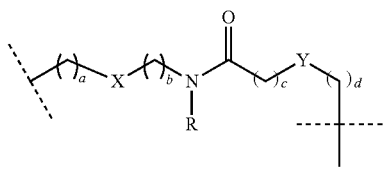

where X, Y = —CH$_2$—, O, S or NH
a, b, c, d = 0-10
R = H, alkyl, other substituent L5
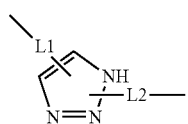
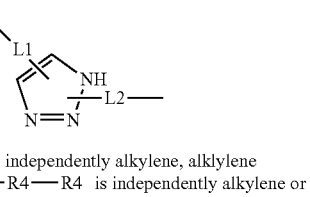

L1 and L2 are independently alkylene, alklylene
or —R4—K—R4— R4 is independently alkylene or alkylene
K is O, S, SO, SO$_2$, CO, CO$_2$ or CONR4

-continued

L6
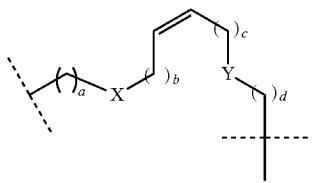

where X, Y = —CH$_2$—, O, S or NH
a, b, c, d = 0-10

L7
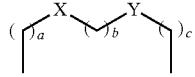

where X, Y = —CH$_2$—, O, S or NH
a, b, c, d = 0-10

L8
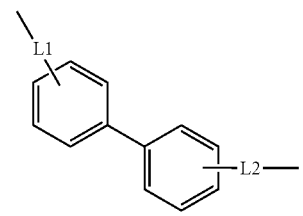

L1 and L2 are independently alkylene, alklylene
or —R4—K—R4— R4 is independently alkylene or alkylene
K is O, S, SO, SO$_2$, CO, CO$_2$ or CONR4

6. A compound of claim 1, which is a compound of Formula Ijj-Formula Iiii,

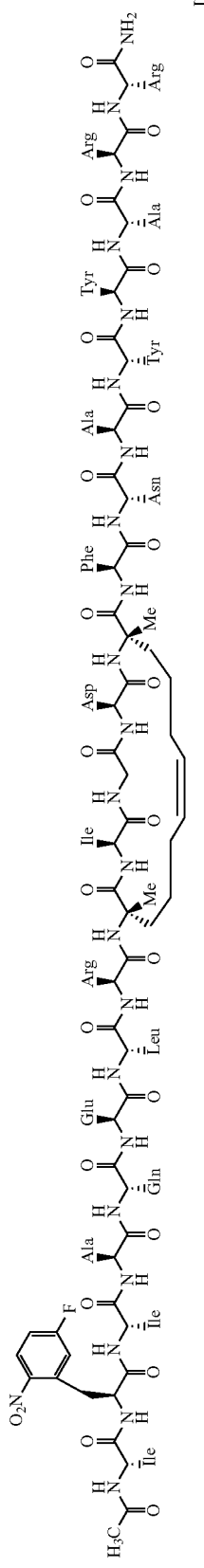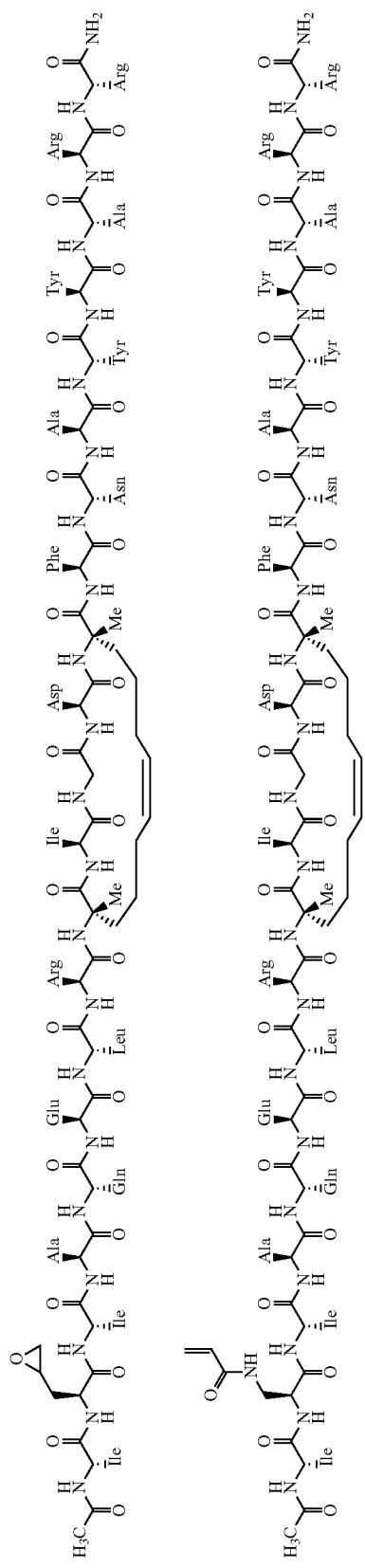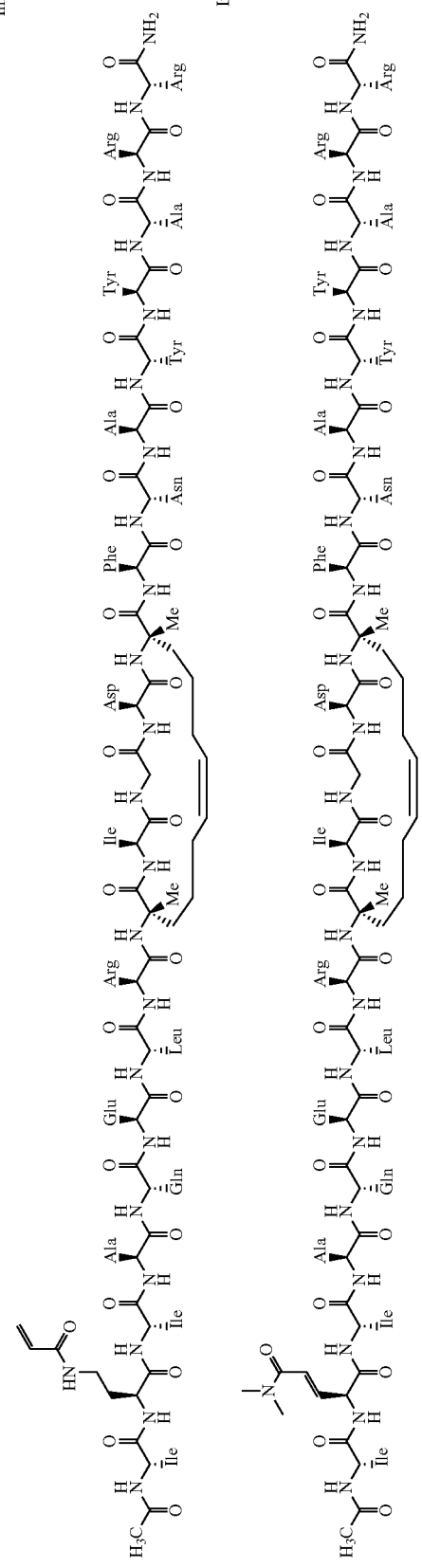

-continued
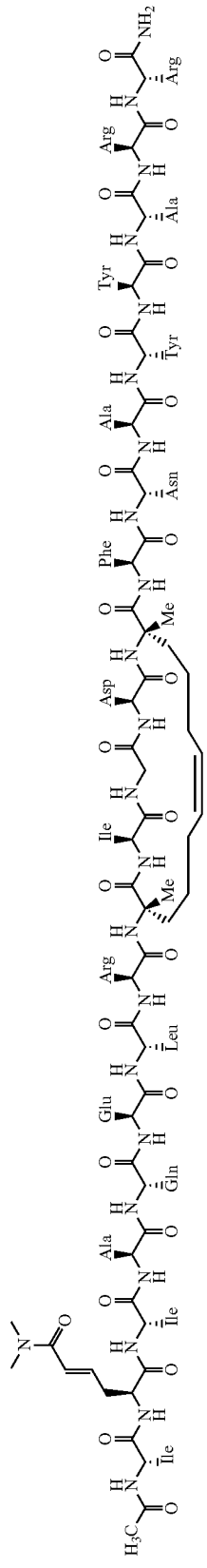
Ioo
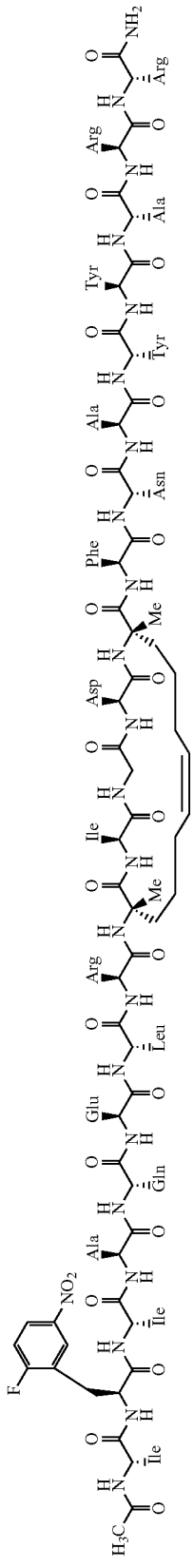
Ipp
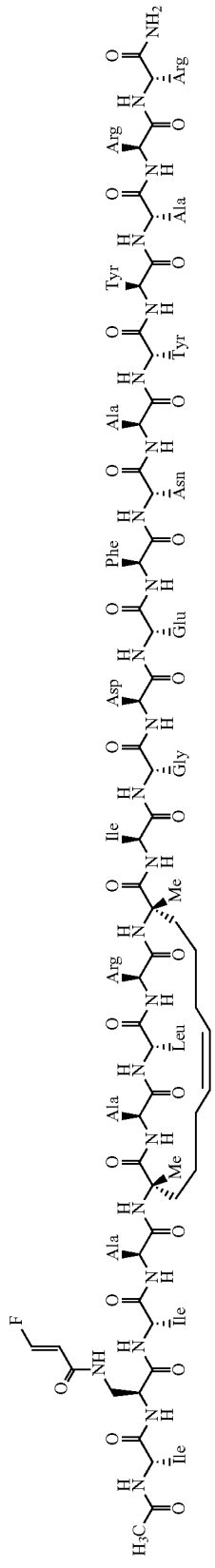
Iqq
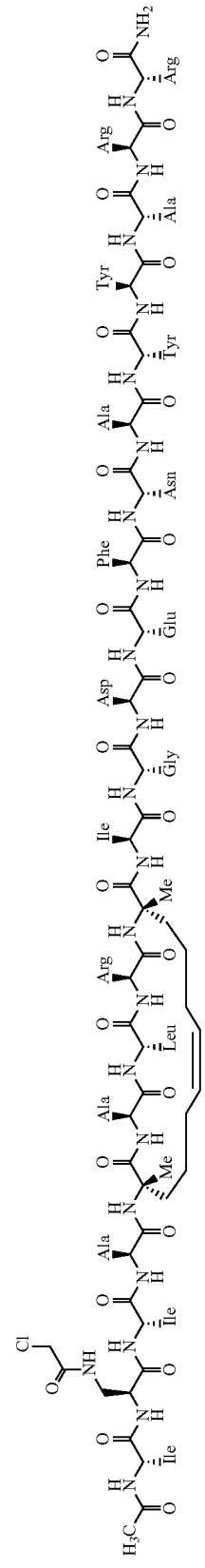
Irr

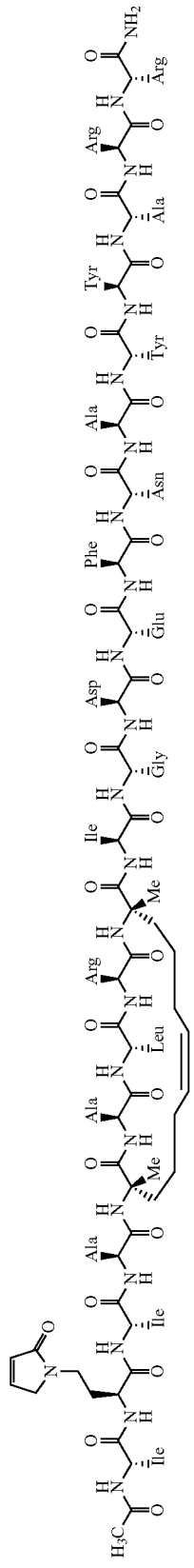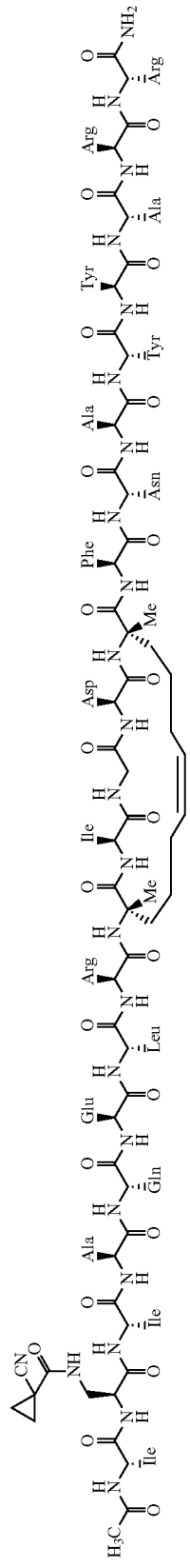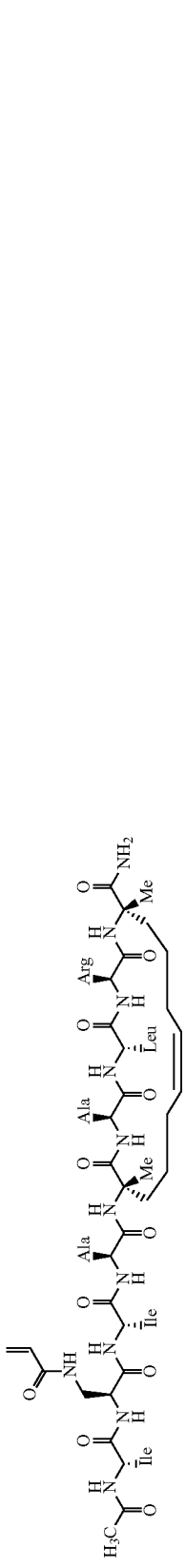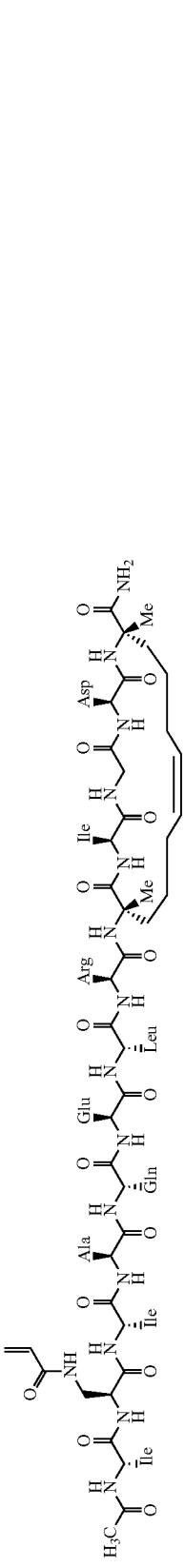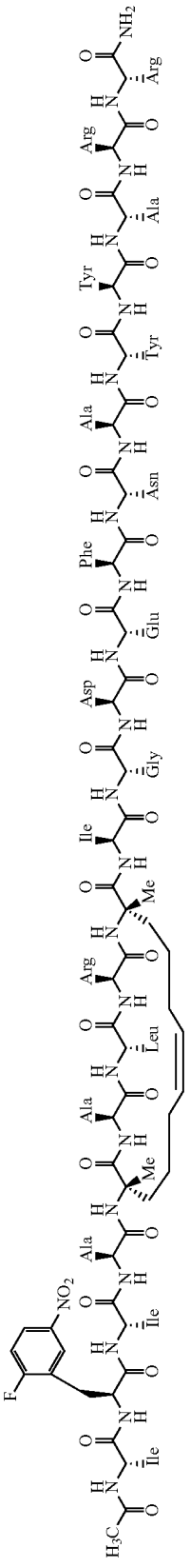

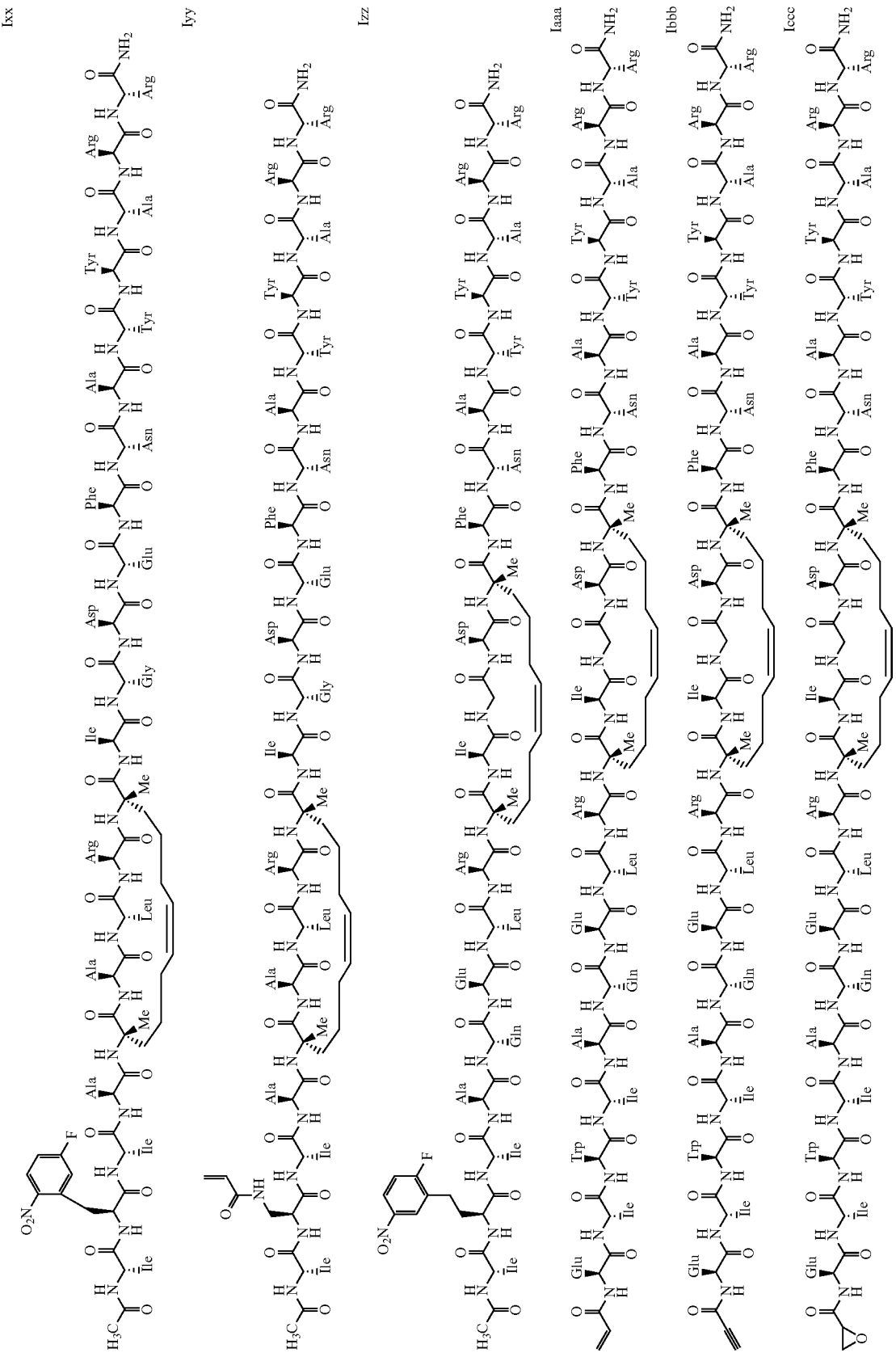

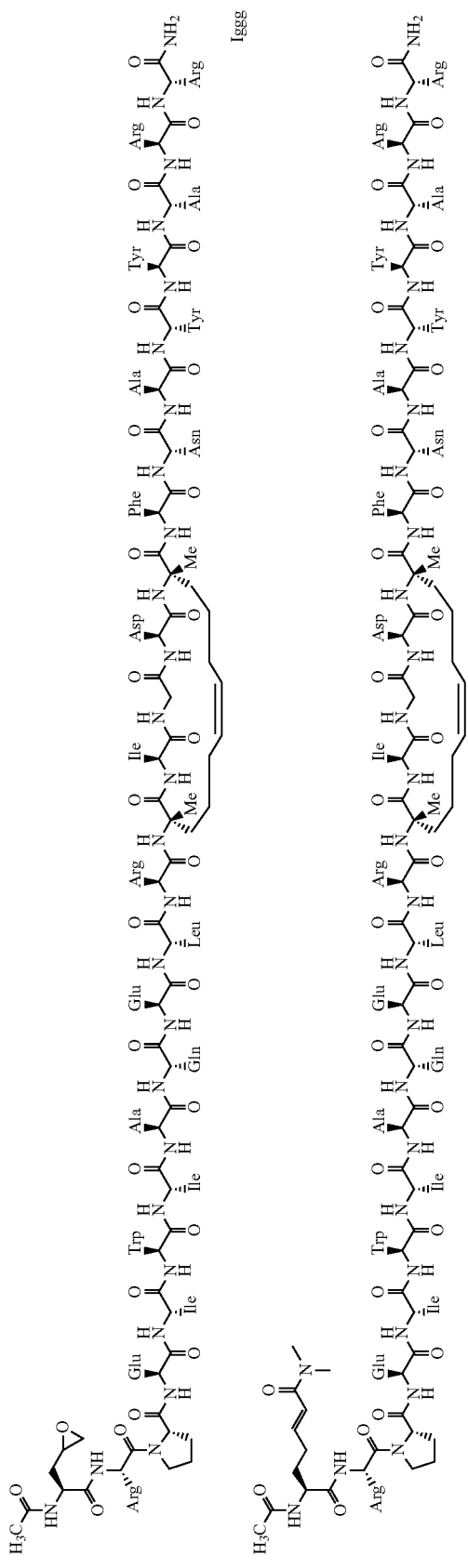

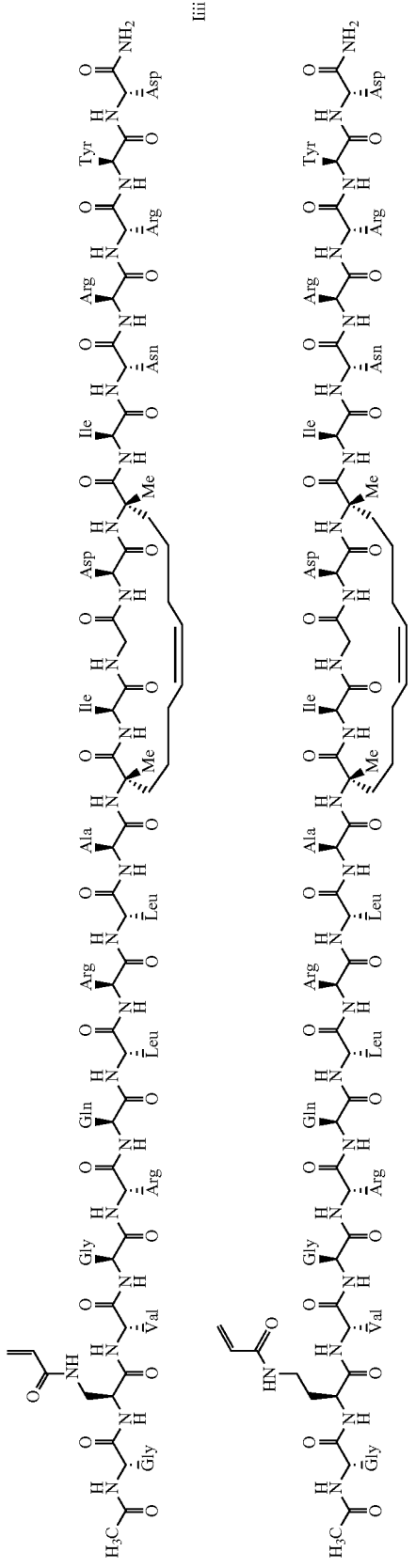

7. A pharmaceutical composition comprising a compound according to claim 1, and a pharmaceutically acceptable adjuvant, carrier or vehicle.

8. A method for inhibiting a protein-protein interaction activity in a cell comprising contacting the cell with a compound of claim 1.

9. The method according to claim 8, wherein the protein-protein interaction is inhibited irreversibly.

10. The method of claim 9, wherein at least one protein is BCL2-A1, wherein BCL2-A1 is irreversibly inhibited by covalently modifying Cys55 of BCL2-A1 with the compound.

11. A method for treating a BCL2-A1 mediated disorder in a patient in need thereof, comprising administering to the patient a composition comprising a compound according to claim 1.

* * * * *